(12) United States Patent
Burdick et al.

(10) Patent No.: US 8,095,210 B2
(45) Date of Patent: Jan. 10, 2012

(54) PROSTHETIC DEVICES AND METHODS AND SYSTEMS RELATED THERETO

(75) Inventors: Joel W. Burdick, Pasadena, CA (US); Jorge G. Cham, Pasadena, CA (US); Zoran Nenadic, Irvine, CA (US); Edward A. Branchaud, Lawrence, MA (US); Michael T. Wolf, Pasadena, CA (US); Richard A. Andersen, La Canada Flintridge, CA (US)

(73) Assignee: California Institute of Technology, Pasadena, CA (US)

( * ) Notice: Subject to any disclaimer, the term of this patent is extended or adjusted under 35 U.S.C. 154(b) by 1392 days.

(21) Appl. No.: 11/625,230

(22) Filed: Jan. 19, 2007

(65) Prior Publication Data

US 2008/0177196 A1 Jul. 24, 2008

(51) Int. Cl.
*A61B 5/04* (2006.01)

(52) U.S. Cl. ........................................ 600/544; 600/545

(58) Field of Classification Search .......... 600/544–545; 700/56–66
See application file for complete search history.

(56) References Cited

U.S. PATENT DOCUMENTS

| | | | | |
|---|---|---|---|---|
| 5,928,143 | A * | 7/1999 | McNaughton | 600/373 |
| 6,470,226 | B1 * | 10/2002 | Olesen et al. | 700/56 |
| 7,493,178 | B2 * | 2/2009 | Abu Nassar et al. | 700/56 |

* cited by examiner

*Primary Examiner* — Patricia Mallari
*Assistant Examiner* — Michael D'Angelo
(74) *Attorney, Agent, or Firm* — Seth D. Levy; Davis Wright Tremaine LLP

(57) ABSTRACT

The present invention relates to systems and methods for controlling neural prosthetic devices and electrophysiological recording equipment, and for using the same in clinical operation. Various embodiments of the invention are directed to an algorithm for autonomously isolating and maintaining neural action potential recordings. The algorithm may be used in connection with a neural interface microdrive capable of positioning electrodes to record signals from active neurons.

33 Claims, 25 Drawing Sheets

Figure 5

| Threshold Name | Signal Quality Region |
|---|---|
| | Danger of damaging neuron → back away |
| MAX_SNR → | —————————— |
| | Great isolation → stop moving to avoid neuron damage |
| STOP_SNR → | —————————— |
| | Acceptable isolation → stop moving if maximum of isolation curve detected |
| MIN_SNR → | —————————— |
| | High enough for maximization procedure; too low to declare isolation |
| MIN_TRACK_SNR → | —————————— |
| | Signal quality too low for reliable measurements → do not follow gradient |
| 0 → | —————————— |

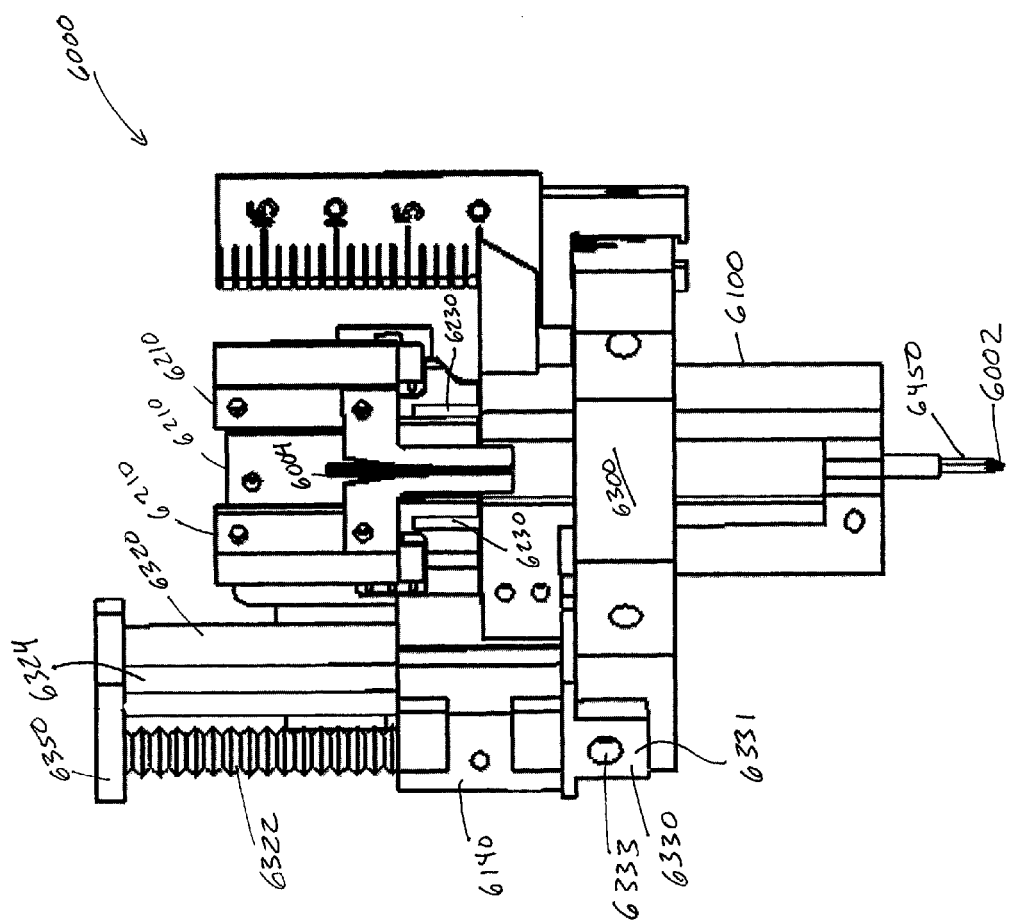

Back

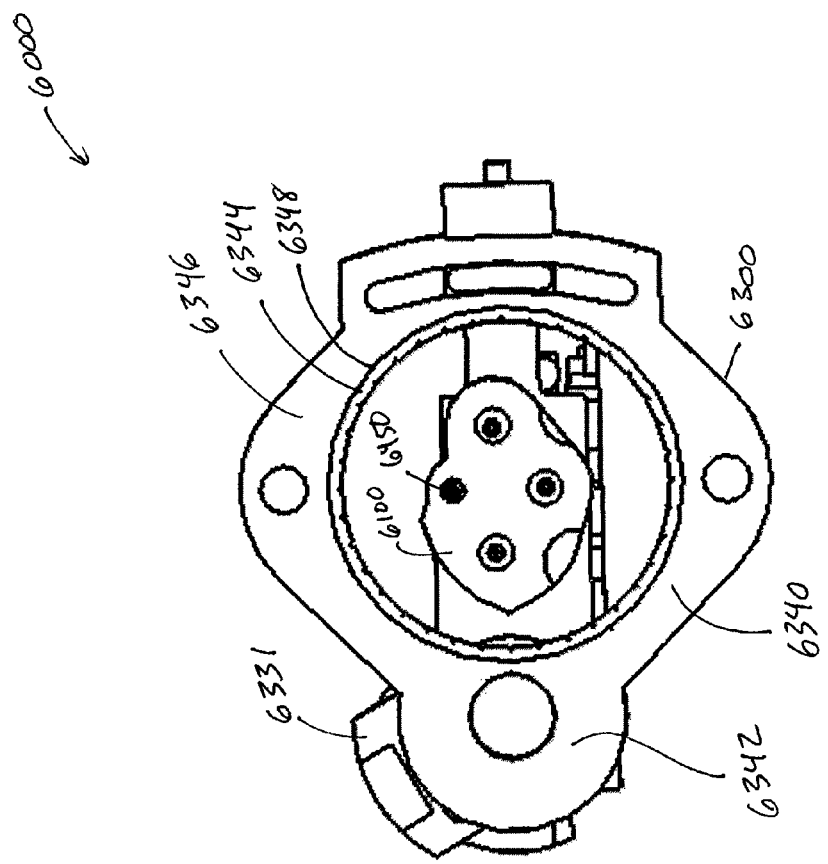
Figure 12C Bottom

Top

PROSTHETIC DEVICES AND METHODS AND SYSTEMS RELATED THERETO

FEDERAL SUPPORT

This invention was made with U.S. Government support under DARPA Grant No. MDA972-00-1-0029, National Institutes of Health Grant No. R01 EY013337, National Science Foundation Grant No. EEC-9402726, and Office of Naval Research Grant No. N00014-01-1-0035. The U.S. Government has certain rights in this invention.

BACKGROUND

1. Field

The present disclosure relates to systems, methods, and devices for controlling neural prosthetic devices and electrophysiological recording equipment, and for using the same in clinical operation.

2. Related Art

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The ability to interact directly with the nervous system to control a computer cursor or robot arm has been demonstrated by several researchers. See, e.g., J. Wessberg et al., "Real-time prediction of hand trajectory by ensembles of cortical neurons in primates," *Nature*, 408(6810): 361-365 (2000); J. M. Carmena et al., "Learning to control a brain-machine interface for reaching and -grasping by primates," *PLoS*, 1:193-208 (2003); D. M. Taylor et al., "Direct cortical control of 3D neuroprosthetic devices," *Science*, 296:1829-1832 (2002); P. R. Kennedy and R. A. Bakay, "Restoration of neural output from a paralyzed patient by a direct brain connection," *Neuroreport*, 9(8):1707-11 (1998); and R. A. Andersen et al., "Cognitive Neural Prosthetics," *Trends in Cog. Sci.*, 8(11):486-493 (November 2004).

These advances in neural prosthetic systems may provide patients with lost motor function due to spinal cord injury, stroke, neurodegenerative diseases, and the like with the ability to regain access to their surroundings. Despite these breakthroughs, however, many challenges remain. See, e.g., J. P. Donoghue, "Connecting cortex to machines: recent advances in brain interfaces," *Nature Neurosci*, 5:1085-1088A (2002). A fundamental problem, for instance, lies in creating interface devices capable of sustaining interaction with neuronal populations for long periods of time in a practical and reliable manner. Long-term neural interfacing demands that the overall device be implantable, safe, and minimally obtrusive. Further, the device should require minimal maintenance.

Information transfer and processing in the brain occurs through the transmission of electrical pulses, called action potentials, between neurons. Information about the various areas or regions of the brain may be gained by studying patterns of action potentials associated with individual neurons while a subject (e.g., a rat, fly, monkey, or human) is presented with a stimulus or engages in a behavioral task. While noninvasive methods such as fMRI or EEG recordings can provide gross estimates of activity levels in a particular region of the brain, action potentials of individual neurons must be examined to understand how information is processed within local neural networks.

Action potentials may be recorded extracellularly by inserting electrodes (typically sharpened metal wires insulated along their length and exposed at the tip) into the neural tissue. Because action potentials emitted by a neuron are highly stereotyped in shape and information is encoded in their timing, a successful extracellular recording is one in which the firing of action potentials of individual neurons can reliably be detected. These neurons are then considered "isolated" in the recording. Isolated neural recordings may be essential to the proper function of a neural prosthetic. Such recordings may also form the basis for fundamental scientific investigations into the function of the brain and the means by which information is encoded in neural networks.

There are two dominant modes of recording: acute and chronic. In acute recording, electrodes are inserted and removed from the neural tissue during each recording session. In chronic recording, electrodes are surgically implanted and remain in place for weeks, months, or possibly years at a time. As used herein, the term semi-chronic recording is used to refer to a recording made by electrodes implanted in neural tissue for a period of time longer than a single recording session but somewhat shorter than the duration of implantation used with chronic recordings. For example, the implants used to make a semi-chronic recording may be implanted several days or weeks.

For acute recordings, a portion of the skull over the brain region of interest is removed and replaced with a sealable chamber. During a recording session, a device termed a microdrive is affixed to the opened chamber and used to advance the electrodes into the neural tissue, usually in a motorized fashion. The electrodes are advanced along a straight line, with the axis of penetration chosen by an experimenter or operator. In conventional practice, the electrode motion is controlled manually by the operator until one or more neurons is/are sufficiently isolated. This process is commonly guided by experience, intuition, and feedback from visual and auditory representations of the voltage signal detected by the electrodes. Such acute recordings are typically used for basic scientific research, but they may also be used to implement a neural prosthetic in a semi-chronic fashion.

Typically, the goal is to position each electrode of the microdrive close enough to a single and unique neuron for a high quality recording of the electrical activity of the neuron, yet far enough away to avoid damaging the neuron. In this manner, the number of neurons recorded may correspond to the number of electrodes. Normally, the electrical recording site must be within a 40 micron to 60 micron radius and preferably about a 50 micron radius of the unique neuron's soma to obtain an extracellular signal that can be successfully differentiated from background noise. See, e.g., C. Gray et al., "Tetrodes markedly improve the reliability and yield of multiple single-unit isolation from multi-unit recordings in cat striate cortex," *J. Neurosci. Methods*, 63:43-54 (1995). Without such successful positioning, an electrode immersed in neural tissue may not successfully record any neural signals, thereby rendering the electrode useless. During the course of a typical recording session, such as may occur during a basic scientific experiment or the simulation of a neural prosthetic, each of the electrodes must be repositioned periodically to maintain a desired level of signal quality. Repositioning may be necessitated by tissue migration and/or decompression that occurs naturally. The process of isolating and maintaining neural signals consumes a significant amount of the operator's time and focus. The considerable time and effort needed to affect the neural isolations considerably reduces the efficiency with which electrophysiological recording experiments can be performed.

Simultaneous recordings made with many electrodes are becoming an increasingly important technique for understanding how local networks of neurons process information, as well as how brain areas communicate with each other. Commercial microdrives (i.e., motorized electrodes that receive movement commands provided manually by a human operator) with sixteen or more electrodes are currently available. See, e.g., S. Baker et al., "Multiple single unit recording in the cortex of monkeys using independently moveable microelectrodes," *J. Neurosci. Methods*, 94(1):5-17 (1999). As the number of electrodes increases, the task of positioning each electrode to maintain a high quality neural signal becomes intractable for a single operator to manage. Data collection in experiments that use multiple electrodes is limited by how many neural signal channels the operator can effectively monitor.

In chronic recordings (which are the most conventional type of recordings used as the front end of a neural prosthesis), stationary multi-electrode assemblies, which are typically bundles or arrays of thin wires or silicon probes, are surgically implanted in the region of interest. See, e.g., I. Porada et al., "Rabbit and monkey visual cortex: more than a year of recording with up to 64 microelectrodes," *J. Neurosci. Methods*, 95:13-28 (2000); J. Williams et al., "Long-term neural recording characteristics of wire microelectrode arrays implanted in cerebral cortex," *Brain Res. Protocols*, 4:303-13(1999); and P. Rousche and R. Normann, "Chronic recording capability of the Utah intracortical electrode array in cat sensory cortex," *J. Neurosci. Methods*, 82:1-15 (1998).

The signal yield of the implanted array (i.e. the percentage of the electrodes of the array that record active neurons) depends upon the luck of the initial surgical placement. As mentioned above, it is believed that the electrically active tip of a recording electrode must lie within approximately 40-60 microns of the neuron's soma to provide a useful signal. The neurons close enough to a particular electrode may not encode the proper task for the prosthetic system, rendering that electrode practically useless. Unfortunately, in some cases, one or more of the electrodes may be placed in inactive tissue or the wrong brain region. Even if properly placed, the active recording site of the electrode may not sit sufficiently close to an active neuron. Moreover, even if the electrode is initially well placed, tissue migrations (e.g., caused by blood pressure variations, breathing, and mechanical shocks), inflammation, neuron expiration, reactive gliosis, and other local tissue reactions can cause subsequent loss of signal; thereby reducing or disabling the function of the recording array over time.

To date, all practical neuroprosthetic systems have used implanted multi-electrode arrays whose electrodes have a fixed geometry. These fixed geometries suffer from the problems outlined above.

A chronic implant in which the electrodes can be continually repositioned after implantation may overcome these limitations and greatly extend the signal yield and lifetime of chronic array implants. Longevity of chronically implanted electrode arrays is necessary because repeated and frequent surgical intervention to implant new electrodes is not desirable, and may place the subject (e.g., a neuroprosthetic patient) at greater risk for surgical complications.

Alternatively, one could use a miniature chronic microdrive of the type often used in basic neuroscience research. These simple microdrives are typically implanted in non-human primates, rats, mice, and rabbits to enable chronic recordings. In such devices, each of the electrodes may be repositioned manually by either turning lead screws or temporarily connecting a conventional motorized microdrive (of the type typically used in acute recordings) to the array in order to adjust the position of each of the electrodes. See, e.g., P. D. Wall, J. Freeman, D. Major, "Dorsal horn cells in spinal and in freely moving rats," *Exp Neural*, 19: 519-529 (1967); J. L. Kubie, "A Driveable bundle of microwires for collecting single-unit data from freely-moving rats," *Physiology & Behavior*, 32: 115-118 (1984); B. P. Vos et al., "Miniature carrier with six independently moveable electrodes for recording of multiple single-units in the cerebellar cortex of awake rats," *J Neurosci Methods*, 94: 19-26 (1999); S. Venkatachalam et al., "Ultra-miniature headstage with 6-channel drive and vacuum-assisted micro-wire implantation for chronic recording from the neocortex," *J Neurosci Methods*, 90: 37-46 (1999); J. D. Kralik et al., "Techniques for long-term multisite neuronal ensemble recordings in behaving animals," *J. Neurosci. Meth.*, 25:121-50 (2001); A. S. Tolias et al., "Coding visual information at the level of populations of neurons," Program No. 557.5., 2002 Abstract Viewer/Itinerary Planner, Washington, D.C.: Society for Neuroscience (2002); J. G. Keating and G. L. Gerstein, "A chronic multi-electrode microdrive for small animals," *J Neurosci Meth.*, 117: 201-206 (2002); K. L. Hoffman and B. L. McNaughton, "Coordinated reactivation of distributed memory traces in primate neocortex," *Science*, 297: 2070-2073 (2002); and R. C. deCharms, et al., "A multielectrode implant device for the cerebral cortex," *J Neurosci Meth.*, 93: 27-35 (1999).

Even if motorized, chronic microdrives typically face the challenge of requiring constant human supervision to reposition the electrodes to achieve a desired level of signal quality. This process can become tedious and even impractical (particularly if the array is used as part of neural prosthetic) as the number of electrodes increases. See S. N. Baker et al., "Multiple single unit recording in the cortex of monkeys using independently moveable microelectrodes," *J. Neurosci. Meth.*, 94:5-17 (1999); and M. S. Fee and A. Leonardo "Miniature motorized microdrive and commutator system for chronic neural recording in small animals," *J Neurosci Methods*, 112: 83-94 (2001).

The inventors have earlier described initial steps towards a chronic multi-electrode implant in which the electrodes can be continually and autonomously repositioned after implantation. See E. Branchaud et al., "A Miniature Robot for Autonomous Single Neuron Recordings," *IEEE Conf. on Robotics and Automation*, Barcelona, Spain (April 2005); Cham et al., "Semi-chronic motorized microdrive and control algorithm for autonomously isolating and maintaining optimal extracellular action potentials," *J. Neurophysiol.*, 93(1): 570-579 (January 2005); and C. Pang et al., "A New Multi-Site Probe Array with Monolithically Integrated Parylene Flexible Cable for a Neural Prosthesis," *Proc. 27th Conf. IEEE-EMBS* (2005). To be useful in a clinical application, such as using neural recordings to generate control signals for an external device (e.g., neural prosthetics), the position of the electrodes of the chronic multi-electrode implant must be autonomously controlled to maintain a desirable level of signal quality. Additionally, an autonomous control algorithm that could position electrodes in a chronic multi-electrode implant could also be useful for the control of electrode positioning during an acute recording experiment of the type used in many neuroscience research laboratories.

In order for the chronic multi-electrode implant to operate autonomously and without the aid of an operator, the neuron isolation and signal quality maintenance functions performed by the operator must be automated. When isolating a neuron, the operator performs a number of difficult tasks, including event detection (i.e., detecting the presence and onset of an action potential), unsupervised classification of neural signals (i.e., classifying neural events without a priori knowledge of their number and structure), and accounting for stochastic neuron activity and complex mechanical interactions between the electrode and the neural tissue. Following is a brief discussion of several of the major challenges faced in automating the isolation process.

Unsupervised detection, classification, and data association can present a challenge. Action potentials of varying amplitudes and shapes must be autonomously detected and grouped by the neuron from which they originated. In conventional practices, this process is normally performed by the operator who manually sets thresholds and identifies distinguishing signal features. The data association problem is also faced when attempting to track the signals arising from distinct neurons while moving the electrode.

Variable firing rates can also present a challenge. A general procedure for autonomously isolating a neuron involves sampling the amplitude of action potentials at several locations and searching for the local maximum of the signal quality. Depending on the behavioral state of the recording subject, the neuron that is being isolated may stop firing action potentials for one or more sampling periods, leading to false estimates of the signal amplitude at those locations.

During the initial insertion of the electrodes, neural tissue is compressed, and subsequent decompression causes the neurons to drift relative to the electrode. Optimal recording positions are moving targets. It is quite common for action potentials that have been observed for some time to disappear; presumably, the neuron has either drifted out of range or stopped firing. Also, after a neuron has been isolated, the electrode must be readjusted periodically to maintain the isolation. Often, neurons drift away from the line of travel of the electrode and become impossible to isolate or reisolate.

Local electrode-tissue interactions can be a challenge. In addition to the gross tissue relaxation occurring over several hours of an experiment, local mechanical coupling between the electrode tip and the neural tissue can cause hysteresis in the recorded neural signal. It is believed that there may be stiction between the electrode tip and the tissue. Additionally, because of tissue compression from the electrode insertion, when the electrode moves backward, the tissue may relax with it, resulting in a smaller relative movement between the electrode tip and the tissue than expected. This hysteresis is highly variable in magnitude, limits control action, and adds uncertainty to the electrode placement.

Finally, neuron damage can be a challenge. The electrode can potentially puncture and damage neurons when the electrode moves to achieve isolation or the neural tissue relaxes towards a stationary electrode.

Creating mechanisms and devices for small bio-robotic devices, such as chronic multi-electrode implants and microdrives, poses design and manufacturing challenges that strain the capabilities of traditional manufacturing processes even at the mesoscale level. Traditional manufacturing techniques rely on assemblies of pre-manufactured parts and fasteners that can compromise the reliability of the device. Fasteners and connectors not only take up a large percentage of the design volume at small scales, but can often work themselves loose or give way to leaks in the wet conditions of living tissue. Devices constructed using conventional fastening techniques may also lack the durability required to withstand frequent sterilization required for their use.

A chronic or semi-chronic microdrive must have an overall size and weight rendering it suitable for implantation in subjects without significantly affecting their awake behavior. Microdrives include actuators that position the electrodes coupled to the microdrive. Generally, each electrode is attached to a separate actuator that positions only the electrode attached thereto. Many commercially available prior art microdrives include relatively large actuators designed to position the electrodes during acute recording. Generally speaking, commercially available microdrives (e.g., those available from Thomas Recording GmbH, Germany; FHC Inc., USA; and Narishige Inc., Japan) are too large to be practical for chronic use. Other examples of microdrives that are too large for chronic or semi-chronic recording applications include commercially available microdrives (e.g., the LSS-8000 system produced by GMP, Lausanne, Switzerland) that use very large piezoelectric actuators to position the electrode(s). The size of these piezoelectric actuators limit the use of the such microdrives to acute recording experiments.

Previous work has described mesoscale microdrives designed for autonomous semi-chronic operation, while more recent work aims to apply MEMS technology to create arrays of multi-site electrodes motorized by hydrolysis-based actuators. See, e.g., J. G. Cham et al., "A Semi-Chronic Motorized Microdrive and Control Algorithm for Autonomously Isolating and Maintaining Optimal Extracellular Action Potentials," *J. Neurophysiol.*, 93:570-79 (January 2005); and R. A. Andersen et al., "Cognitive Neural Prosthetics," *Trends in Cog. Sci*, 8(11):486-493 (November 2004).

Miniature actuators often have very small force output, and require special attention to minimize losses in power from, for example, friction due to misalignment. High precision movement is necessary to obtain optimal signal quality, given that action potentials from a typical neuron may be lost by movements as small as a few microns. Gears and lead screws, which are commonly used, often introduce a significant amount of imprecision in the microdrive due to gearing backlash. A relatively long stroke is also needed, because a range of motion of several millimeters, if not centimeters, is often required depending on the depth of the target brain structure, and the accuracy of the implantation procedure. The microdrive must also be able to keep the electrodes stable while subjected to significant stresses and vibrations from the freely moving subject. Further, the size requirement may limit the number of actuators that can be packaged in the microdrive, and the compactness and proximity of all the electrical pathways may increase noise and interference in the neural signal recorded.

Non-traditional manufacturing techniques, such as layered manufacturing, in which parts and mechanisms are "grown" in layers, allow intricate structures to be made with nearly arbitrary geometry and few seams. See, e.g., J. G. Cham et al., "Layered Manufacturing with Embedded Components: Process Planning Issues," *ASME Proc.*, DETC '99, Las Vegas, Nev., (September, 1999); and J. G. Cham et al., "Fast and Robust: Hexapedal Robots via Shape Deposition Manufacturing," *Intl. J. Robotics Res.*, 21(10-11):869-882 (2002). Many of these processes, however, are limited by the bio-incompatibility of the materials available through these processes.

Therefore a need in the art exists for neural prosthetic devices, and in particular, microdrives, suitable for chronic, implantable use. There is a further need in the art for computational technology that can isolate a neural signal originating from a single neuron within a recording containing one or more neural signals. A further need exists for computational technology that can maintain a suitable signal quality of the neural signal isolated in the recordings. A need also exists for computational technologies that may be used in connection with neural interface microdrives capable of positioning electrodes to record signals from active neurons. Similarly, there is a need for computational technologies to actively and autonomously position electrodes during acute recordings. Such technologies may increase the efficiency and/or quality of scientific research and experiments. A need also exists for miniature semi-chronic micro-drives capable of tracking the plasticity (or adaptability) of individual neurons over days and weeks.

BRIEF DESCRIPTION OF THE DRAWINGS

The above-mentioned features and aspects of the present disclosure will become more apparent with reference to the following description taken in conjunction with the accompanying drawings wherein like reference numerals denote like elements. It is intended that the embodiments and figures disclosed herein are to be considered illustrative rather than restrictive.

FIG. 5 shows a set of exemplary signal quality thresholds that may be used to determine actions taken by or transitions between the states of the state machine depicted in FIG. 4. The left column shows the relative values of the thresholds. The right column shows an interpretation of each of the thresholds and an action taken by the state machine depending upon the value of the current signal quality relative to the thresholds.

In FIG. 8(B), the event vectors include about 1.6 ms of the neural signal. The spikes are centered at estimated spike arrival times to illustrate the jitter in the estimated arrival times, especially with respect to low-amplitude spikes.

In FIG. 9, the cluster C1 is the dominant cluster and cluster C2 is a confounding cluster. In this example, because the noise cluster N is centered about the origin of the feature space, selecting the dominant cluster based upon which cluster has the maximum second signal quality metric (e.g., average Peak-to-Peak-Amplitude ("PTPA") for the entire cluster) is equivalent to selecting the dominant cluster based upon which cluster is the furthest from the noise cluster N (or has the greatest Signal-to-Noise Ratio ("SNR").

FIG. 15a shows the initial isolation. The observations of peak-to-peak amplitude at each position are shown in black dots with the final observation in magenta, the average action potential at each position in green, the reconstructed signal quality function in red, and the path of the electrode (always advancing in this example) by the black arrows. The leftmost observation is probably from another neuron, observed before detecting the isolation curve of the isolated neuron. The algorithm stopped at the rightmost position because the signal quality was high enough that further movement was unnecessary and may damage the neuron. FIG. 15b shows the maintenance phase of the isolation. Both the electrode position (blue) and the average peak-to-peak amplitude (red) are plotted against time. At time zero, the neuron is first isolated (which corresponds to the last observation shown in FIG. 15a). The signal improves and then degrades as the neuron drifts by the electrode. The non-horizontal portions of the electrode position graph depict periods during which the autonomous state machine controller attempted to re-isolate the neuron.

Figure 20:
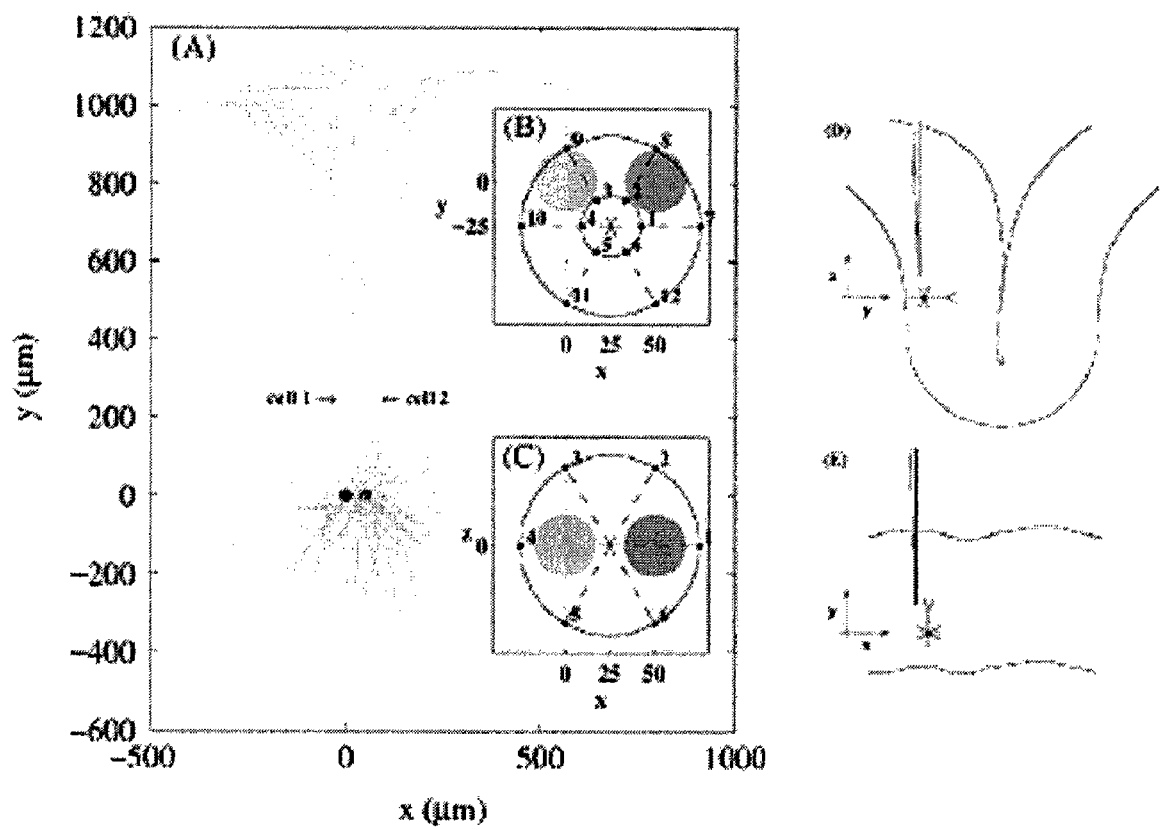
FIG. 20(A) shows a two dimensional projection of two neural cells in a 2-D space.
FIG. 20(B) shows a close-up of the two somata (cell 1 drawn in light gray and cell 2 drawn in dark gray) and a plot of 12 vertical sampling tracks. For illustrative purposes, FIG. 20(B) does not depict dendrites.
FIG. 20(C) shows a close-up of the two somata (cell 1 drawn in light gray and cell 2 drawn in dark gray) and a plot of six horizontal sampling tracks.
FIG. 20(D) depicts a typical recording track traversed by an electrode that records from the bank of the sulcus, where the recording track is perpendicular to the apical dendrite. A local coordinate system is shown to the left of the recording.
FIG. 20(E) depicts a typical track traversed by the recording electrode in a regular cortical layer where the recording track is parallel to the apical dendrite.

for each of the 12 vertical tracks of FIG. 20(B). The data is shown for only successful isolation trials, e.g. the histogram of vertical track V11 normalizes to 84%. The value $\varepsilon=0$ is located next to the dot representing the sampling track. The dendrites of cell 1 and cell 2 are in light and dark gray, respectively. The two axon hillocks are shown as meshed cones adjacent to the somata.

Figure 23:
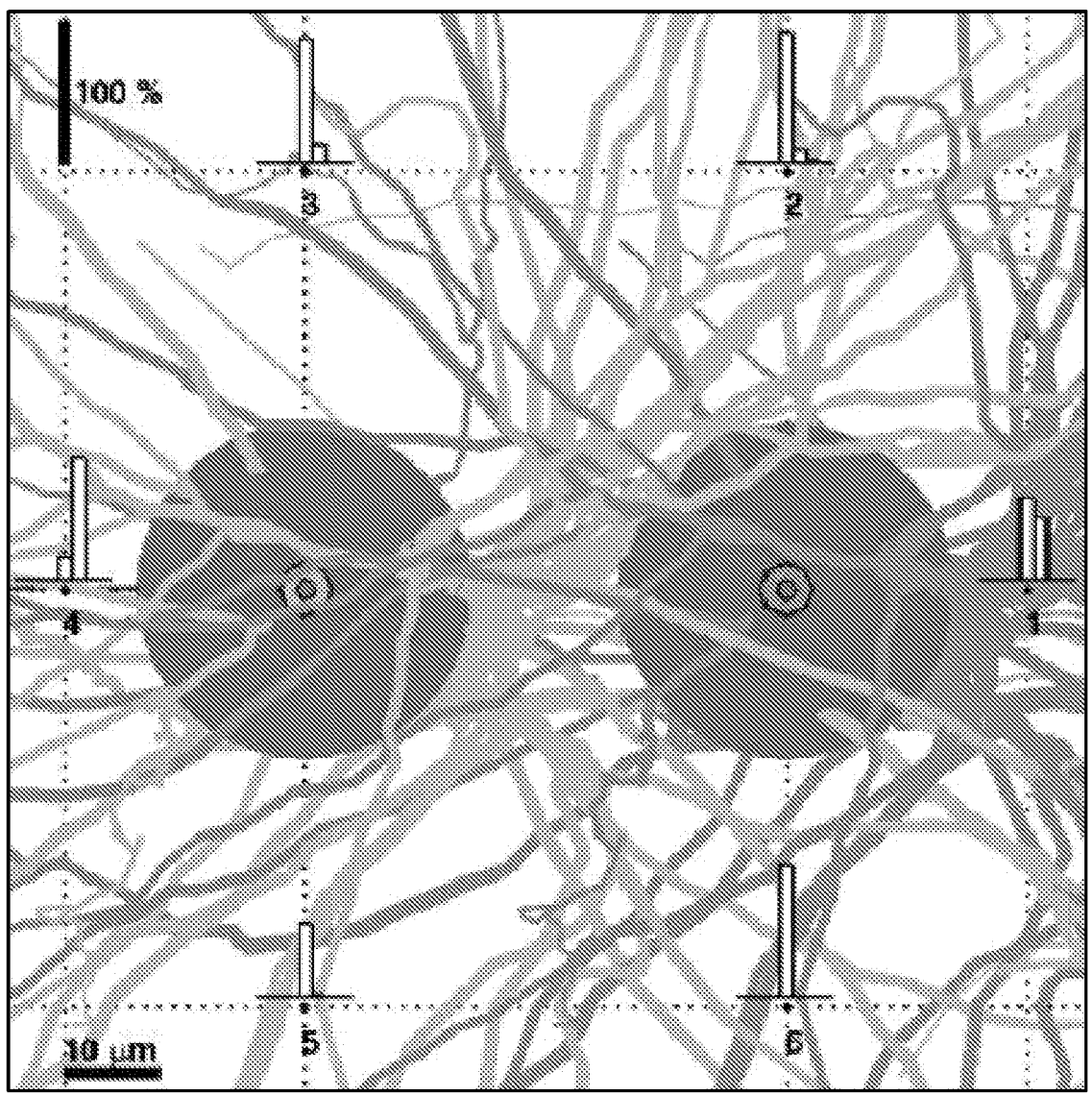

FIG. 23 shows a histogram having a bin size of about 8 μm of error $$\varepsilon \triangleq d_{k^*} - d^*$$

for each of the 6 horizontal tracks of FIG. 20(C). The data is shown for only successful trials. The value $\varepsilon=0$ is located next to the dot representing the sampling track. The dendrites of cell 1 and cell 2 are in light and dark gray, respectively. The axon hillocks are shown as two annular regions in the center of the somata.

Figure 24:
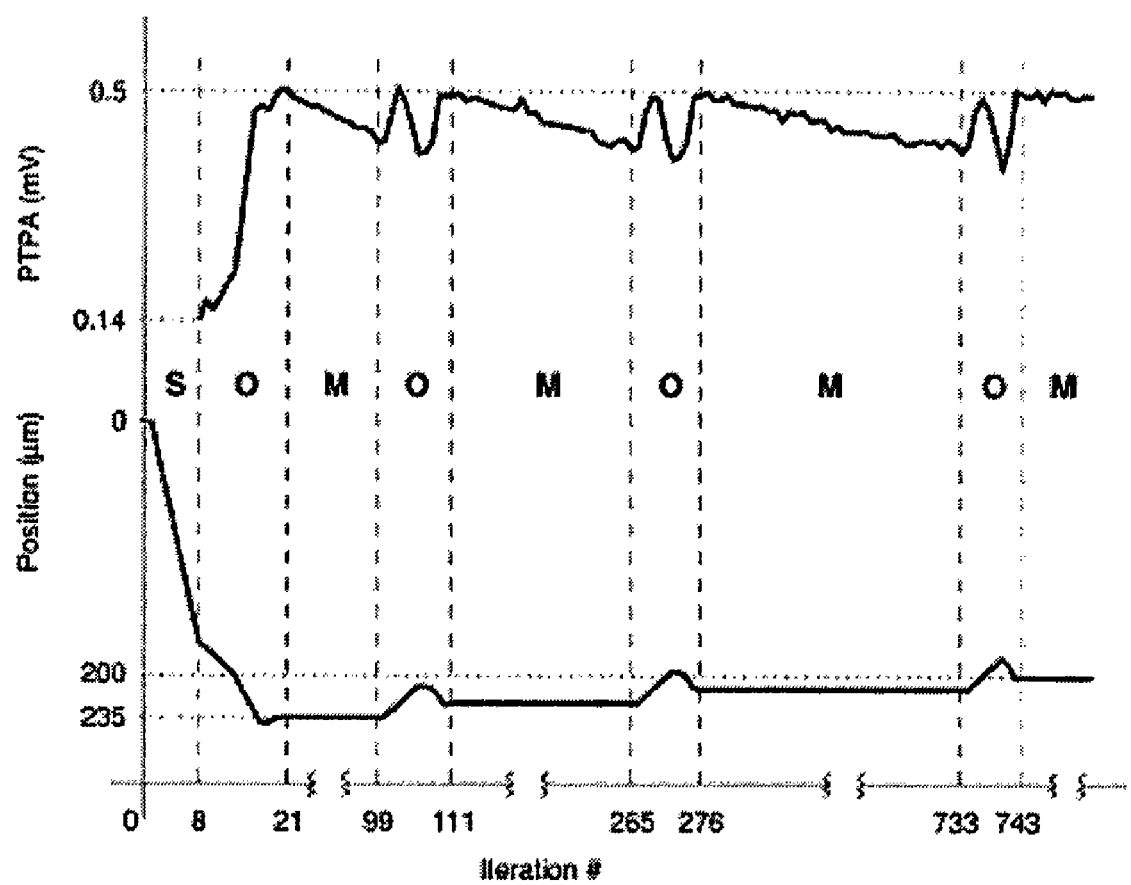

FIG. 24 shows two plots. The top most plot plots the average value of the second signal quality metric (PTPA) over several iterations. Note the drift in the second signal quality metric due to tissue movement. The dashed vertical lines denote the state transitions between the states of the finite state machine depicted in FIG. 7: S corresponds to the Search state; O corresponds to the Optimize state; and M corresponds to the Maintain state. The bottom most plot plots the position (depth) of the "electrode" as a function of iteration number. Despite the drift of the neuron, the objective remains fairly constant (~0.5 mV) at the convergence iterations k=21, 111, 276, 743.

DETAILED DESCRIPTION

The following embodiments and aspects thereof are described and illustrated in conjunction with systems and methods that are meant to be exemplary and illustrative, not limiting in scope. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

The invention is based on the concept of autonomously positioning electrodes within neural tissue to achieve a desired quality of the signal measured by the electrodes. Systems, methods including algorithms, and devices for achieving autonomous positioning of neural recording electrodes are provided in various embodiments of the present invention. As used herein, "autonomous" includes operations that are automatic or machine-controlled or without the continual intervention of a human operator.

An exemplary application of the invention includes positioning one or more electrodes in a location in neural tissue that optimizes and/or improves the recorded signal according to a pre-determined measure of signal quality. In some embodiments, the pre-determined measure of signal quality may be determined by a user. Another exemplary application includes repositioning the electrodes as needed to maintain a pre-determined level of signal quality. The pre-determined level of signal quality may be determined by the user in some embodiments. Without limitation, particular applications of the instant invention include recording neural activity for scientific investigation, recording neural activity for neural prosthetic systems, positioning electrodes for treatment of Parkinson's disease or other neurological impairments, and positioning electrodes to optimize neural stimulation.

The type of signal that is optimized in various embodiments of the invention may include, but is no way limited to, any feature of neural activity, including extracellular action potentials (or "spikes"), local field potentials, any frequency sub-band of the signal, and/or selectivity with respect to a specific type of information, task, or event.

Aspects of the invention include (1) a system 10 (see FIG. 1) for acquiring, recording or storing, and analyzing neural signals, (2) an autonomous electrode positioning algorithm ("autonomous algorithm") 1000 (see FIG. 1), and (3) a microdrive 6000 (see FIG. 11), which, as used herein, is any device capable of positioning one or more electrode(s) 62 with relatively high (e.g., near micron-level) precision. The electrode(s) 62 (see FIG. 1) is/are inserted into the neural tissue of a subject to detect electrical activity ("neural signals") occurring therein.

In one embodiment, the autonomous algorithm 1000 produces a control signal that controls and/or directs one or more actuators 64 (see FIG. 1) to position the electrode(s) 62 within the subject's neural tissue. The control signal is based on the neural signals detected by the electrode(s) 62. The autonomous algorithm 1000 may be implemented with a wide variety of devices in addition to the microdrive 6000, as will be readily appreciated by those of skill in the art. A software implementation of the autonomous algorithm 1000 may, with minimal effort, be used to control the electrodes of these devices and/or microdrive 6000 in a wide variety of experimental, clinical, and therapeutic systems. For example, as new chronic repositionable arrays become available, the autonomous algorithm 1000 may be readily adapted for use in long-term (e.g. years) isolation of neurons and recording of neural signals generated thereby in clinical applications.

The microdrive 6000 may be configured for use with the autonomous algorithm 1000 and/or use as a conventional human-guided microdrive. The microdrive 6000 may be constructed to have an extremely small size that renders it particularly suitable for use in clinical applications. The microdrive 6000 may be used as a "smart" neural implant device that can autonomously optimize neural signals for long-term recordings; that is, robotic microdevices that can autonomously and individually position arrays of electrodes within neural tissue to seek out and continuously optimize signals from neurons. Such autonomously controlled electrodes may have the ability to break out of encapsulation tissue, or move on to other areas to seek better signals.

System 10

Figure 1:
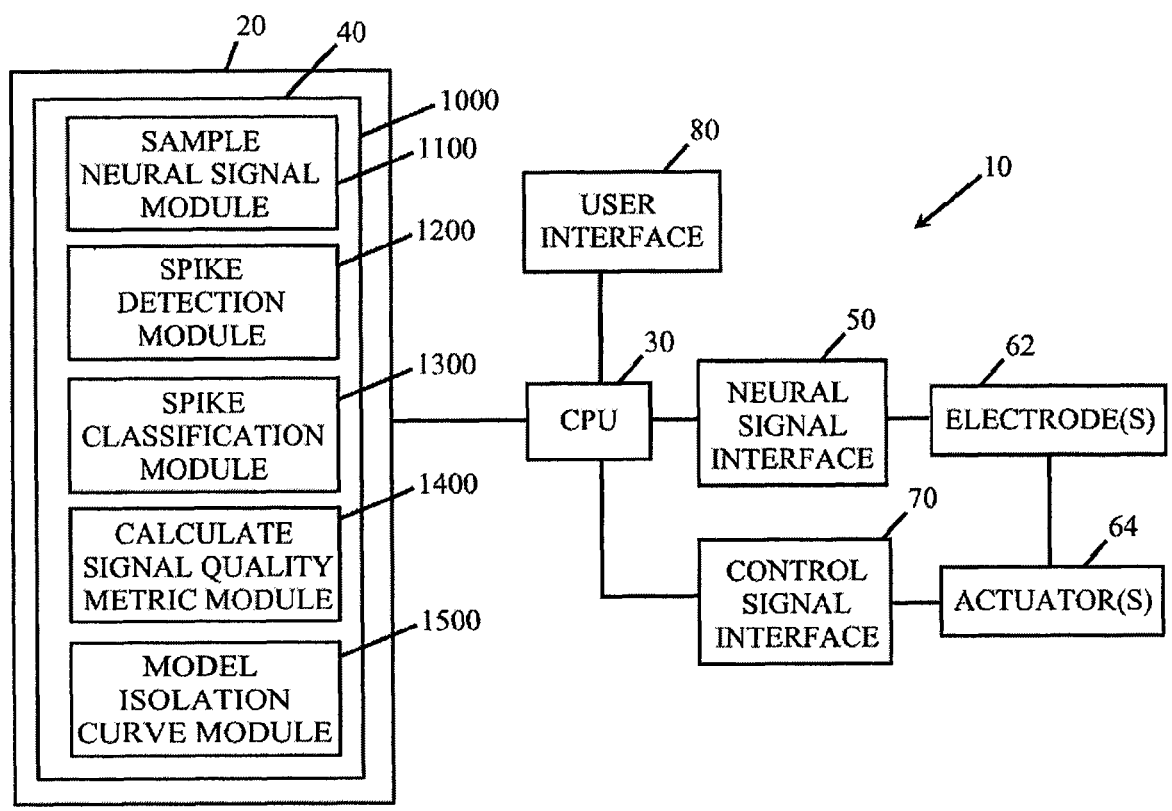
FIG. 1 shows a block diagram illustrating an exemplary autonomous system, in accordance with an embodiment of the present invention.

In one embodiment, as depicted in FIG. 1, the system 10 may include a programmable central processing unit ("CPU") 30 electrically coupled to the electrode(s) 62 by a neural signal interface 50. The CPU 30 may be implemented by any known technology, such as a microprocessor, microcontroller, application-specific integrated circuit (ASIC), digital signal processor (DSP), or the like. The CPU 30 may be integrated into an electrical circuit, such as a conventional circuit board, that supplies power to the CPU 30.

The CPU 30 may be in electrical communication with a memory 20. As is appreciated by those of ordinary skill in the art, the memory 20 may include memory components that are internal or external to the CPU 30. In some embodiments, the memory 20 may be coupled to the CPU 30 by an internal bus.

Optionally, the memory 20 may include external or removable memory devices such as floppy disk drives and optical storage devices (e.g., CD-ROM, R/W CD-ROM, DVD, and the like). The CPU 30 may be coupled to one or more I/O interfaces such as a serial interface (e.g., RS-232, RS-432, and the like), an IEEE-488 interface, a universal serial bus (USB) interface, a parallel interface, and the like, for the communication with removable memory devices such as flash memory drives, external floppy disk drives, and the like.

The memory 20 may comprise random access memory (RAM) and read-only memory (ROM). The memory 20 contains instructions and/or data that control the operation of the CPU 30. The memory 20 may also include a basic input/output system (BIOS), which contains the basic routines that help transfer information between elements of the system 10. The present invention is not limited by the specific hardware component(s) used to implement the CPU 30 or memory 20 of the system 10.

The neural signal interface 50 receives the analog neural signal from the microdrive 60, performs an A/D conversion, and buffers or stores the digitized neural signal for use by the CPU 30. The neural signal interface 50 may store the digitized neural signal in the memory 20 and/or in a separate memory internal to the neural signal interface 50.

The memory 20 may include instructions 40 that are executable by the CPU 30 and implement aspects of the invention. For example, instructions 40 may implement the autonomous algorithm 1000. The instructions 40 may include computer readable software components or modules 1000-1500. As is appreciated by those of ordinary skill in the art, implementing the autonomous algorithm 1000 may require digital and/or analog hardware components, such as an analog to digital converter, amplifiers, filters, and the like and such embodiments are within the scope of the present invention. In one embodiment, some or all of these components may be implemented by the instructions 40.

The instructions 40 implementing the autonomous algorithm 1000 may analyze the digitized neural signals to produce the control signal that directs the actuator(s) 64 to move the electrode(s) 62. The CPU 30 may be coupled to the actuator(s) 64 by a control signal interface 70. The CPU 30 may execute the instructions 40 implementing the autonomous algorithm 1000 and thereby produce the control signal, and subsequently transmit the control signal to the actuators 64 via the control signal interface 70. After receiving the control signal, the actuators 64 may move or reposition the electrode(s) 62.

The CPU 30 may be coupled to a user interface 80 such as a standard computer monitor, LCD, colored lights, or other visual display. The user interface 80 may also include an audio system capable of playing an audible signal. In some embodiments, a display driver may provide an interface between the CPU 30 and the user interface 80.

The user interface 80 may permit the user to enter control commands into the system 10. For example, the user could command the CPU 30 to execute one or more instructions 40 and/or perform portions of the autonomous algorithm 1000. The user interface 80 may include a standard keyboard, mouse, track ball, buttons, touch sensitive screen, wireless user input device, and the like. The user interface 80 may be coupled to the CPU 30 by an internal bus.

Optionally, the CPU 30 may be coupled to an antenna or other signal receiving device such as an optical sensor for receiving a command signal such as a radio frequency (RF) or optical signal from a wireless user interface device such as a remote control. The memory 20 may include software components for interpreting the command signal and executing control commands included in the command signal.

The various components of the system 10 may be coupled together by internal buses and/or cables known in the art for transferring electrical signals between components of the type described. Each of the internal buses of the system 10 may be constructed using a data bus, control bus, power bus, I/O bus, and the like.

In one embodiment, the CPU 30, memory 20, neural signal interface 50, control signal interface 70, actuator(s) 64, and electrode(s) 62 of the system 10 are components of the microdrive 6000. Optionally, the user interface 80 may reside in the microdrive 6000. In this embodiment, the microdrive 6000 may be used as an autonomous chronic multi-electrode implant for detecting neural signals. The neural signals may be used to control or provide input to an external device such as a neural prosthetic.

Figure 2:
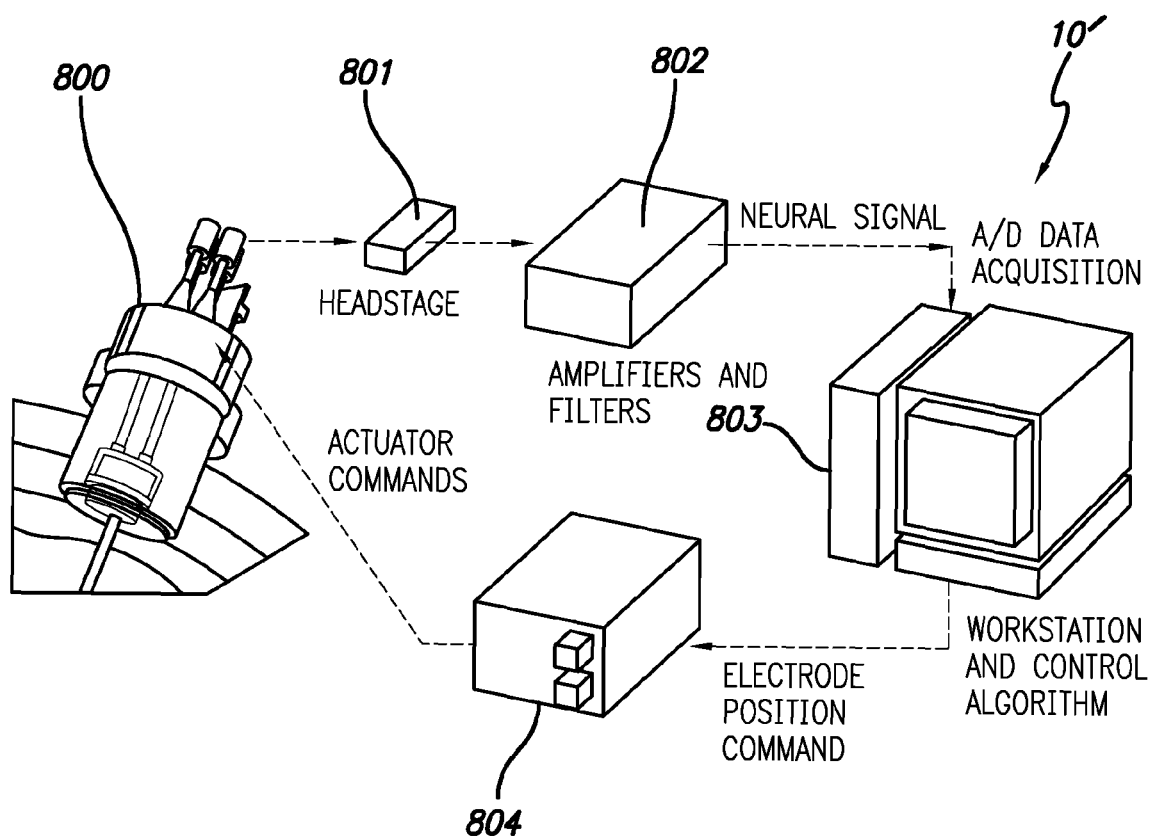
FIG. 2 shows a system diagram illustrating an alternate embodiment of the system of FIG. 1.

In an alternate embodiment of the system 10, a system 10' depicted in FIG. 2, the CPU 30 and memory 20 reside in a workstation 803. The instructions 40 stored in the memory 20 may include the computer executable instructions for MATLAB (available from Mathworks Inc., USA) and the instructions 40 implementing the autonomous algorithm 1000 may include files, e.g. m-files, executable by MATLAB.

The CPU 30 is coupled to the microdrive 6000' by neural signal interface 50'. The neural signal interface 50' may include a headstage amplifier 801 that is itself in electronic communication with other various amplifiers and filters 802 that amplify and filter the neural signal detected by the electrode(s) 62'. The neural signal interface 50' may include a data acquisition card (not shown) capable of receiving the analog neural signal from the electrode(s) 62' of the microdrive 6000', performing an A/D conversion, and buffering or storing the digitized signal for use by the CPU 30. In one embodiment, the data acquisition card stores the digitized neural signal in the memory 20. In another embodiment, the data acquisition card stores the digitized neural signal in onboard memory accessible by the CPU 30. An example of a suitable data acquisition card for use with system 10 may be obtained from National Instruments Inc., USA.

The instructions 40 implementing the autonomous algorithm 1000 may analyze the digitized neural signals to produce the control signal that directs the actuators 64' of the microdrive 6000' to move the electrode(s) 62'. The CPU 30 of the workstation 803 may be coupled to the actuators 64' of the microdrive 6000' by a control signal interface 70'. The control signal interface 70' may include an actuator controller 804 that issues motor commands to the actuators 64' of the microdrive 6000' that direct the actuators 64' to reposition the electrode(s) 62'. An example of a suitable actuator controller for use with system 10 may be obtained from Klocke Nanotechnik, Germany, part NWC.

Autonomous Algorithm 1000

Overview

The autonomous algorithm 1000 may include a Sample Neural Signal Module 1100 for receiving one or more signals detected by the electrode(s) 62 and recording or storing the signal(s) in the memory 20. Typically, the Sample Neural Signal Module 1100 will record a separate signal for each of the electrode(s) 62. The signal received from each electrode 62 may be stored for a predetermined duration. In one embodiment, the predetermined duration is approximately 20 seconds.

A significant problem may occur if the firing rate of a neuron being isolated is intermittent, or the neuron stops firing altogether, especially in the presence of other nearby neurons. Such situations can create extreme outliers in sampling that can confound the neuron isolation portion of the autonomous algorithm 1000. This eventuality may be remedied by increasing the recording time at each sample. Setting the predetermined duration equal to approximately 20 seconds may allow activity from intermittent firing neurons to be captured consistently.

The Sample Neural Signal Module 1100 may be executed more than once and each time it is executed, a separate signal for each of the electrode(s) 62 may be received and stored. For example, each time the position of the electrode(s) 62 within the neural tissue is/are changed, the Sample Neural Signal Module 1100 may be executed. For example, if the system 10 includes three electrodes 62 and all of the electrodes 62 are positioned three times, the Sample Neural Signal Module 1100 may record nine separate signals. As used herein, the term "sample" refers to a signal received from a single electrode 62 and stored by the Sample Neural Signal Module 1100. Consequently, referring to previous example, nine samples were collected, three for each electrode 62. An example of a sample collected may be viewed in FIG. 14*a*.

The action potentials of the neurons may appear as spikes in the sampled extracellular signal. Numerous spikes appear in the example sample depicted in FIG. 14*a*. These spikes may correspond to the action potentials of one or more neurons. Therefore, signal processing techniques may be used to analyze the sample and group the spikes into groups representing separate neurons. The analysis may include detecting the spikes, grouping or clustering the detected spikes by the neuron producing them, and determining the quality of the signal received from each of the neurons. The quality of the signal received from each of the neurons may be measured using each signal's peak-to-peak amplitude ("PTPA"). Alternatively, the quality may be judged by the amount of isolation (as measured in principle component space) between a particular neuron's signal and the signal of other neurons and/or background noise. As is appreciated but those of ordinary skill, many other choices of signal quality may be used and are within the scope of the present invention. The signal quality of the neurons may be compared to determine a dominant neuron. The dominant neuron may be the neuron from which the highest quality signal is received. Spikes generated by other neurons may be ignored.

After the dominant neuron is identified, the electrode 62 may be moved or repositioned relative to the neuron, and the Sample Neural Signal Module 1100 used to capture one or more additional samples. After a sufficient number of samples are collected, the signal quality of the dominant neuron for each electrode 62 position may be used to estimate or model an isolation curve. The modeled isolation curve models the signal quality along the path of travel of the electrode 62. In some embodiments, the actuators(s) 64 position the electrode(s) 62 linearly in the vertical direction. In other words, the actuators(s) 64 determine the depth of the electrode(s) 62 in the neural tissue.

Figure 3:
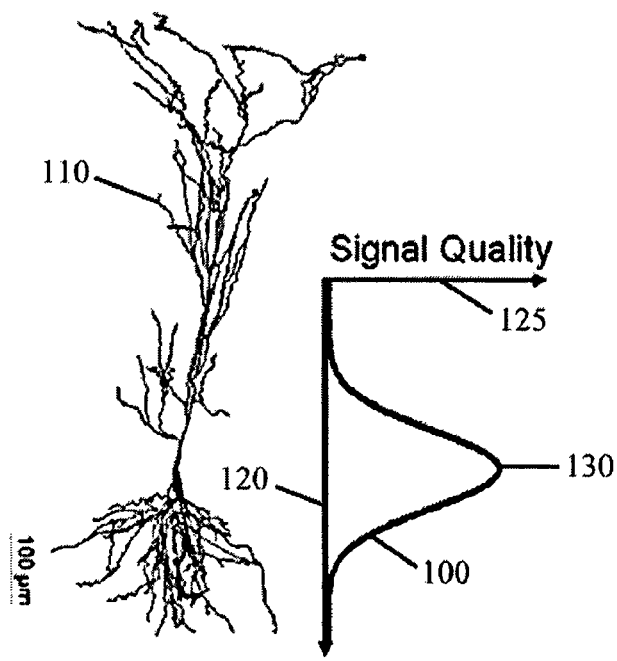
FIG. 3 shows an illustration of a rat pyramidal neuron in accordance with an embodiment of the present invention and based on morphology described in G. Buzsaki and D. Turner, "Dendritic properties of hippocampal CAI pyramidal neurons in the rat: Intracellular staining in vivo and in vitro," *J. Comp. Neurol.*, 391:335-52 (1998). The graph to the right of the neuron illustrates an idealized plot of signal quality (i.e., idealized isolation curve) as observed by an electrode as it passes the soma, the location where extracellular action potentials are primarily generated.

Referring to FIG. 3, an exemplary ideal isolation curve 100 is provided. The leftmost portion of FIG. 3 shows an illustration of a rat pyramidal neuron 110 based on morphology described in G. Buzsaki and D. Turner, "Dendritic properties of hippocampal CAI pyramidal neurons in the rat: Intracellular staining in vivo and in vitro," *J. Comp. Neurol.*, 391:335-52 (1998). The ideal isolation curve 100 to the right of the neuron 110 illustrates the idealized signal quality observed by an electrode traveling in the direction indicated by arrow 120 alongside the neuron 110. Signal quality increases in the direction of arrow 125. The ideal isolation curve 100 may have a maximum 130 near a location of the neuron 110 where the action potential is initiated.

While the ideal isolation curve 100 may not be available, as described below, it can be modeled from observed signal quality values. The modeled isolation curve may be used to determine a position that improves and/or optimizes received signal quality. The electrode 62 may then be moved to that position and the signal quality reevaluated. After the electrode 62 is located at a satisfactory position, the autonomous algorithm 1000 may provide instructions for repositioning the electrode(s) 62 to maintain a satisfactory level of signal quality.

State Machine

Figure 4:
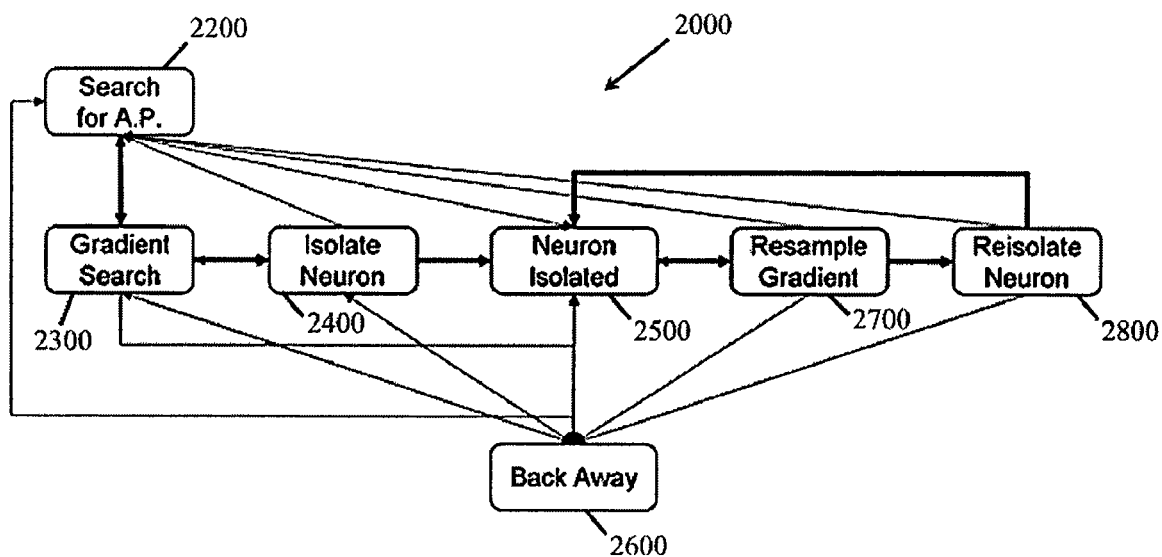
FIG. 4 shows an exemplary embodiment of a finite state machine corresponding to an algorithm, in accordance with an embodiment of the present invention. Each state is represented by a box and lines connecting the states show all possible transitions. The simplest path between the states during an exemplary isolation of a neuron is shown by the thick (i.e., bolded) arrows.

Referring to FIG. 4, the autonomous algorithm 1000 may be described with respect to a supervisory control state machine 2000. The state machine 2000 may include seven states: Search for Action Potentials state 2200, Gradient Search state 2300, Isolate Neuron state 2400, Neuron Isolated state 2500, Back Away state 2600, Resample Gradient state 2700, and Reisolate Neuron state 2800. Transitions between the states 2200-2800 are indicated by arrows between the states. To avoid confusion, this state machine 2000 will be described with respect to an embodiment of the invention having a single electrode 62. However, as is apparent to those of ordinary skill, embodiments with more than one electrode are within the scope of the present invention. The autonomous algorithm 1000 may be executed with respect to each electrode 62 and the state of each electrode 62 determined separately.

The state machine 2000 governs the transitions between states 2200, 2300, 2400, 2500, 2600, 2700, and 2800. To avoid unexpected behavior arising from an overly complex state machine, the relatively "simple" state machine 2000 may be used. However, it is apparent to those of ordinary skill in the art that the autonomous algorithm 1000 may be implemented using a more complex state machine and such embodiments are within the scope of the present invention. As is also apparent to those of ordinary skill, whenever the state machine 2000 commands a "non-optimal" movement of the electrode 62 (i.e., a movement that an experienced operator would not command and/or movement that does not lead to isolating a neuron), an adjustment may be made to either a parameter or statistical test in one or more of the transitions of the state machine 2000, a new transition may be added between two existing states, and/or a new state may be added.

A typical path through the state machine 2000 will now be described (the path described is highlighted in FIG. 4). In one embodiment, when the autonomous algorithm 1000 begins, the electrode 62 is initially and roughly placed in a region of neural tissue that is of interest. In an alternate embodiment, an optional Move to Target Depth state (not shown) can be used to place the electrode 62 within the region of neural tissue of interest. Such a state may be useful, for example, when pre-operative imaging (such as with an MRI machine) suggests a specific neural structure and its specific location, or target depth, for optimal recording. After the electrode 62 is placed within the region of interest, the autonomous algorithm 1000 may begin in the Search for Action Potentials state 2200.

Search for Action Potentials State 2200

In the Search for Action Potentials state 2200, the Sample Neural Signal Module 1100 (described above) may be used to receive noisy neural signal(s) from the electrode 62 and record the noisy neural signal(s) in the memory 20. The Sample Neural Signal Module 1100 may record noisy neural signal(s) over a predetermined duration and call a Spike Detection Module 1200 to analyze the recorded noisy neural signal(s).

The Spike Detection Module 1200 may determine whether action potentials have been detected by the electrode 62. The electrode 62 may be moved in steps of a predetermined distance "$\Delta_S$" until action potentials are detected. In one embodiment, the electrode 62 is moved at about 4 μm/s. In one embodiment, the predetermined distance "$\Delta_s$" may be about 10 microns to about 50 microns. The predetermined distance "$\Delta_S$" may be selected by the user. In one embodiment, the user selects the predetermined distance "$\Delta_S$" from a list of step sizes including 10, 20, 30, 40, and 50 microns. The Spike Detection Module 1200 may consider action potentials to be detected if the frequency of the spikes detected exceeds a minimum firing rate (e.g., about 1.5 Hz, 2 Hz, or 2.5 Hz). After action potentials are detected, the state machine 2000 transitions to the Gradient Search state 2300.

Gradient Search State 2300

In the Gradient Search state 2300, the electrode 62 may be advanced in steps of a predetermined distance (e.g., about 5, 10, 15, 20, 25 or 30 microns), and the Sample Neural Signal Module 1100 used to obtain sample(s) of the noisy neural signal(s) at each step. After each step, for each sample, the Spike Detection Module 1200 may be used to detect action potentials in the sample collected by the electrode 62 at that step. If the firing rate drops below the minimum firing rate, the signal may be sampled at that position one more time. If the firing rate remains below the minimum firing rate, the state machine 2000 may determine the neuron is lost and transition to the Search for Action Potentials state 2200.

After a predetermined number of steps, a Spike Classification Module 1300 may be used to classify the action potentials into classes corresponding to distinct neurons or noise. In other words, the Spike Classification Module 1300 may help to separate and identify the action potentials arising from distinct neurons. In one embodiment, the predetermined number of steps is five.

Because it may be desirable to isolate the dominant neuron and ignore the others, if the number of classes corresponding to neurons is greater than one, i.e., action potentials from more than one neuron were detected by a single electrode, the dominant neuron must be identified. A current signal quality metric may be determined using a Calculate Signal Quality Metric Module 1400 and used to compare the signal quality of the classes corresponding to neurons. The current signal quality metric may be used to identify the class with the best signal qualities. The current signal quality metric of each class may include the greatest signal-to-noise ratio ("SNR") observed for each class. A dominant class within the sample may be the class having the greatest current signal quality metric. The action potentials of the dominant class are generated by the dominant neuron.

The current signal quality metric may be compared to various threshold values and used to determine the transitions between two or more of the states of the state machine 2000. FIG. 5 depicts an exemplary set of threshold values that may be used to determine the transitions between two or more of the states of the state machine 2000: "MIN_TRACK_SNR," "MIN_SNR," "STOP_SNR," and "MAX_SNR." In various embodiments, each of these threshold values may be selected by the operator. In one embodiment, as a non-limiting example, the "MIN_TRACK_SNR" may be set equal to 2, "MIN_SNR" may be set equal to 6, "STOP_SNR" may be set equal to 8, and "MAX_SNR" may be set equal to 12.

A second signal quality metric may be determined using the Calculate Signal Quality Metric Module 1400 and used by the Model Isolation Curve Module 1500 to model an isolation curve of the dominant neuron. In some embodiments, the second signal quality metric includes the peak-to-peak amplitude ("PTPA") of the action potentials of the dominant class. The PTPA of the action potentials of the dominant class may be average to provide a representative PTPA for the dominant class. The modeled isolation curve is an estimate of the signal quality along a linear path of travel of the electrode 62 near the dominant neuron. As described below, the isolation curve may be modeled as a polynomial equation. The Model Isolation Curve Module 1500 may calculate a most likely order of the isolation curve.

If the most likely order of the isolation curve is greater than zero (i.e., the isolation curve is at least a sloped line), then a statistically significant gradient has been found. If not, the electrode 62 may continue to be advanced in steps of the predetermined distance (e.g., about 5, 10, 15, 20, 25 or 30 microns). At each step, noisy neural signals may be sampled using the Sample Neural Signal Module 1100 and analyzed by the Spike Detection Module 1200, Spike Classification Module 1300, Calculate Signal Quality Metric Module 1400, and Model Isolation Curve Module 1500 until a statistically significant gradient is detected.

After the statistically significant gradient is detected, the electrode 62 may be considered to be on the isolation curve of the dominant neuron and the state machine 2000 may transition to the Isolate Neuron state 2400. In some embodiments, the state machine 2000 may transition to the Isolate Neuron state 2400 only if the signal quality metric is above the predetermined lower signal quality threshold "MIN_TRACK_SNR," below which the measurements of signal quality may be considered unreliable.

Isolate Neuron State 2400

Figure 6:
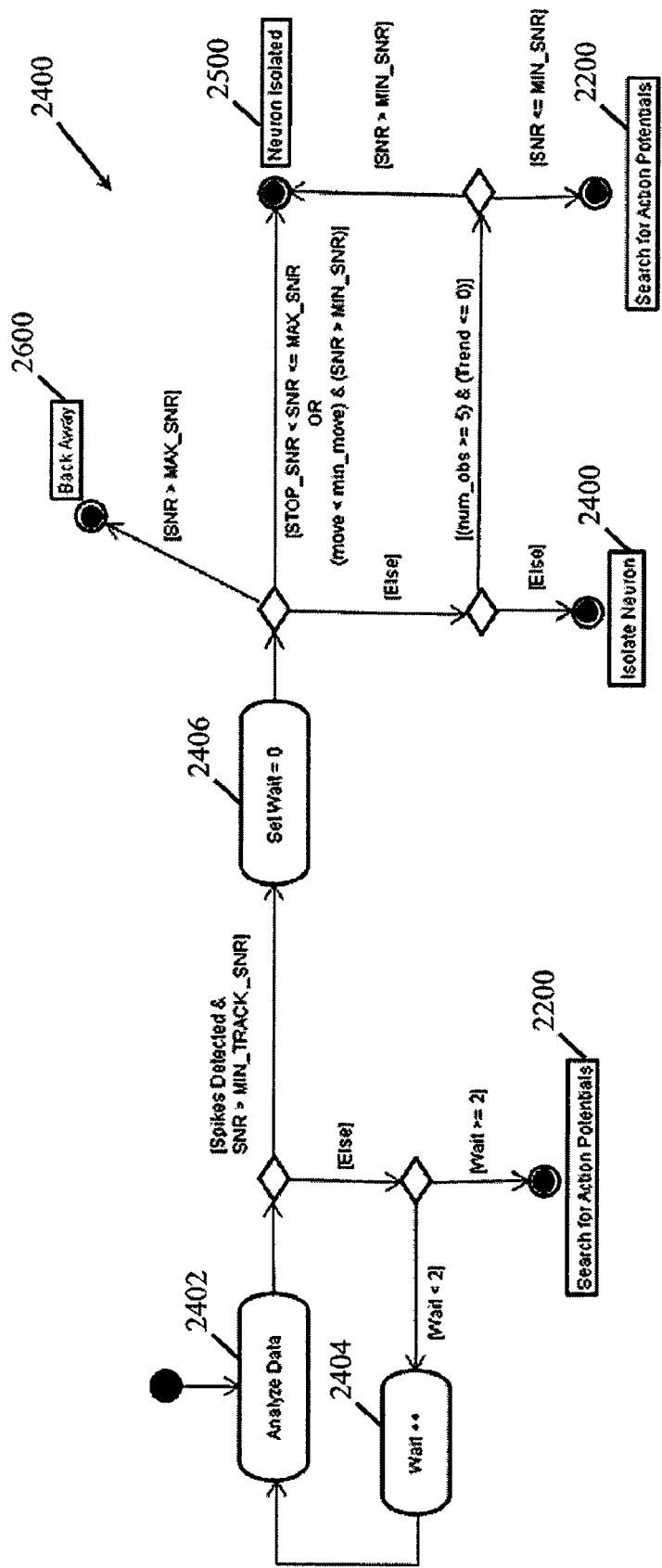
FIG. 6 shows an activity diagram for the Isolate Neuron state of the finite state machine of FIG. 4. The activity diagram begins at the solid circle located at the top left of the figure. Test junctions are illustrated as diamonds, test results are shown in brackets, and state transitions are shown by ringed circles with the name of the new state provided in a box next to each of the ringed circles.

Referring to FIG. 6, an activity diagram depicting one embodiment of the internal logic of the Isolate Neuron state 2400 is provided. Upon transitioning into the Isolate Neuron state 2400, a variable "Wait" may be initialized to zero. In this state, the electrode 62 may not be moved using a constant step size. Instead, the electrode 62 may be moved according to a varying step size calculated from the modeled isolation curve by the Model Isolation Curve Module 1500. In a block 2402, an improved and/or optimum position of the single electrode 62 is estimated from the modeled isolation curve and a variable "move" is set equal to the distance the electrode must move from its current position to be located in the estimated optimum position.

After the electrode 62 is moved, i.e., advanced or withdrawn, the noisy neural signals in the new position are sampled using the Sample Neural Signal Module 1100 and analyzed by the Spike Detection Module 1200, Spike Classification Module 1300, and new current and/or second signal quality metrics may be calculated using the Calculate Signal Quality Metric Module 1400. The Model Isolation Curve Module 1500 may be used to modify or remodel the isolation curve based on the newly available data. As described below, the Model Isolation Curve Module may use a Bayesian model selection criteria to select the lowest order model that statistically fits the available data. This approach may provide a reliable means of estimating the local shape of the isolation curve from the noisy data. In one non-limiting embodiment, the modeled isolation curve is selected from a class of polynomials.

A variable "Trend" may provide a measure of the current trend of the values of the signal quality metrics of the action potentials. Knowledge of the signal quality trend may help reduce or eliminate improper movements of the electrode. The trend may be determined by comparing the new signal quality metric to one or more previously calculated signal quality metrics for the neuron. If the new signal quality metric is greater than the previously calculated signal quality metrics, i.e., the variable "Trend" is greater than zero, an upward trend may have been observed. On the other hand, if the new signal quality metric is less than the previously calculated signal quality metrics, i.e., the variable "Trend" is less than zero, a downward trend may have been observed. It is apparent to those of ordinary skill that the variable "Trend" may also be determined from the slope of the isolation curve near or at the current the position of the electrode 62.

If the current signal quality metric is less than or equal to a predetermined minimum threshold of signal quality "MIN_TRACK_SNR" (see FIG. 5) and the variable "Wait" is less than a predetermined number, the variable "Wait" may be incremented at a block 2404 and the state machine 2000 may transition to the block 2402. If the variable "Wait" is greater than or equal to the predetermined number, the neuron being isolated may be considered lost (e.g., it has drifted away, become inactive or has been damaged by the electrode) and the state machine 2000 may transition to the Search for Action Potentials state 2200. The predetermined number may include two, three, four, five, etc. In other words, if the current signal quality is too low, the state machine 2000 will resample the neural signal the predetermined number of times before transitioning states.

Optionally, if the firing rate drops below the minimum firing rate, the signal may be sampled at that position one more time. If the firing rate remains below the minimum firing rate, the state machine 2000 determines the neuron is lost and transitions to the Search for Action Potentials state 2200.

If the signal quality metric is above the threshold "MIN_TRACK_SNR," the variable "Wait" may be reset, e.g., the variable "Wait" may be set equal to zero, at a block 2406. If the signal quality metric is greater than the threshold "MAX_SNR," the state machine 2000 may transition to the Back Away state 2600. On the other hand, if the signal quality metric is less than or equal to the threshold "MAX_SNR," the variable "move" may be compared to a predetermined threshold "MIN_MOVE." In various embodiments, the value of the threshold "MIN_MOVE" may be selected by the operator. In one non-limiting embodiment, the threshold "MIN_MOVE" may be set equal to approximately 5 microns.

If the variable "move" is less than "MIN_MOVE," the top or maximum of the isolation curve may be considered to have been reached. If the variable "move" is less than "MIN_MOVE" and the signal quality metric is greater than the threshold "MIN_SNR" (see FIG. 6), i.e., ((move<MIN_MOVE) & (SNR>MIN_SNR)), the signal quality metric at the maximum of the isolation curve is considered acceptable and the state machine 2000 transitions to the Neuron Isolated state 2500. Alternatively, the state machine 2000 may transition to the Neuron Isolated state 2500 if the signal quality metric is greater than the threshold "STOP_SNR" and less than or equal to the threshold "MAX_SNR."

If after a predetermined number of samples (each corresponding to an electrode position), e.g., (num_obs$\geq$5), the signal quality is showing a consistent downward trend (Trend$\leq$0) and signal quality metric is less than or equal to the threshold "MAX_SNR," neuron drift and/or electrode/tissue coupling or the like may be interfering with the isolation process. Such interference may render the modeled isolation curve unreliable. In the embodiment depicted in the drawings, the predetermined number of observations (or steps) is five. However, as is appreciated by those of ordinary skill in the art, the predetermined number of observations may include any other desired number of observations. Even if something is interfering with isolating the neural signal, i.e., ((num_obs$\geq$5) & (Trend$\leq$0)), the state machine 2000 may transition to the Neuron Isolated state 2500 if the signal quality metric exceeds the threshold "MIN_SNR," i.e., (SNR>MIN_SNR). Otherwise, if the signal quality metric is less than or equal to the threshold "MIN_SNR," i.e., (SNR$\leq$MIN_SNR), the neuron may be deemed too far from the line of travel of the electrode 62 to be isolated and the state machine 2000 may transition to the Search for Action Potentials state 2200 to search for another neuron to isolate.

On the other hand, if the signal quality is showing a consistent upward trend, i.e., (Trend>0), or the number of observations is fewer than the predetermined number of observations, e.g., (num_obs<5), the maximum of the isolation curve may not yet be reached. Under these circumstances, if the signal quality metric is not yet too high to fear neuron damage by continued movement, i.e., signal quality metric is less than or equal to the threshold "MAX_SNR," the state machine 2000 may self-transition to the Isolate Neuron state 2400 to continue the optimization.

Neuron Isolated State 2500

In the Neuron Isolated state 2500, the electrode 62 may be held stationary and the signal quality monitored periodically and/or continuously. The current signal quality metric may be determined by sampling the noisy neural signals using the Sample Neural Signal Module 1100 and analyzing the noisy neural signals using the Spike Detection Module 1200, Spike Classification Module 1300, and Calculate Signal Quality Metric Module 1400. [Optionally, the Model Isolation Curve Module 1500 may also be used to modify or remodel the isolation curve.

The signal quality may degrade if tissue drift causes the isolated neuron to move away from the electrode 62 detecting the neural signal of the isolated neuron. When the current signal quality metric drops below a predetermined threshold (e.g., 90% of its greatest level or the threshold "MIN_SNR"), the state machine 2000 may transition to the Resample Gradient state 2700.

Resample Gradient State 2700

In the Resample Gradient state 2700, the autonomous algorithm 1000 tries to re-isolate the neuron. The internal logic of the Resample Gradient state 2700 may be substantially similar to the internal logic of the Gradient Search state 2300 discussed above. However, the electrode(s) 62 may be advanced in steps of a smaller predetermined distance (e.g., about 3, 5 or 7 microns). The predetermined distance may be determined by the characteristics of the neural tissue in which the electrode operates. As is apparent to one skilled in the art, the size and/or packing density of neurons located in different parts of the cortex may vary. Therefore, it may be desirable to consider the size of the neurons and/or the neural packing density in the area of interest when selecting the predetermined distance.

After the statistically significant gradient is re-detected, the state machine 2000 transitions to the Reisolate Neuron state 2800.

Reisolate Neuron State 2800

The internal logic of the Reisolate Neuron state 2800 may be substantially similar to the internal logic of the Isolate Neuron state 2400. In some embodiments, the value of the threshold "MIN_SNR" used by the Reisolate Neuron state 2800 may be set to 90% of the value of the threshold "MIN_SNR" used by the Isolate Neuron state 2400. If the dominant neuron starts to drift away from the electrode 62, current signal quality metric may be lower than the current signal quality metric realized during the initial isolation. Using the same threshold "MIN_SNR" value in both the Reisolate Neuron state 2800 and Isolate Neuron state 2400 may make reisolation of the dominant neuron difficult because the current signal quality metric may fall below the threshold "MIN_SNR" triggering the state machine 2000 to transition to the Search for Action Potentials state 2200 instead of attempting to reisolate the previously isolated neuron. Because it may be desirable to continue tracking the previously isolated neuron, the threshold "MIN_SNR" value used by the Reisolate Neuron state 2800 may be lowered to slightly below the threshold "MIN_SNR" value used by the Isolate Neuron state 2400.

If the neuron is successfully reisolated, the state machine 2000 may transition to the Neuron Isolated state 2500. Otherwise, the state machine 2000 may transition to the Search for Action Potentials state 2200.

If, while in any state, the signal quality metric is greater than the threshold "MAX_SNR," the state machine 2000 may transition to the Back Away state 2600 and the electrode 62 may be retracted a predetermined distance (e.g., about 5, 10, 15, 20, 25 or 30 microns) to avoid damaging the neuron. After retracting the electrode, the Back Away state 2600 may assess the current signal quality metric by sampling the noisy neural signal using the Sample Neural Signal Module 1100 and analyzing the noisy neural signal using the Spike Detection Module 1200, Spike Classification Module 1300, and Calculate Signal Quality Metric Module 1400. The Back Away state 2600 will then transition to one of the three states, the Gradient Search state 2300, the Isolate Neuron state 2400, or the Neuron Isolated state 2500 depending upon the value of the current signal quality metric. In one non-limiting embodiment, if the current signal quality metric is less than the threshold "MIN_TRACK_SNR," the state machine 2000 may transition to the Gradient Search State 2300. On the other hand, if the current signal quality metric is greater than the threshold "MIN_TRACK_SNR," but less than the threshold "STOP_SNR," the state machine 2000 may transition to the Isolate Neuron state 2400. Finally, if the value of the current signal quality metric is greater than the threshold "STOP_SNR," the state machine 2000 may transition to the Neuron Isolated state 2500.

Alternate Embodiment of the State Machine

Figure 7:
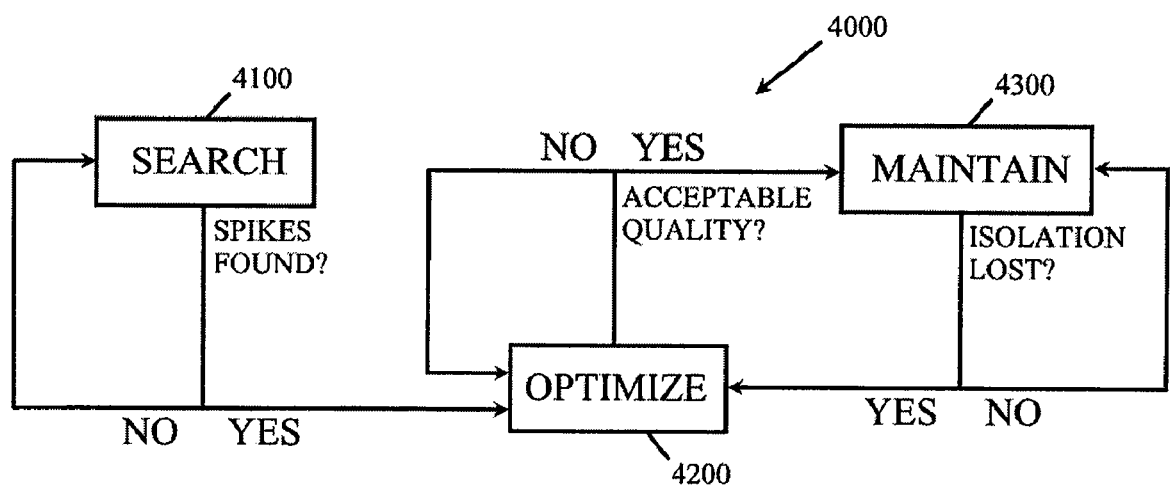
FIG. 7 shows an alternate embodiment of the finite state machine of FIG. 4. Each state is represented by a box and lines connecting the states show all possible transitions.

An alternate embodiment of the state machine 4000 may be viewed in FIG. 7. The states are represented by boxes and the state transitions are denoted by arrows. A search state 4100 may perform spike detection and spike classification. The remaining states, of the state machine 4000 may sample neural signals for a short period of time and performs a more complete analysis of the data (e.g., spike detection, classification, and/or signal quality calculation).

In this embodiment, the state machine 4000 includes only three states: a Search state 4100, an Optimize state 4200, and a Maintain state 4300. In the Search state 4100, the electrode 62 may be moved with the predetermined distance $\Delta_S$. The distance $\Delta_S$ may be chosen by the user. The state machine 4000 remains in the Search state 4100 (by virtue of self-transitions) until spikes are detected, which triggers the transition to the Optimize state 4200. The Search state 4100 may include the functionality of the Search for Action Potentials state 2200 described above. In other words, the Search state 4100, searches for action potentials. The state machine 4000 may transition from the Search state 4100 to the Optimize state 4200 for the same reasons the Search for Action Potentials state 2200 transitions to the Gradient Search state 2300, i.e., action potentials are detected.

In the Optimize state 4200, the electrode 62 is moved according to the variable "move" calculated by the Model Isolation Curve Module 1500 described in greater detail below. The Optimize state 4200 may include the functionality of the Gradient Search state 2300, Isolate Neuron state 2400, Resample Gradient state 2700, and Reisolate Neuron state 2800. In other words, the Optimize state 4200 determines whether the autonomous algorithm 1000 is on the isolation curve of the dominant neuron, models the isolation curve, and may move the electrode 62 to improve and/or optimize signal quality based on the modeled isolation curve and additional signal samples. The state machine 4000 remains in the Optimize state 4200 until acceptable signal quality is attained (e.g., until the maximum of the signal quality metric is found), at which point the state machine 4000 transitions to the Maintain state 4300. The Optimize state 4200 may transition to the Maintain state 4300 for the same reasons the Isolate Neuron state 2400 transitions to the Neuron Isolated state 2500. The Optimize state 4200 may also transition to the Maintain state 4300 for the same reasons the Reisolate Neuron state 2800 transitions to the Neuron Isolated state 2500.

In the Maintain state 4300, the electrode 62 is not moved. The Maintain state 4300 may include the functionality of the Neuron Isolated state 2500. The Maintain state 4300 may transition back to the Optimize state 4200 for the same reasons the Neuron Isolated state 2500 transitions to the Resample Gradient state 2700. At this state, the autonomous algorithm 1000 checks for the signal quality variations without moving the electrode 62. If these variations exceed some pre-specified tolerance, the optimality is considered lost, and the state machine 4000 transitions back to the Optimize state 4200.

The modules introduced above will now be described.

Spike Detection Module 1200

The Spike Detection Module 1200 may detect the presence of distinct spikes in a noisy neural signal, estimate the spike arrival time for each spike, and extract a segment (typically about 1.5 ms to about 2.0 ms or about 0.5 ms to about 1.0 ms) from the neural signal centered at the spike arrival time. These signal segments are referred to hereafter as "event vectors."

Because of its practical importance to experimental neuroscience, the detection of spikes in noisy data is a classic problem. Spike detection methods may be classified as manual and automated, supervised and unsupervised. The Spike Detection Module 1200 of the autonomous algorithm 1000 may use a spike detection method that is automated and unsupervised.

The simplest manual detection method is the window discriminator. See J. Welsh et al., "Multielectrode recording from the cerebellum," *Methods for Neural Ensemble Recordings*, 5:79-100 (M. Nicolelis, Ed.; Boca Raton: CRC Press, 1999). Other methods include amplitude detection, power detection, matched filtering, principal components and Haar transformation. See M. Sahani, "Latent variable models for neural data analysis," Ph.D. dissertation, California Institute of Technology (1999), I. Bankman, et al., "Optimal detection, classification, and superposition resolution in neural waveform recordings," *IEEE Trans. Biomed. Eng.*, 40:836-41 (1993), M. Abeles et al., "Multispike train analysis," *Proc. IEEE*, 65:762-73 (1977), and X. Yang et al., "A totally automated system for the detection and classification of neural spikes," *IEEE Trans. Biomed. Eng.*, 35:806-16 (1988). While matched filtering provides optimal performance, it is a supervised method, as is the method of principal components. Both power and amplitude detection methods can be implemented in an unsupervised manner. However, with the large changes in SNRs and firing rates that are typically found in movable electrode operations, these methods are fraught with inconsistent performance.

Generally, the detection of unknown signal in background noise is representation dependent. See M. Frisch et al., "The use of the wavelet transform in the detection of an unknown transient signal," *IEEE Trans. Info. Theory*, 38(2):892-97 (1992). Because of their excellent time-frequency properties, wavelets offer compact representation of signals embedded in a background noise, which make them a useful tool in the detection of local phenomena such as spike transients.

Combining the theory of wavelet transform, statistics, and detection theory, the inventors developed a robust unsupervised spike detection algorithm described in Z. Nenadic and J. Burdick, "Spike detection using the continuous wavelet transform," *IEEE Trans. on Biomed. Eng.*, 52(1):74-87 (2005). This approach can be used for unsupervised spike detection over a wide range of SNRs and firing rates. FIG. 8A shows a simulated neural signal for two neurons (the method used to simulate the neurons is described below in Example 3). FIG. 8B shows event vectors corresponding to the spikes detected in the neural signal of FIG. 8A by this wavelet method. The wavelet method may also be used to detect spikes in the neural signals recorded by the Sample Neural Signal Module 1100.

Spike Classification Module 1300

The Spike Classification Module 1300 includes instructions for spike alignment and spike clustering.

Spike Alignment

After detection, the event vectors may aligned to overcome the effects of jitter arising from background noise and finite sampling of the spike waveforms. See M. Sahani, "Latent variable models for neural data analysis," Ph.D. dissertation, California Institute of Technology (1999). Methods for aligning the event vectors (or spike segments) include alignment by the peak of detected spikes, the "center of mass" method, and the correlation method. See, e.g., K. Harris et al., "Accuracy of tetrode spike separation as determined by simultaneous intracellular and extracellular measurements," *J. Neurophysiol.*, 84:401-14 (2000), M. Sahani, "Latent variable models for neural data analysis," Ph.D. dissertation, California Institute of Technology (1999), and M. Abeles et al., "Multispike train analysis," *Proc. IEEE*, 65:762-73 (1977). The spikes may also be aligned by their minimums. Calculating a composite landmark of the spike, such as its center of mass, makes the alignment procedure more effective. This, however, is a supervised method that may not be suitable for use in connection with the present invention where the spike waveform's polarity can change with the electrode position.

The correlation method of Abeles et al. supra can be adapted to an unsupervised implementation, but a direct adaptation of this method, which is based on spike waveform averages, experiences problems in the multi-unit setting. To avoid such problems, the inventors fixed the first detected spike while time-shifting the second spike until its correlation with the first spike is maximized. The third spike is then time-shifted to maximize its correlation with the first and second spike, and so on. Such an optimization scheme depends upon the way in which the spikes are ordered (e.g., first, second, etc.). Finding a global optimum of this problem leads to a combinatorial optimization problem, which may not be feasible for on-line applications. The inventors found that ordering spikes by their amplitude leads to efficient suboptimal solutions. To account for spikes that are out of phase, the inventors use an absolute value of the correlation as an objective function. FIG. 8C shows event vectors after alignment using the inventive correlation method. Note that spike alignment effectively re-estimates the arrival times of detected spikes. Once aligned, the spikes are ready for clustering.

Spike Clustering

To determine the sources of individual spikes in the neural signal containing multi-neuron electrical activity, the inventors use cluster analysis. There are many different clustering methods, many of which are based on heuristic criteria. Unfortunately, many such methods do not provide a consistent answer regarding the number of classes in a data set. Alternatively, cluster analysis can be formulated within a probabilistic framework. The inventors used a clustering method based on finite mixture models, in which case the choice of the number of clusters reduces to a model selection problem. See, e.g., G. McLachlan et al., *Mixture Models: Inference and Applications to Clustering*, (Marcel Dekker: New York) (1988). Additionally, finite mixture models efficiently handle outliers. The basic steps of the inventive clustering method are summarized below and follow closely that of C. Fraley et al., "How many clusters? which clustering method? answers via model-based cluster analysis," *Computer J.*, 41:578-88 (1998) and Univ. of Wash., Dept. of Stats, "Model-based clustering, discriminant analysis, and density estimation," *Tech. Rep.*, 380, (October 2000).

Feature Extraction

To reduce the number of parameters necessary to describe a model, the first step extracts a low-dimensional feature set from the event vectors. Let $S \in R^{N_S \times N_t}$ be a matrix of $N_S$ aligned event vectors, where $N_t$ is the number of samples per event. For simplicity, the inventors only considered features that are linear function of the data, i.e., F=SE, where $F \in R^{N_S \times N_f}$ is the feature matrix, $E \in R^{N_t \times N_f}$ is the transformation matrix, and $N_f$ is the dimension of the feature space chosen by the user. The merit of this method is that $N_f \ll N_t$. However, alternative embodiments of this method may also use nonlinear feature extraction methods. Choosing the columns of E as the first $N_f$ principal eigenvectors of the covariance of S, gives rise to principal component features. Basis vectors of some canonical representation (e.g., wavelets) is another popular choice. For implementation purposes, the inventors successfully used both principal components and Haar wavelet coefficients as event vector features. FIG. 8D shows a two-dimensional feature space obtained using the first two Haar wavelet coefficients.

Finite Mixture Models

Let $f_i$ be a sample of the feature vector (ith row of matrix F) corresponding to the ith event. Presumably, this observation was sampled from an unknown probability density function ("PDF"). In the finite mixture model framework, it is assumed that this density can be modeled as a mixture density (i.e., a linear combination of G+1 component densities $p_j$). G corresponds to the number of clusters in the data. Observations may be generated by any of the component densities with some probability $\pi_j$ according to the following equation:

$$\pi_j \stackrel{\Delta}{=} P[f_i \text{ generated by } p_j(.|\theta_j)]$$
$$i = 1, 2, \ldots, N_s$$
$$j = 0, 1, \ldots, G,$$

where $\theta_j$ is a parameterization of the density $p_j$. The mixing parameters $\pi_j$ represent the prior probabilities of any observation belonging to $p_j$. Note that $\Sigma_{j=0}^{G} \pi_j = 1$. Viewed as a function of $$\{\Pi, \Theta\} \stackrel{\Delta}{=} \{\pi_j, \theta_j : j = 0, \ldots, G\}$$

the parameters rather than a function of data, the mixture density of a single observation is called the "mixture likelihood" and is given by $$L_{MIX}(\Pi, \Theta | f_i) = \sum_{j=0}^{G} \pi_j p_j(f_i | \theta_j)$$

$$i = 1, 2, \ldots, N_s.$$

Assuming the observations $f_i$ are statistically independent, the overall mixture likelihood is given by $$L_{MIX}(\Pi, \Theta | f_i) = \prod_{i=1}^{N_s} \sum_{j=0}^{G} \pi_j p_j(f_i | \theta_j) \qquad (1)$$

If the functional form of $p_j(.|\theta_j)$ is known, the parameters $\Pi^*$ and $\Theta^*$ that maximize the mixture likelihood (Eq. 1) can be estimated. In the context of clustering, the inventors restricted their attention to Gaussian components $\{p_j(.|\theta_j): j=1, 2, \ldots, G\}$ and a uniform component $p_0(.|\theta_0)=1/V$, where V is defined as the hyper-volume of the data. For the sake of notational compactness, the inventors keep $\theta_0$, although $\theta_0 = \{0\}$. Under the Gaussian noise assumption, the entries of the event vector matrix S are Gaussian random variables. Linear feature extraction further implies that the features are also Gaussian. If an observation $f_i$ belongs to a well-defined cluster, it is generated by one of the Gaussian components. If not, it is generated by the more diffuse uniform component $p_0$, and is declared an outlier.

Expectation-Maximization Algorithm

In general, the maximization of $L_{MIX}(\Pi, \Theta|F)$ must be performed numerically. For this task, the inventors employed the Expectation-Maximization (EM) algorithm, for which there is an extensive literature in the case of Gaussian mixtures. See, e.g., A. Dempster et al., "Maximum likelihood from incomplete data via the em algorithm," *J. Royal Stat. Soc.*, 39(1): 1-38 (1977) and J. Bilmes, "A gentle tutorial on the EM algorithm and its application to parameter estimation for gaussian mixture and hidden markov models," Univ. of Cal. Berkeley, Dept. of E. Eng. and Comp. Sci., Tech. Rep. (May 1997). Among known limitations of the EM algorithm, sensitivity to the choice of initial condition is among the most serious. A reasonable initial guess can be obtained by using one of the heuristic clustering techniques, as suggested by C. Fraley et al., "How many clusters? which clustering method? answers via model-based cluster analysis," *Computer J.*, 41:578-88 (1998). Once the optimal parameters $\Pi^*$ and $\Theta^*$ are known, the (hard) clustering rule is enforced via $$f_i \in C_{j^*} \Leftrightarrow j^* = \arg\max_{0 \leq j \leq G} p_j(f_i | \theta_j^*), \quad (2)$$

where $C_j$ is the label of the $j^{th}$ class, and $\theta_0^* = \{0\}$. FIG. 8E shows features clustered using the EM algorithm followed by the rule (Eq. 2), with a mixture of a uniform and two Gaussians (G=2).

Model Selection

Figure 8:
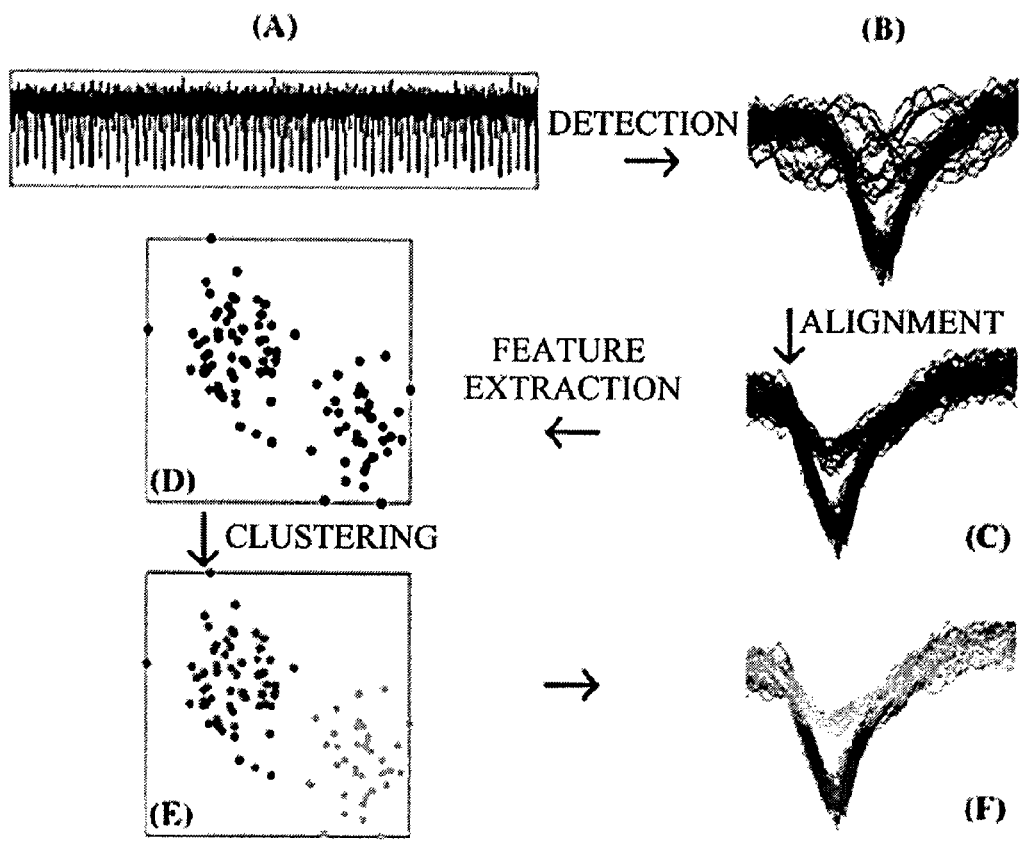
FIG. 8(A) shows simulated neural activity of two simulated neurons. The trace corresponds to 1 s of data.
FIG. 8(B) shows action potentials (spikes) detected using a wavelet detection method described in Z. Nenadic and J. Burdick, "Spike detection using the continuous wavelet transform," *IEEE Trans. on Biomed. Eng.*, 52(1):74-87 (2005). An event vector is a segment of the neural signal containing a single action potential.
FIG. 8(C) shows spikes aligned using the correlation method of the present invention.
FIG. 8(D) shows a plot of the spike features (Nf=2) extracted using the Haar wavelet. Each dot represents a single spike from FIG. 8(C).
FIG. 8(E) shows two clusters (dark and light gray) identified using a Gaussian mixture model in accordance with the present invention. There were no outliers illustrated in this figure.
FIG. 8(F) shows the aligned action potentials drawn in either dark or light gray according to the cluster to which they belong. In other words, FIG. 8(F) maps the clusters back to event space.

The model selection step estimates the number of clusters, G, in the event vector (spike) data S. Given a family of candidate mixture models $\{M_G: G=1, 2 \ldots, N_G\}$, the goal is to find the order of the model (the number of clusters) that optimally fits the data subject to some objective function. A straightforward selection of the maximum likelihood (ML) solution (i.e., the candidate that maximizes overall mixture likelihood (Eq. 1)), may lead to over-clustering, hence it may be desirable to employ other criteria. From Bayes' theorem, the probability of any candidate model, given the data F and a prior knowledge I about the problem, can be written as follows:

$$P(M_G|F,I) \propto p(F|M_G,I) P(M_G|I) \quad G=1,2,\ldots,N_G, \quad (3)$$

where P denotes a probability and p represents a PDF. The model that maximizes the posterior (Eq. 3) is to be chosen. Assuming that the candidate models have uniform priors $P(M_G|I)=1/N_G$, the maximization of the posterior reduces to the maximization of the term $p(F|M_G,I)$, which is called "integrated likelihood" in Bayesian probability theory. As the name suggests, the exact evaluation of this quantity involves numerical integration in multi-dimensional parameter space (e.g., a mixture of uniform and three Gaussian components in a 2D feature space requires 19 parameters). The inventors used an approximation based on the Bayesian Information Criterion (BIC), although other successful approximations have been reported as well. See, e.g., G. Schwarz, "Estimating the dimension of a model," *Annals of Stats.*, 6(2):461-64 (1978). The BIC is defined as follows:

$$BIC_G \triangleq 2\log p(F|M_G, I) \quad (4)$$
$$\approx 2\log L_{MIX}(\Pi^*; \Theta^* | F) - v_G \log N_s,$$
$$G = 1, 2, \ldots, N_G,$$

where $v_G$ is the number of parameters of the mixture $M_G$. The optimal model corresponds to the mixture with the highest BIC. For example, the features from FIG. 8 are tested against a family of five candidate models ($N_G=5$). The highest value of BIC corresponds to the mixture of uniform and two Gaussian components. Under the assumption that all candidates have equal priors (⅕) and that the parameters $\Pi^*$ and $\Theta^*$ are indeed the global optimum of the mixture likelihood (Eq. 1), this is equivalent to saying that two clusters are most likely given the data F and prior information I.

For a successful clustering, the number of observations $N_S$ must be sufficiently high with respect to the maximal order of the candidate model $N_G$. If not, the covariance matrices of individual components are typically ill-conditioned or singular, and may cause the EM algorithm to produce unreliable results. Since any number of events may be detected at each sampling position, the inventors chose the maximal order adaptively $N_G=N_G(N_s)$.

Calculate Signal Quality Metric Module 1400

As described above, the quality of the action potential signal may be measured for two purposes: (a.) to determine the acceptability of the current isolation and (b.) to measure the variation of signal quality around the neuron in order to find the optimal recording location. As also described above, signal quality metric used for the first purpose is referred to herein as the current signal quality metric and the signal quality metric used for the first purpose is referred to herein as the second signal quality metric. The current signal quality metric may be determined in a different manner from the second signal quality metric.

The signal quality metrics may be determined in several ways: (1) peak-to-peak amplitude ("PTPA"); (2) signal-to-noise ratio ("SNR"; i.e., the PTPA normalized by the noise RMS voltage, or PTPA/NoiseRMS); (3) distance in principal components space ("DPCS"; i.e., action potentials are projected onto their first two or three principal components and clustered, and then the signal quality metric is any distance (e.g., Euclidean, Mahalanobis, etc.) between the mean of the cluster furthest from the origin and that of its nearest neighbor, and if there is only one neuron present in the recording, its nearest neighbor will be the cluster corresponding to noise samples, and DPCS will be similar to PTPA); and (4) normalized distance in principal components space ("NDPCS"; i.e., the above metric normalized by the noise RMS voltage, or DPCS/NoiseRMS).

In some aspects of the autonomous algorithm 1000, a single second signal quality metric, such as the average peak-to-peak amplitude ("PTPA") of all action potentials within a cluster, may be used to represent all of the action potentials of the cluster. For example, to determine the dominant cluster, the second signal quality metric may be averaged over all action potentials within the cluster. Other aspects of the autonomous algorithm 1000, may consider the peak-to-peak amplitude ("PTPA") of each of the action potentials within the cluster separately. For example, the regression analysis implemented by the Model Isolation Curve Module 1500 discussed below and used to model the isolation curve may consider the second signal quality metric with respect to each of the action potentials within the cluster.

For constructing the isolation curve, PTPA may present a relatively simply choice. Therefore, the PTPA may be used for the second signal quality metric. PTPA is usually successful in isolating neurons and is the metric used to achieve the results described in the ensuing Examples. If there are several neurons of significant amplitude, however, maximizing the peak-to-peak amplitude of one neuron may not "separate" it from the other neuron (i.e., neither neuron will be isolated because action potentials cannot be reliably attributed to one of the neurons). DPCS is a metric that incorporates this notion of separation of multiple neurons. It may provide some improvement over PTPA, but it is also sensitive to errors in the unsupervised clustering; particularly to the task of determining the number of neurons present in a recording. The methodology used in connection with any particular embodiment of the present invention may thus be selected based on a variety of factors, as will be readily appreciated by those of skill in the art.

For determining the current signal quality metric which measures the current quality of the isolation (e.g., for determining the proper state transition as described below), a normalized metric may be used (SNR or NDPCS) to compare the signal quality to predetermined threshold levels of isolation acceptability (see FIG. 5). The normalization accounts for variations in the overall signal level due to differences in the electrical characteristics between electrodes. Similarly to the above choice between PTPA and DPCS, SNR is a simple and generally effective metric, while NDPCS may offer improvement in the multiple neuron case if its sensitivity to errors in clustering is reduced. The current signal quality metric used in the ensuing examples is the SNR.

In general, the presence of multi-neuron activity in the neural signal has to be accounted for in the definition of the second signal quality metric. Otherwise, the second signal quality metric may be averaged over different neurons, and will underestimate the signal quality of the dominant neuron. This, in turn may confound the autonomous algorithm 1000 to spurious maxima that could be far from optimum. Therefore, the second signal quality metric is first evaluated for each individual cluster. The cluster that provides the largest average value of the second signal quality metric is determined. As mentioned above, this cluster is the dominant class. Generally, the dominant class will contain multiple spikes, thus providing multiple observations of the second signal quality metric, which is important for the stochastic optimization scheme discussed below.

Figure 9:
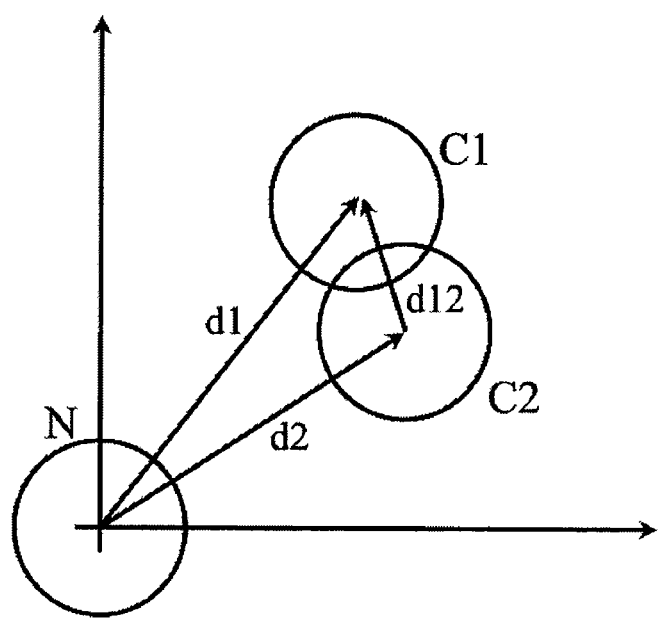
FIG. 9 shows a diagram illustrating circles that define the boundaries of three exemplary clusters, C1, C2, and N. The cluster N corresponds to the noise cluster and clusters C1 and C2 to clusters of action potentials. The arrows d1 and d2 illustrate the Euclidean distance between the center of the noise cluster and each of the clusters C1 and C2, respectively.

It is possible that by coming closer to the target neuron and thereby increasing the corresponding the second signal quality metric, the inventors could also be increasing the second signal quality metric of the spikes from the neighboring neurons. This appears to be a shortcoming of the above definition of signal quality. Because this definition relies solely on the information from the dominant class, it could lead to a solution with strongly confounding activity. In fact, the maximization of the PTPA of the spikes from the dominant cluster can be viewed as a maximization of the distance between the dominant cluster and a noise cluster (see FIG. 9). Using this method, cluster "C1" would be the dominant cluster in FIG. 9 because distance "d1" is larger than distance "d2." A more sophisticated definition of signal quality metric may also incorporate the distance between the dominant cluster and other clusters (e.g., distance "d12"). However, such a definition may be sensitive to misclassification, so the choice of metric may be viewed as a trade-off between the sensitivity to misclassification and the possibility of getting confounding activity.

Model Isolation Curve Module 1500

As described above, along a linear path of electrode travel past a neuron, plotting any metric of signal quality (e.g., PTPA) approximates the isolation curve (see FIG. 3 for an example of an ideal isolation curve). The actual isolation curve of any given neuron is not known in advance, nor is it necessarily symmetric or unimodal, but neither is required by the optimization method described below. The optimization method is independent of the metric used to determine the second signal quality metric.

The optimization method seeks to position the electrode 62 in the region of high and/or acceptable signal quality. When manually advancing neural probes, the electrode operator primarily relies on experience to interpret the observed signals and to control the movement of the electrode. However, the autonomous algorithm 1000 may treat electrode positioning as a problem in recursive stochastic optimization, or extremum seeking control. For illustrative purposes, the Model Isolation Curve Module 1500 will be described with respect to one electrode 62. However, it is apparent to those of ordinary skill embodiments incorporating multiple electrodes are within the scope of the present invention.

Let u and y(u) denote the position of the electrode 62 and the associated second signal quality metric along a linear track with an arbitrary origin, respectively. Because of the noise in neural signals, the metric y is a random variable with an associated regression function $M(u)=E(y|u)$, where $E(.|.)$ denotes the conditional expectation operator. $M(u)$ is the isolation curve of the dominant neuron. Generally, the function $M(u)$ is nonlinear. Moreover, it often exhibits unimodal character. The regression function is unknown; and must be estimated or modeled from noisy observations of the second signal quality metric calculated from the dominant class.

The Model Isolation Curve Module 1500 models the isolation curve $M(u)$ by estimating the regression function and determines the position u of the electrode 62 that maximizes the estimated regression function. The optimization method of the Model Isolation Curve Module 1500 is described below and in Z. Nenadic and J. Burdick, "A control algorithm for autonomous optimization of extracellular recordings", *IEEE Trans. on Biomed. Eng.*, 22(4):694-710, 2006.

Kiefer-Wolfowitz Scheme and its Limitations

The solution to the problem of regression function maximization, where only its noisy observations are available, was first addressed within a framework of recursive stochastic optimization. See J. Kiefer and J. Wolfowitz, "Stochastic estimation of the maximum of a regression curve," *Annals of Math. Stat.*, vol. 23, pp. 462-466, 1952. Let $M(u)=E(y|u)$ be an unknown regression function with a (local) maximizer $u^\circ = \arg\max_u M(u)$. The maximizer u can be found numerically through the following recursive procedure also known as a Kiefer-Wolfowitz (KW) scheme:

$$u_{k+1} = u_k + \rho_k \xi_k, \quad k=1,2,\ldots, \qquad (5)$$

where $u_{k+1}$ and $u_k$ are the positions of the electrode 62 at movement iterations k+1 and k, respectively, $\rho_k$ is a variable step size and $\xi_k$ is a statistical estimate of the derivative of $M(u)$ at point $u_k$ given by:

$$\xi_k = \frac{1}{L}\sum_{l=1}^{L}\frac{y(u_k + \varepsilon_k, \omega_{2l}) - y(u_k, \omega_{2l-1})}{\varepsilon_k} \quad (6)$$

Here, L represents the number of observations taken at each recording position, $y(u,\omega)$ is a random sample of the regression function (e.g., PTPA) at point u, and $\epsilon_k$ determines the spacing for the finite difference approximation to the derivative. The sample variable $\omega$ signifies that only random samples of the regression function are observed, while the subscript of $\omega$ indicates different observations of a random variable. Note that Eq. (5) represents a stochastic version of the gradient ascent method. Also note that L acts as a smoothing parameter in Eq. (6).

Under relatively mild regularity conditions on M(u) and for appropriate choice of the parameters $\rho_k$ and $\epsilon_k$, it can be shown that the sequence generated by the recursion (5) converges with probability 1 to the (local) maximizer u. See Id. and Y Ermoliev and R. J.-B. Wets, "Stochastic programming, an introduction," in *Numerical Techniques for Stochastic Optimization*, Y Ermoliev and R. J.-B. Wets, Eds. New York: Springer-Verlag, 1988, ch. 1, pp. 1-32. For example, the sequences $\rho_k = \epsilon_k = C/k^\tau$, where C>0 is a constant and $\Sigma\epsilon(0.5,1]$ guarantee convergence. In this case, C represents the initial step size and $\tau$ is the rate of decay of the step size.

Despite proven convergence properties, the KW scheme suffers from some practical problems. For example, the variance of $\xi_k$ tends to grow with k, resulting in relatively slow convergence rates. Assuming that the observations are independent, it follows readily from Eq. (6) that $\lim_{\epsilon_k \to 0}\{Var(\xi_k)\} \to \infty$. Eventually, the step size stabilizes and convergence is insured by the fact that $\lim_{k \to \infty}\rho_k \to 0$, but this comes at a high cost; not only is the convergence slow, but also the high variance of $\xi_k$ translates into excessive dithering of the electrode 62 for intermediate values of k. In practical applications, the unnecessary back-and-forth electrode movement inevitably leads to excessive tissue damage and possible inflammatory reactions. Furthermore, to evaluate the finite difference in Eq. (6), the probe must make excursions away from $u_k$. This again results in undesirable electrode movements. These problems make the KW scheme and related difference based recursions ill-suited for use with the autonomous algorithm 1000. See J. H. Venter, "On convergence of the kiefer-wolfowitz approximation procedure," *Annals of Math. Stat.*, vol. 38, 1967.

The core of the KW scheme relies upon the statistical estimate of the derivative of a regression function from its noisy observations. In general, taking a difference of noisy data amplifies the effect of noise, which is the main reason for non-smoothness of difference-based techniques. Therefore, it might be worthwhile to estimate the regression function itself, rather than its derivative. The derivative of the estimated regression function may provide a smoother, less noisy signal that may be used by the neural isolation procedure.

Adaptive Estimation Of Regression Function Model

Let $\{u_1, u_2, \ldots, u_k\}$ be a sequence of positions of electrode 62 after k iterations with the corresponding random samples of the second signal quality metric $\Upsilon_{1:k} = \{y(u_1,\omega), y(u_2,\omega), \ldots, y(u_k,\omega)\}$. At each location $u_j (=1, 2, \ldots, k)$, multiple observations of the second signal quality metric are taken, i.e. $y(u_j,\omega) = \{y(u_j,1), y(u_j,2), \ldots, y(u_j,m_j)\}$, where and $m_j$ is the total number of observations at $u_j$. In general $m_1 \neq m_2 \neq \ldots m_k$.

A general model for the regression function M(u) after k iterations can be expressed in the following form:

$$\hat{M}(u, n_k, B_k, \Theta_k) = \sum_{i=1}^{n_k} b_{i,k}\varphi_i(u, \Theta_k) \quad (7)$$

where $\phi_i(u, \Theta_k)$ are basis functions (which may be chosen by the user), $B_k = [b_{1,k}, b_{2,k}, \Lambda, b_{n_k,k}]^T$ are the corresponding expansion coefficients, $n_k$ is the number of basis functions, and $\Theta_k$ is a parameterization of the basis functions. In various embodiments, the basis functions are polynomials, while in alternate embodiments the basis functions are radial basis functions. While the model $\hat{M}$ depends linearly on $B_k$, the dependence on $\Theta_k$ is typically nonlinear. For example, in the case of radial basis functions, $\Theta_k$ represents a set of means and variances. It may be desirable to select basis functions with known functional forms that are differentiable. The parameters $n_k$, $B_k$ and $\Theta_k$ may be unknown and may be estimated from the data.

The parameter $n_k$ determines the complexity of the model. Determining the value of $n_k$ is a model selection problem. Given a family of models $\{\hat{M}(u,n_k,B_k,\Theta_k):n_k=1, 2,\Lambda, N\}$, where N is the maximal order of the candidate model (a number chosen before the experiment begins), the goal is to select the model that optimally fits the data. The definition of optimality affects the estimate $\hat{M}$. For example, maximizing the likelihood of the model, leads to the ML solution. The problem with this method is that it favors the model of highest complexity ($n_k = N$), which commonly leads to over-fitting. Overfit models are likely to be noisy, which may cause excessive dithering of the electrode 62 as it nears the optimal neural isolation position. There are many methods that effectively prevent over-fitting. Some of them are based on heuristic criteria (e.g. cross-validation), while others are based on approximations of various statistical quantities (e.g. Akaike Information Criterion (AIC) or BIC used above). See M. Stone, "Cross-validatory choice and assessment of statistical predictions," *J. Roy. Statist. Soc.*, B, vol. 36, pp. 111-147, 1974; H. Akaike, "A new look at the statistical model identification," *IEEE Trans. Automat. Contr.*, vol. AC-19, pp. 716-723, 1974.

Bayesian Model Selection

Figure 10:
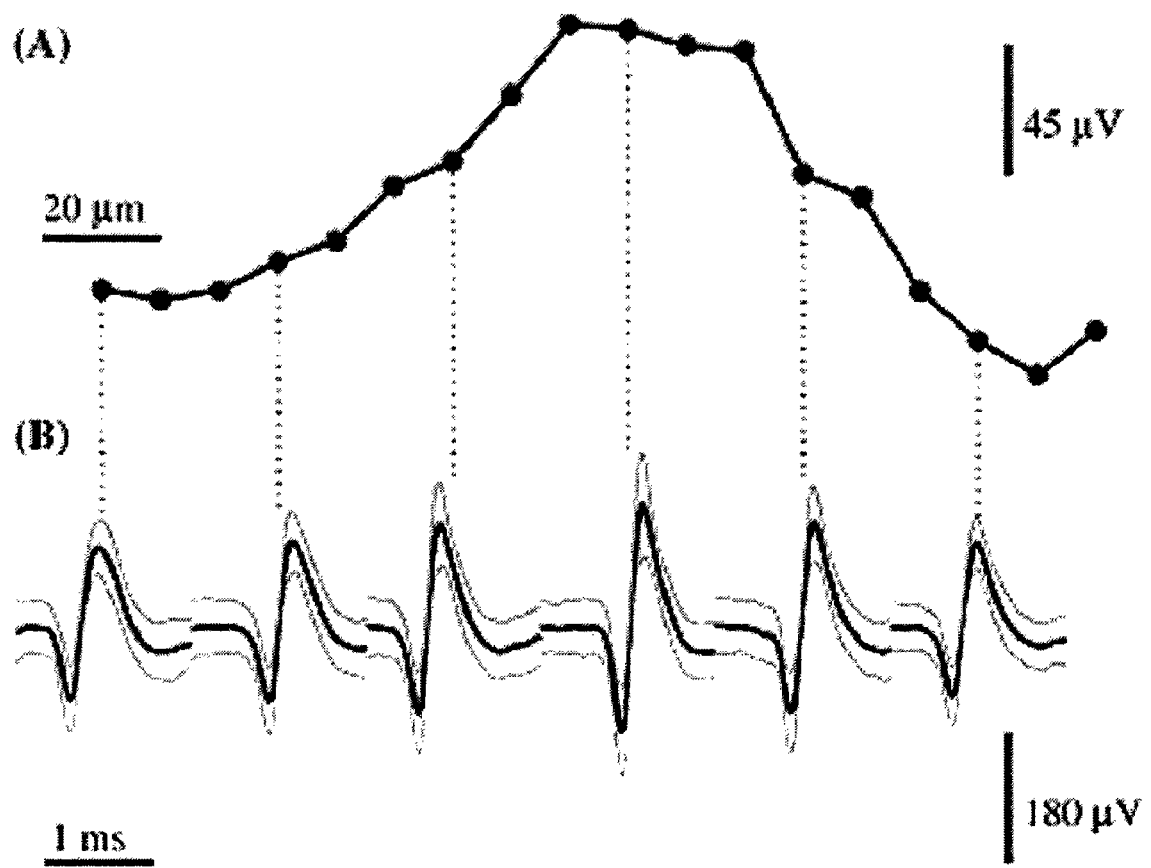
FIG. 10(A) shows an exemplary isolation curve for a neuron of the parietal reach region of a monkey posterior parietal cortex. The second signal quality metric used in this example was PTPA. The data was obtained by moving an electrode along a straight line in 10 μm increments and recording for approximately 10 s at each location. The curve was constructed by averaging the PTPA of the spikes detected at each location. The number of spikes per location varied from 213 to 478. In the large number of spikes, this curve converges (pointwise) to a curve generated by a regression function of the PTPA and electrode position.
FIG. 10(B) shows a spike illustrating the ensemble average at locations marked by dotted lines. Each of the spikes illustrating the ensemble average is located between a pair of spikes. The upper curve above each spike waveform represents the sum of the ensemble average and the standard deviation. The lower curve below each spike waveform represents the ensemble average minus the standard deviation. In other words, the range between the upper and lower curves represent about 68% of the PTPA of the spikes at each of the locations marked by the dotted lines.

Another solution to over-fitting is offered by Bayesian probability theory. See E. Jaynes, *Probability theory: the logic of science*, G. L. Bretthorst, Ed. New York: Cambridge University Press, 2003. Unfortunately, the nonlinear dependence of the model on parameters $\Theta_k$, renders the Bayesian model selection computationally unfeasible. However, if the basis functions are parameter-free, the solution to the Bayesian model selection can be found analytically. To render the basis functions are parameter-free, the basis functions are assumed to be polynomial basis functions $\phi_i(u) = u^{(i-1)}$. While such a choice may seem restrictive, isolation curves are often simple (see FIG. 10); therefore, they can be accurately modeled using polynomials of low order. To increase the flexibility of the model and account for modeling of more complex regression functions, the maximal order N of the candidate model may be increased. Using these basis functions, the model proposed by Eq. (7) reduces to a linear function of the parameters $B_k$, i.e.

$$\hat{M}(u, n_k, B_k) = \sum_{i=1}^{n_k} b_{i,k} u^{(i-1)} \quad (8)$$

Given a family of candidate models $\{\hat{M}(u, n_k, B_k): n_k=1, 2, \Lambda, N\}$, the goal is to select the order of the model that is most probable in view of the data $\Upsilon_{1:k}$ and any prior information, I. The probability of the model $\hat{M}_{n_k}$, given $\Upsilon_{1:k}$ and I follows from Bayes' theorem $$P(\hat{M}_{n_k} | \Upsilon_{1:k}, I) = \frac{p(\Upsilon_{1:k} | \hat{M}_{n_k}, I) P(\hat{M}_{n_k} | I)}{p(\Upsilon_{1:k} | I)} \quad (9)$$

$$n_k = 1, 2, \ldots N$$

where $\hat{M}_{n_k}$ is short for $\hat{M}(u, n_k, B_k)$ with fixed $n_k$, P is a probability mass function and p is a PDF. For successful Bayesian model selection, the number of iterations k has to be sufficiently high with respect to the maximal order N. The smallest admissible number of iterations is denoted by $k_0$. In some embodiments, $k_0$ is set equal to five. For iterations up to $k_0$, the sampling of data is simply not adequate to reliably model the regression function. The order of the model is selected that maximizes the posterior probability $P(\hat{M}_{n_k} | \Upsilon_{1:k}, I)$, i.e.

$$n_k^* = \arg\max_{1 \leq n_k \leq N} P(\hat{M}_{n_k} | \Upsilon_{1:k}, I)$$

$$k = k_0, k_0 + 1, \ldots$$

In order to perform the maximization above, the posterior $P(\hat{M}_{n_k} | \Upsilon_{1:k}, I)$ of each candidate model $\hat{M}_{n_k}$ must be evaluated. To carry out this calculation, the unknown parameters $B_k$; must be integrated out by a process called marginalization. Because of the Gaussian noise assumption and linear dependence of the model on the parameters, the marginalization of $B_k$ may be performed analytically, thus avoiding computationally expensive numerical integrations in multi-dimensional parameter space. Consequently, the computation of the posteriors $P(\hat{M}_{n_k} | \Upsilon_{1:k}, I)$ yields an analytic solution. See e.g., G. L. Bretthorst, "Bayesian analysis. ii. signal detection and model selection," J. *Magn. Reson.*, vol. 88, pp. 552-570, 1990. In the spirit of Bayesian probability theory, the posterior $P(\hat{M}_{n_k} | I)$ calculated at iteration k can be used as a guess for the prior $P(\hat{M}_{n_k} | I)$ at iteration k+1 in Eq. (9). The recursion is initialized as $P(\hat{M}_{n_k} | I) = 1/N$ at iteration $k=k_0$, which reflects complete initial ignorance about the model. Once the order $n^*_k$ of optimal model at iteration k is known, the parameters of the model $\hat{M}(u, n^*_k, B_k)$ need to be estimated.

Parameter Estimation

Bayesian probability theory can also be used to infer the posterior of parameters $B_k$ given the observations $\Upsilon_{1:k}$ and prior information I. Once the posterior is known, the maximum posterior solution can be found, i.e., $B^*_k = \arg\max_{B_k} p(B_k | \Upsilon_{1:k}, I)$. However, it is easier and computationally more efficient to use the ML method, which under the linear model (8) and Gaussian noise assumption, reduces to the linear least squares method. As the number of observations increases, the influence of the prior information I on the estimate decreases, and the ML solution approaches the maximum posterior solution. Therefore, the parameter estimation problem can be formulated as follows:

$$B^*_k = \arg\min_{B_k}\left\{\sum_{j=1}^{k} \|\Psi_{j,k} B_k - Y_j\|^2\right\} \quad (10)$$

$$k = k_0, k_0 + 1, \ldots$$

where $Y_j = [y(u_j, 1), y(u_j, 2), \ldots, y(u_j, m_j)]^T$ and the matrix $\Psi_{j,k} \in R^{m_j \times n^*_k}$ consists of $m_j$ identical rows given by: $[1, u_j, \Lambda, u_j^{(n^*_k-1)}]$. The analytical solution to Eq. (10) reduces to finding the pseudo-inverse of a matrix. Once the optimal parameters $B^*_k$ are estimated, the optimal model $$\hat{M}^{(k)}(u) \triangleq \hat{M}(u, n^*_k, B^*_k)$$

at iteration k is fully specified.

Recursive Stochastic Optimization with Basis Functions

From Eq. (8) it follows that at iteration k the derivative M'(u) of the regression function can be estimated as:

$$\xi_k = \sum_{i=1}^{n^*_k - 1} i b^*_{i+1,k} u_k^{(i-1)}$$

$$k = k_0, k_0 + 1, \ldots$$

$$n^*_k \geq 2.$$

Similarly, M'' (u) can be estimated at iteration k, denoted by $H_k$. Instead of the KW scheme (5) the following equation is used:

$$u_{k+1} = u_k + C|H^k|^{-1} \xi_k \quad k=k_0, k_0+1, \quad (11)$$

where C>0 is an appropriately chosen scale factor, and $\xi_k$ and $H_k$ are the estimates of the first and second derivative of the regression function at point $u_k$, respectively. As is apparent to those of ordinary skill, the amount the electrode 62 is moved each iteration is approximately equal to $C|H^k|^{-1}\xi_k$ and upon each visit to the block 2402, the variable "move" of the Isolate Neuron state 2400 may be set equal to $C|H^k|^{-1}\xi_k$.

Note that Eq. (11) represents a stochastic version of Newton's method with superior convergence properties than stochastic gradient ascent method. See L. Ljung and T. Sbderstrom, *Theory and Practice of Recursive Identification*, Cambridge, Mass.: The MIT Press, 1983, ch. 2, pp. 12-66. The convergence is considered attained at iteration k* if $C|H_k|^{-1}\xi_k^* <$Tol and the position $u_k$. declared a solution. Tol is a predetermined tolerance threshold that may be chosen by the user. The threshold "MIN_MOVE" of the Isolate Neuron state 2400 may be equal to Tol. Tol may assume a wide range of values, but typically the value of Tol may be in the range of about 1 micron to about 5 microns. As is apparent to those of ordinary skill, the value of Tol may depend upon the physiology of the neural tissue in which the electrode 62 is positioned.

The scale factor C may be used to calibrate the step size in Eq. (11), although large steps may occur occasionally, especially in the early iterations when the estimated model $\hat{M}^k(u)$ may be far from the true isolation curve M(u). In the context of the electrode 62, large steps may be unacceptable, as they might introduce unnecessary tissue damage or deformation during the execution of the large step. Therefore, it may be desirable to limit the maximum step size to a predetermined maximum $\Delta_{max}$. This limitation is especially useful for iterations where the optimal model is found to be a straight line ($n^*_k=2$), which results in $H_k=0$ and infinitely large step size in Eq. (11). Likewise, if for some $k>k_0$ the estimated model is $\hat{M}^k(u)=b^*_{1,k}$, i.e., ($n^*_k=1$) then $\xi_k=0$ and the recursion (11) breaks. In this case, the following simple control strategy may be used:

$$u_{k+1}=u_k+\Delta \qquad (12)$$

where $\Delta$ is a constant step size chosen before the experiment initiates. Finally, for iterations $k<k_0$ the control strategy of Eq. (12) may be employed.

Microdrive

Figure 11:
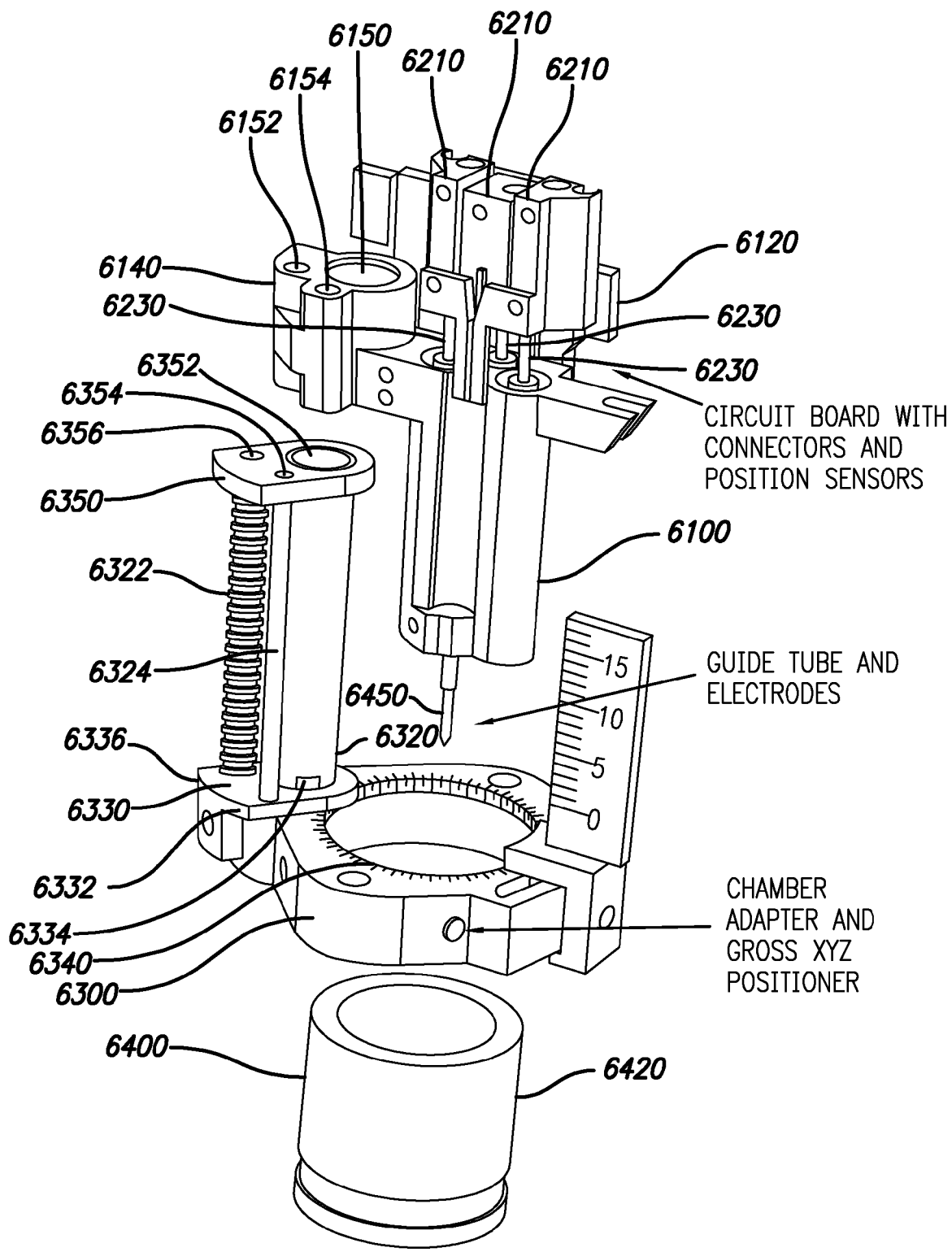
FIG. 11 shows a perspective view of one embodiment of a microdrive constructed in accordance with an embodiment of the present invention.
Figure 12B:
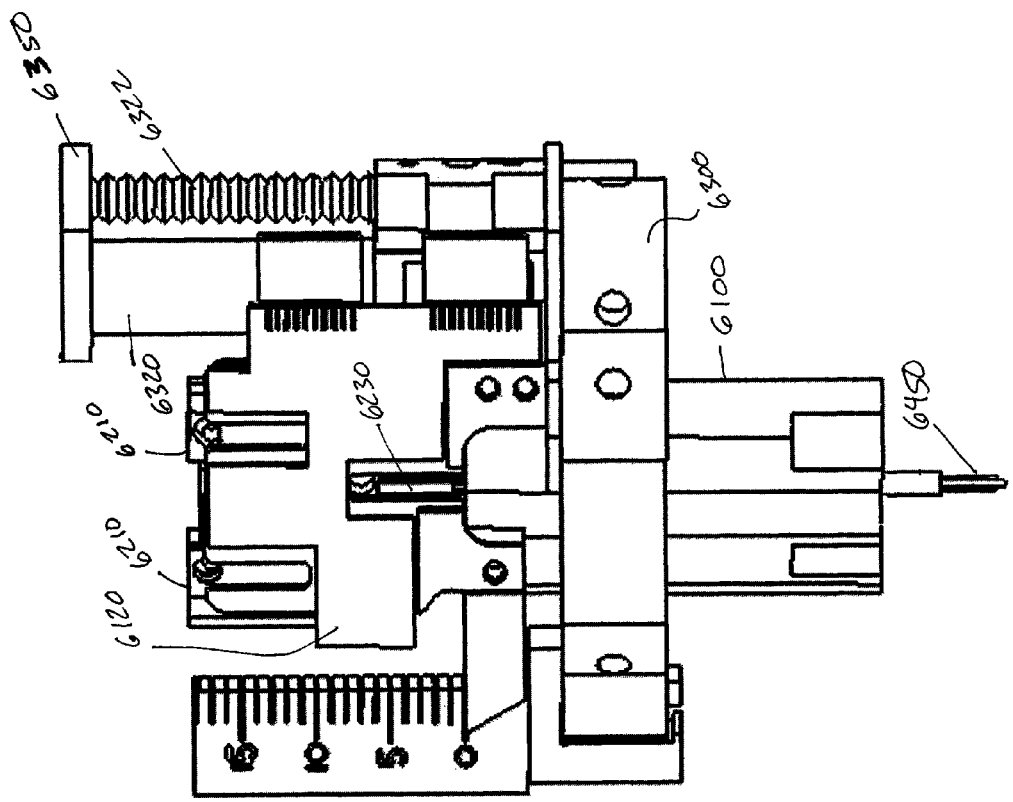
FIG. 12B shows a view of the back of the microdrive of FIG. 11.
Figure 12:
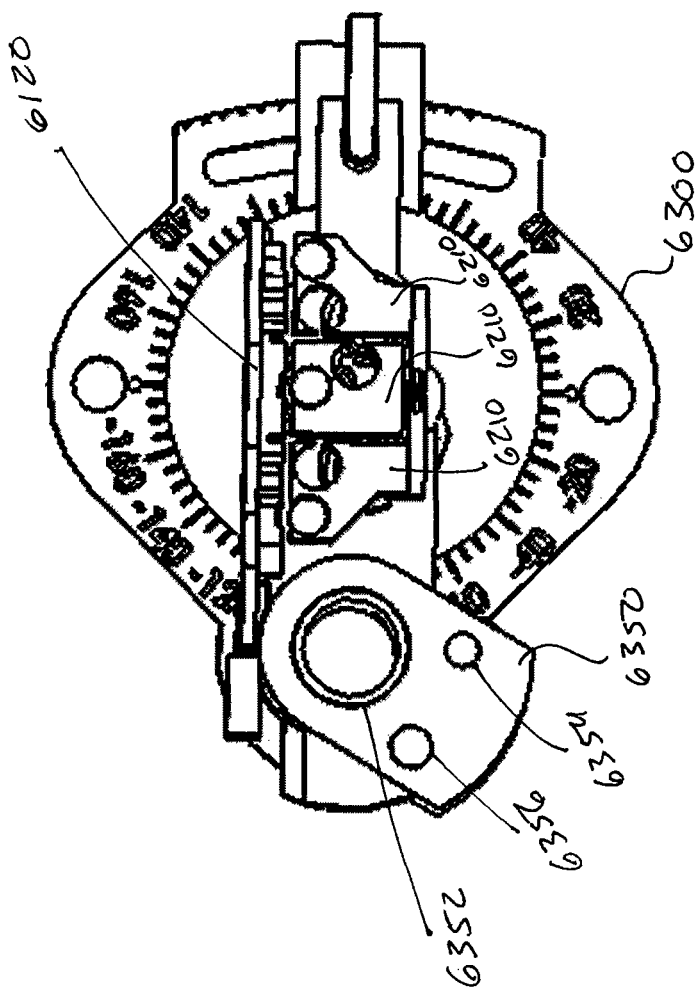
FIG. 12A shows a view of the front of the microdrive of FIG. 11.
FIG. 12C shows a view of the bottom of the microdrive of FIG. 11.
FIG. 12D shows a view of the top of the microdrive of FIG. 11.
FIG. 12E shows a sectional view of the microdrive of FIG. 11 taken along a plane substantially parallel with the front view of FIG. 12A.
FIG. 12F shows a sectional view of the microdrive of FIG. 11 taken along a plane substantially parallel with the front view of FIG. 12A and nearer the front of the device than the plane of the view in FIG. 12E.
FIG. 12G shows a sectional view of the microdrive of FIG. 11 taken along a plane substantially parallel with the top view of FIG. 12D.
Figure 12E:
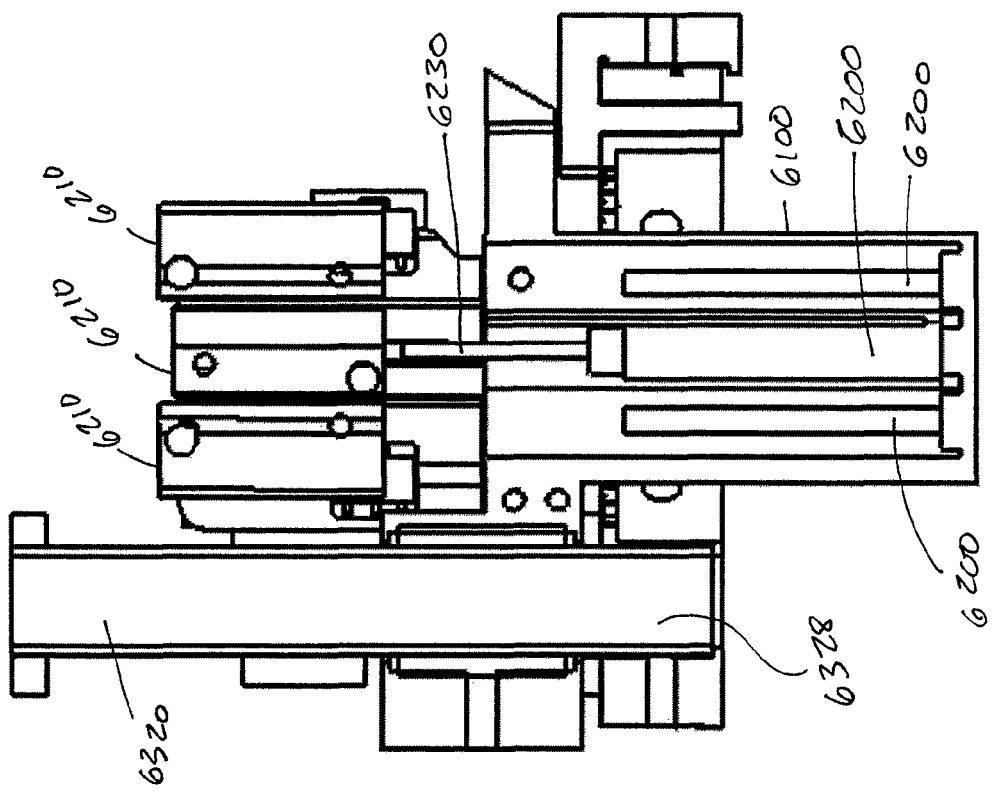
Figure 12F:
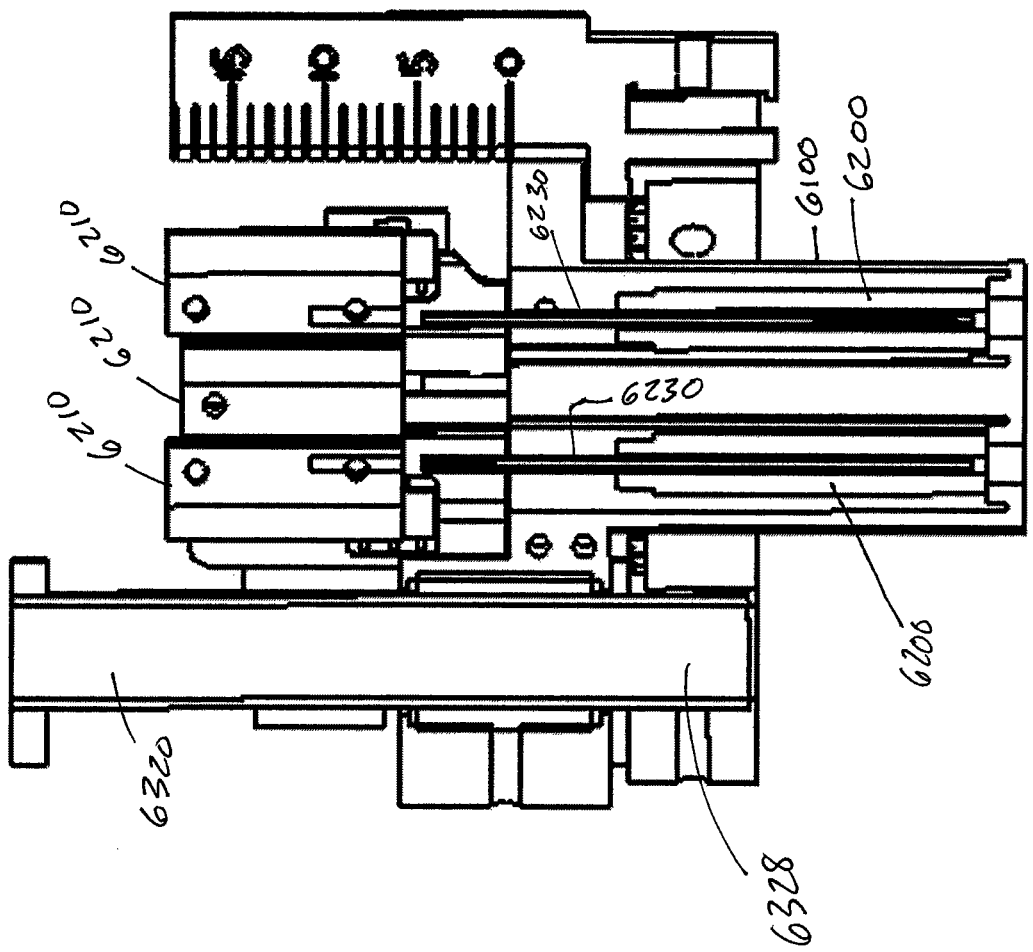
Figure 12G:
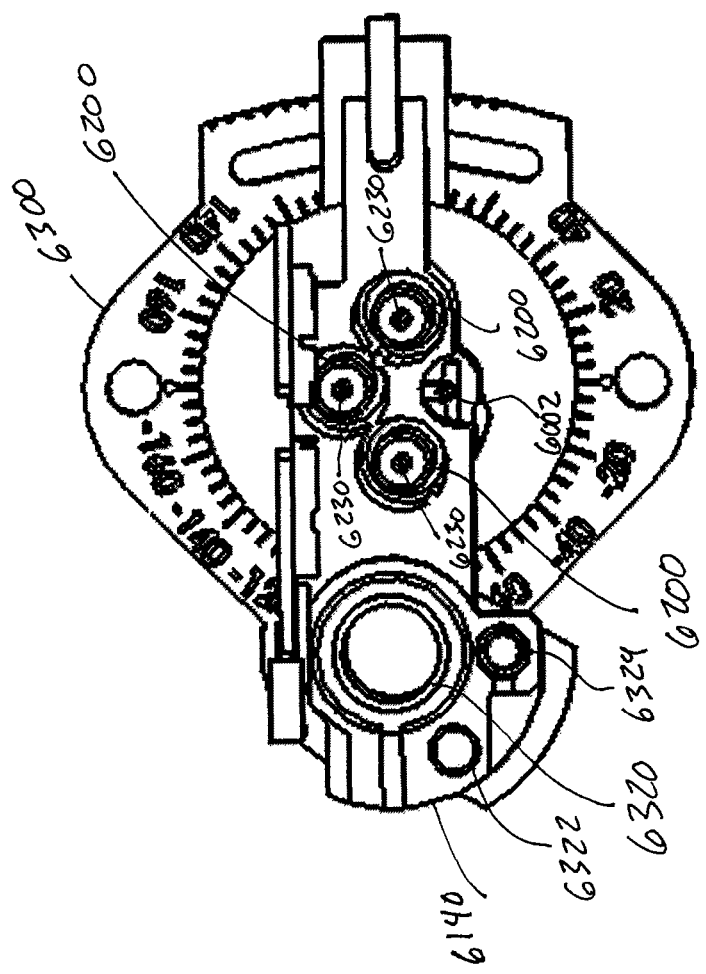
Figure 13:
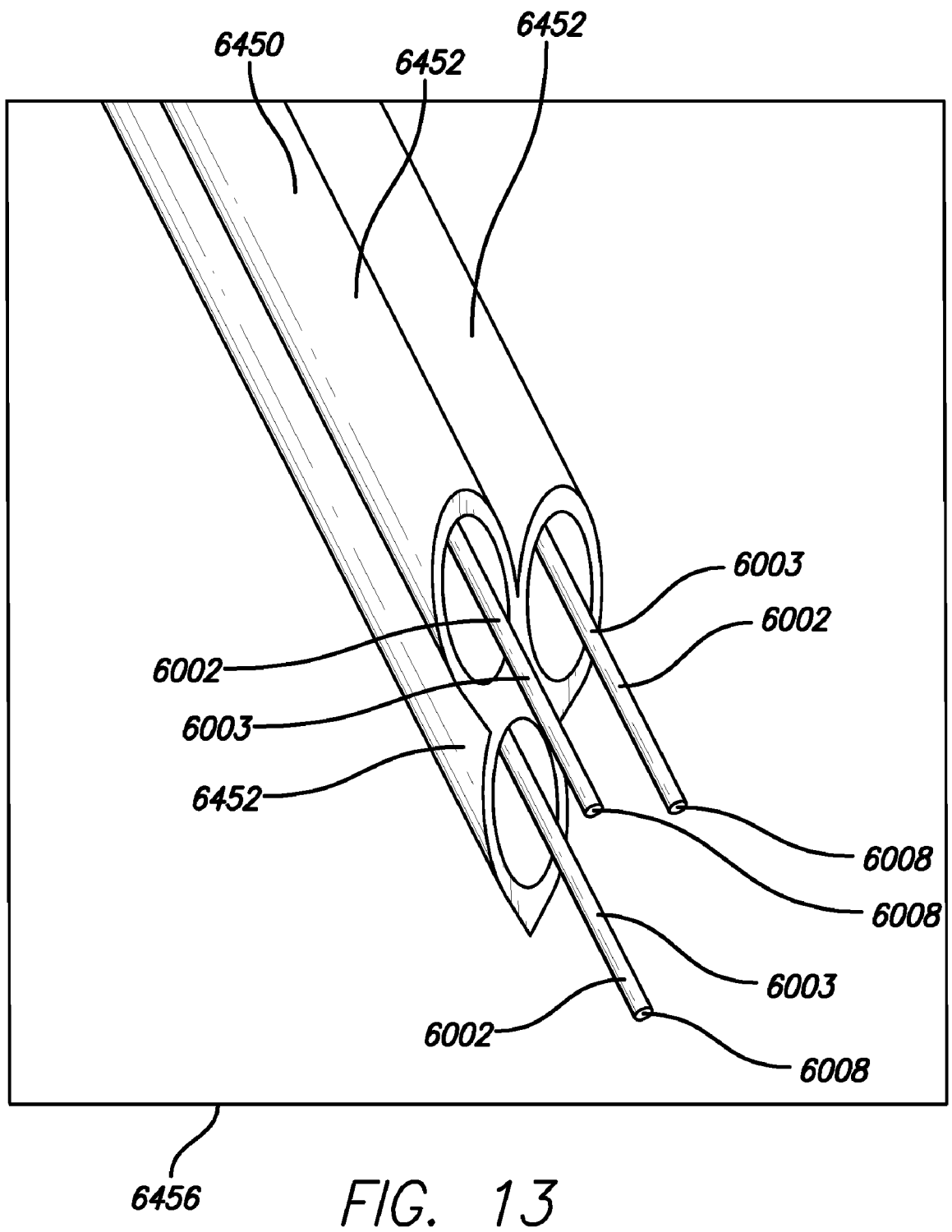
FIG. 13 shows a perspective view of a guide tube and the tips of three electrodes of the microdrive of FIG. 11.

Referring to FIGS. 11-13, one aspect of the invention includes the microdrive 6000. The microdrive 6000 includes what is believed to be a novel use of one or more small linear piezo-electric motors or actuator(s) 6200 to independently position the electrode(s) 6002. The piezoelectric actuators 6200 provide a small step size needed for positioning accuracy, and sufficiently fast acceleration of the electrode(s) 6002 while executing small steps. The fast acceleration and small step size may help minimize tissue damage caused by the electrode(s) 6002. One piezo-electric actuator 6200 per electrode 6002 may be used to advance or retract the electrode 6002 into neural tissue.

The central structure of the microdrive 6000 may include a main body 6100, which encases three piezo-electric linear actuators 6200. In one non-limiting embodiment, the piezo-electric actuators 6200 are about 3 millimeters in diameter and about 4 centimeters in length. An electrode guide tube 6450 and circuit board 6120 may be mounted to the main body 6100 of the microdrive 6000. The guide tube 6450 may provide for precise lateral positioning of the electrode(s) 6002. The sharpened tip of the guide tube 6450 may help the microdrive penetrate the dura, a tough outer membrane surrounding the brain. In one embodiment, the linear actuators 6200 are spaced apart horizontally and located in a bottom portion of the main body 6100. A portion of the guide tube 6450 may be located between two or more of the linear actuators 6200.

Each of the linear actuators 6200 may be coupled to a single movable carrier 6210 located at the top of the main body 6100 by a vertically extending shaft 6230. An end 6004 of each of the electrodes 6002 is attached both electrically and mechanically to one of the movable carriers 6210. The end 6004 of the electrodes 6002 may be attached to the movable carriers 6210 by fixing the end 6004 with a fastener (not shown) such as a screw. The fastener may supply both a mechanical and electrical connection between each electrode 6002 and one of the movable carriers 6210. The electrodes 6002 may extend downwardly from the movable carriers 6210 and through the guide tube 6450. Depending upon the vertical position of the movable carriers 6210, the electrodes 6002 may exit the guide tube 6450 into the environment outside the microdrive 6000.

In some embodiments, the linear actuators 6200 provide simultaneous high-precision electrode positioning and long range of electrode motion without suffering from gear backlash. High-precision electrode positioning may include moving the electrode(s) 6002 in step sizes smaller than one micron. A suitable long range of electrode motion may be about 5 millimeters. In alternate embodiments, the suitable long range may be about 1 centimeter as this distance represents the entire thickness of a human and primate cortex. As non-limiting examples, suitable piezo-electric actuators may be obtained from Klocke Nanotechnik, Germany.

The electrodes 6002 may be constructed from platinum-iridium wires 6003 and may be coated with glass along a portion of their outside surface. The glass coating 6006 may electrically insulate the wires 6003. In one embodiment, the platinum-iridium wires 6003 are coated along their length with glass except at tip 6008 and end 6004. The tip 6008 may remain uncoated to place it in electrical communication with neurons in the brain. A portion of the end 6004 may be uncoated to allow the neural signals detected by the tip 6008 to be transmitted to the circuit board 6120. Suitable glass coating may be purchased from Alpha Omega Co., USA. In one embodiment, flexible, polyimide-shielded copper strips (now shown) connect the ends 6004 of each of the electrodes 6002 to the circuit board 6120.

The circuit board 6120 may include Hall-effect sensors (not shown) that may be used to determine the depth of the electrodes 6002. In one embodiment, the Hall-effect sensors have a precision of about 1 micron. The circuit board 6120 may also contain signal conditioning circuitry to amplify and filter the output of the Hall-effect sensors.

The circuit board 6120 may include a connector (not shown), such as a standard multi-pin connector and the like, that is connected to the headstage amplifier 801 (see FIG. 2). The neural signals detected by the tip 6008 and transmitted to the circuit board 6120 may be transmitted to the headstage amplifier 801 by the connector.

The microdrive 6000 may include a chamber adapter 6300 that connects the main body 6100 to a standard cranial recording chamber 6400. A portion of a bottom 6410 of the cranial recording chamber 6400 is received within the skull of the subject and a portion of a top 6420 of the cranial recording chamber 6400 is exterior to and extends outwardly from the skull. While a generally cylindrical cranial recording chamber 6400 is depicted in the drawings for illustrative purposes, those of ordinary skill in the art appreciate that the present invention is not limited by the structure of the cranial chamber.

The microdrive 6000 may include a generally cylindrically shaped vertically extending main shaft 6320. The microdrive 6000 may also include a vertically extending threaded lead screw 6322. Optionally, the microdrive 6000 may include a generally cylindrically shaped vertically extending secondary shaft 6324. The diameter of the secondary shaft 6324 may be smaller than the diameter of the main shaft 6320. In one embodiment, the diameter of the main shaft 6320 is about 3 mm to about 5 mm. The diameter of the secondary shaft 6324 may be about 1 mm to about 2 mm. The main shaft 6320 may be longer than the secondary shaft 6324. In one embodiment, the main shaft 6320, threaded lead screw 6322, and secondary shaft 6324 are spaced laterally from one another and arranged to be substantially parallel to one another along their longitudinal axes.

The microdrive 6000 may include a substantially planar support member 6330 having a through-hole 6332 sized and shaped to receive one end of the main shaft 6320. The support member 6330 may also have a through-hole sized 6334 and shaped to receive one end of the secondary shaft 6324. The support member 6330 may also have a through-hole sized 6336 and shaped to receive one end of the threaded lead screw 6322. The diameter of the through-hole 6336 may be larger than the maximum diameter of the threads of the lead screw 6322 allowing the lead screw 6322 to turn freely within the through-hole 6336 without engaging the inside surface of the through-hole 6336.

A top cap 6350 may include through-holes holes 6352, 6354, and 6354 substantially similar to through-holes 6332, 6334, and 6334, respectively. A portion of the end of the lead screw 6322 may extend upwardly through the through-hole 6356. A nut 6326 or similar component may be placed on the end of the lead screw 6322 extending upwardly through the through-hole 6356 to facilitate turning the lead screw 6322 and maintain the lead screw 6322 within the through-holes 6336 and 6356. In embodiments wherein the main shaft 6320 that is longer than the secondary shaft 6324 and/or lead screw 6322, a portion 6328 of the main shaft 6320 may exit the through-hole 6332 and extend downwardly away from the support member 6330.

The main body 6100 may include a slider 6140 configured to slide along the main and secondary shafts 6320 and 6324, respectively. The slider 6140 may include a main collar 6150 configured to longitudinally receive and slid vertically along a portion of the main shaft 6320. The slider 6140 may include a threaded through-hole 6152 having threading along its inside surface configured to engage the threads of the lead screw 6322. The slider 6140 may include a secondary collar 6154 configured to longitudinally receive and slide vertically along a portion of the secondary shaft 6324. When the lead screw 6322 is turned (i.e., rotates within through-holes 6336 and 6356) the threads of the lead screw 6322 engage the threads of the threaded through-hole 6152 and exert a vertically directed force upon the slider 6140 of the main body 6100. Turning the lead screw 6322 in one direction will exert an upward force moving the slider 6140 of the main body 6100 upward and away from the skull along the main and secondary shafts 6320 and 6324, respectively. Turning the lead screw 6322 in the opposite direction will exert a downward force moving the main body 6100 downwardly and toward the skull along the main and secondary shafts 6320 and 6324, respectively.

The microdrive 6000 may include a chamber adapter 6300. The chamber adapter 6300 may include a ring 6340 and a collar 6342. The collar 6342 is sized and shaped to receive the portion 6328 of the main shaft 6320 exiting the through-hole 6332 and extending downwardly away from the support member 6330. In some embodiments, the collar 6342 may rotate about the longitudinal axis of the main shaft 6320 to position the main body 6100 relative to the chamber adapter 6300. The support member 6330 may include a downwardly extending member 6331 having a through-hole 6333 sized and shaped to receive a fastener (not shown) such as a bolt or screw. The fastener that may be inserted into the through-hole 6333 and may bear against the outside surface of the collar 6342 thereby preventing rotation of the main body 6100 about the main shaft 6320. Alternatively, the outside surface of the collar 6342 may include an aperture (not shown) configured to receive the fastener.

The ring 6340 has a recessed portion 6344 along its bottom surface 6346 defined by a downwardly extending sidewall 6348. The recessed portion 6344 is sized and shaped to receive and rest upon a portion of the top 6420 of the cranial recording chamber 6400. In embodiments including a generally cylindrically shaped cranial recording chamber 6400, the chamber adapter 6300 may rotate about a vertical longitudinal axis of the cranial recording chamber 6400 when resting upon the portion of the top 6420 of the cranial recording chamber 6400. One or more fasteners may be used to connect the sidewall 6346 of the chamber adapter 6300 to the portion of the top 6420 of the cranial recording chamber 6400 received within the recessed portion 6344.

Combined rotation of the chamber adapter 6300 about the main shaft 6320 and rotation of the chamber adapter 6300 relative to the top 6420 of the cranial recording chamber 6400 provides an area of candidate electrode positions. In some embodiments, the area of candidate electrode positions includes a generally circular area defined inside the cranial recording chamber 6400. The generally circular may have a diameter of about 12 mm. The area of candidate electrode positions may allow the operator to deploy the electrodes 6002 within the cranial recording chamber 6400 over multiple brain areas.

The electrodes 6002 may be disposed within a guide tube 6450 that is mounted inside the main body 6100. Referring to FIG. 13, the guide tube 6450 may include a bundle of longitudinally arranged tubes 6452. In one embodiment, each of the electrodes 6002 is disposed within a single tube 6454. The tubes 6454 may be constructed from stainless steel pieces of hypodermic tubing. The distal ends of the hypodermic tubing may be honed together to a sharp point.

After selecting a desired planar position from the candidate electrode positions within the cranial recording chamber 6400, the main body 6100 may be lowered with respect to the skull by manually turning the vertical lead screw 6322. The main body 6100 may be lowered until the tip 6456 of the guide tube 6450 pierces the dura, which is a tough layer of tissue protecting the brain. The guide tube 6450 may help protect the electrodes 6002. This gross vertical lowering of the electrodes 6002 is critical and can be challenging, as it is often difficult to tell when the dura has been pierced and lowering the guide tube 6450 too much may damage brain tissue. To this end, the microdrive 6000 was designed to maximize visual and tactile feedback during this operation. The design allows the operator a rough view of the point of insertion and includes clear vertical markings that show insertion depth.

Once the guide tube 6450 is in the correct position above the brain, the electrodes 6002 may be deployed, i.e., extended beyond the tip 6456 of the guide tube 6450, by activating the linear actuators 6200. As is apparent to those of ordinary skill, for semi-chronic use, structural elements may be locked into place with the various fasteners described above, and a cover (not shown) can be placed over the entire assembly for protection against impact and tampering by the subject.

The electrodes 6002 may be loaded by simply feeding the end 6004 (to avoid damage to the tip 6008) through the guide tube 6450 and affixing the end 6004 to the appropriate moveable carrier 6210. The microdrive 6000 may be cleaned by a simple bath in a disinfectant solution such as hydrogen peroxide.

Recently, the use of layered manufacturing technologies has been proposed to create functional robotic devices. See, e.g., J. G. Cham et al., "Fast and Robust: Hexapedal Robots via Shape Deposition Manufacturing," *Intl. J. Robotics Res.,* 21(10-11):869-82 (2002). In layered manufacturing, parts are not machined and assembled, but rather build up in layers by the repeated deposition of material unto a substrate. These processes allow parts to be created with nearly arbitrary geometry in relatively short amounts of time. Layered manufacturing processes include rapid prototyping technologies such as stereolithography (SLA) and 3D printing. Another layered manufacturing technology with potential for these types of applications, Shape Deposition Manufacturing (SDM), may allow active components such as actuators and sensors to be embedded within solid structures through its unique cycle of alternating material depositions and removal. See, e.g., J. G. Cham et al., "Layered Manufacturing with Embedded Components: Process Planning Issues," *ASME Proceedings, DETC '99*, Las Vegas, Nev., (September, 1999); R. Merz et al., "Shape Deposition Manufacturing," *Proc. of the Solid Freeform Fabrication Symposium*, University of Texas at Austin (August, 1994); and S. Rajagopalan, et al., "Representation of Heterogeneous Objects during Design, Processing, and Freeform Fabrication," *Materials and Design*, 22(3):185-97 (2000). Structures can be made that combine soft and hard materials in ways that mimic the elegant structures seen in nature.

One advantage of these processes is that they offer the ability to create compact designs that are not encumbered by fasteners or connectors or that require additional sealing between assembled components. Structures with complex geometry that would be impossible to make with traditional methods can be made as one solid piece. Other advantages include the relatively short time between design iterations and the ability to custom-modify each device to fit a particular patient or implantation site with relative ease.

The main body 6100, chamber adapter 6300, moveable carriers 6210, support member 6330, slider 6140, top cap 6350 may be constructed from a UV-curable plastic using an SLA process. Plastics available for the SLA process may have mechanical properties that approximate ABS plastic. If the plastic chosen flexes in high stress areas, the geometry of the components may be designed to reinforce those areas.

The SLA process used to construct some of the components of the microdrive 6000 may provide a layer thicknesses of about 0.1 mm. However, the finite beam size of the computer-controlled laser that solidifies the layers of the UV-curable plastic may cause the actual dimensions of the components to vary by approximately 0.1 mm from the specified value. In some SLA processes, with a limited choice of materials, the tolerance may be as low as 0.016 mm. These variations may pose a problem for the slider 6140 and lead screw 6322 mechanism for gross XYZ adjustment of the microdrive 6000. In this case, variations in the slider joint may cause play in the movement of the main body 6100, which may cause damage to the tissue when inserting the guide tube 6450 through the dura. To this end, these joints may be fitted with Teflon® bearing inserts. The fit of the Teflon® bearing inserts may be adjusted by one or more set-screws to achieve the desired joint precision and smoothness of motion when advancing the guide tube 6450.

The materials used in SLA processes are often not biocompatible. Parylene is the generic name for a family of thermoplastic polymers that can be deposited using room-temperature low pressure chemical vapor deposition (LPCVD). Parylene is known to be biocompatible (it is a US Pharmacy class-VI implantable material), and is commonly used for coating of biomedical devices such as pacemakers. Recently, its potential in creating MEMS neural probes and flexible connectors has been explored. See C. Pang et al., "A New Muhi-Site Probe Array with Monolithically Integrated Parylene Flexible Cable for a Neural Prosthesis," 27*th Intl. Conf of IEEE*, EMBS (2005).

The components made by the SLA process may be rendered biocompatible by coating them with Parylene. In one embodiment, a thin film of about 20 microns of Parylene was coated on the components constructed using the SLA processes. The layer of Parylene may be applied using a commercial LPCVD machine (Part number SCS PDS2010E, obtained from Labcoter).

Additional embodiments of the methods and systems can be envisioned by a person skilled in the art upon reading of the present disclosure and in particular the Examples section and will not be further described in details.

The following examples are provided to describe the invention in further detail. These examples, which set forth modes suitable for carrying out the invention, are intended to illustrate and not to limit the invention.

EXAMPLES

Example 1

Experiments with the Autonomous Algorithm 1000 and Commercially Available Microdrives In the first example, the embodiment of the autonomous algorithm 1000 implemented includes the state machine 2000. The current signal quality metric was determined by the SNR and the second signal quality metric was determined by the PTPA. The event vectors were aligned by their minimums and the first two principal components were used for feature extraction.

One embodiment of the autonomous algorithm 1000 was implemented in software using MATLAB®. The software can be used with any combination of microdrive (e.g., commercially available from Thomas Recording GmbH, FHC Inc., etc.) and data acquisition system (e.g., commercially available from Plexon Inc, Tucker-Davis Technologies, etc.) by writing MATLAB m-files for moving the electrodes and acquiring the data streams, as will be readily appreciated by those of skill in the art and as can be readily implemented by those of skill with only routine effort.

Figure 14:
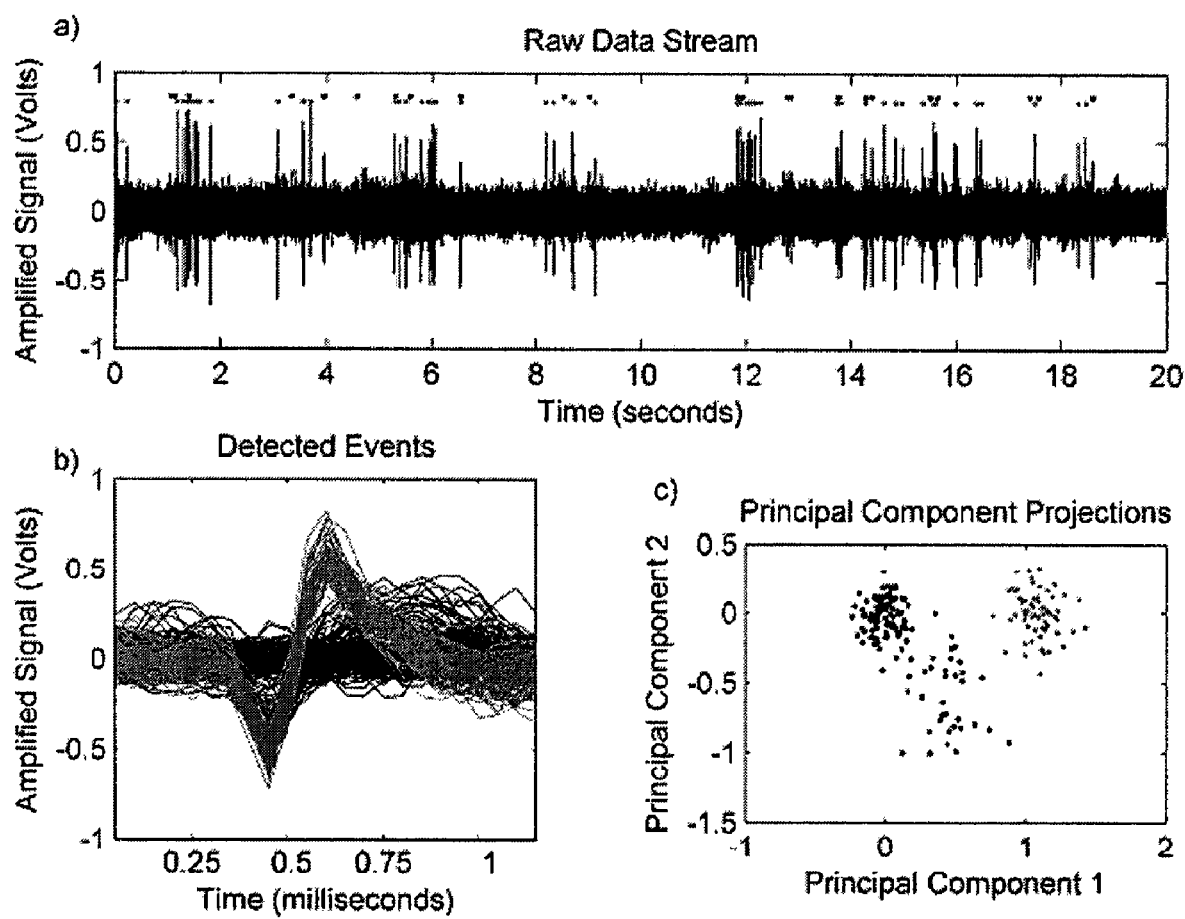
FIG. 14a depicts a visualization of a neural signal after it has been filtered by a high-pass (10 Hz) filter. The dots above the neural signal identify events (i.e., action potentials or spikes) detected by the method of FIG. 8(B).
FIG. 14b depicts the event vectors of the spikes detected aligned by their minimum. The black traces are random samples of noise. The finite mixture model used to cluster the event vectors has an order equal two, i.e., the event vectors have been categorized as originating from two distinct neurons.
FIG. 14c depicts projections of event vectors and noise samples on the first two principal components. The neuron firing the events shown in blue is not isolated, as its action potentials could be confused with noise fluctuations. The other neuron (in green) is far from the noise, but is not very well isolated as its action potentials could be confused with those in blue.

The testing of the inventive algorithm was performed using a single electrode microdrive (obtained from FHC Inc.; Bowdoinham, Me.) and a data acquisition system (obtained from Plexon Inc.; Dallas, Tex.). It is this system from which the results illustrated in FIG. 14 were obtained. FIG. 14A provides an example neural signal sampled using the Sample Neural Signal Module 1100. FIG. 14B provides a plurality of event vectors aligned by their minimums. The alignment was performed by the alignment portion of the Spike Classification Module 1300. The color of the event vector corresponds to the cluster to which it belongs. FIG. 14B shows an example action potential recordings (indicated by color green) from an isolated neuron and an example of action potential recordings (indicated by color blue) from a second neuron that cannot be reliably separated from signal fluctuations caused by noise. FIG. 14C provides an illustration of the results of the Spike Classification Module 1300.

The autonomous algorithm 1000 was also tested in other experimental systems; for instance, controlling a five-channel microdrive (obtained from Thomas Recording; Germany), a six-channel NAN drive (obtained from Plexon) and the three-channel microdrive described in Cham et al., "Semi-chronic motorized microdrive and control algorithm for autonomously isolating and maintaining optimal extracellular action potentials," *J. Neurophysiol.*, 93(1):570-579 (January 2005). Each of these systems uses a Plexon data acquisition system.

Figure 15:
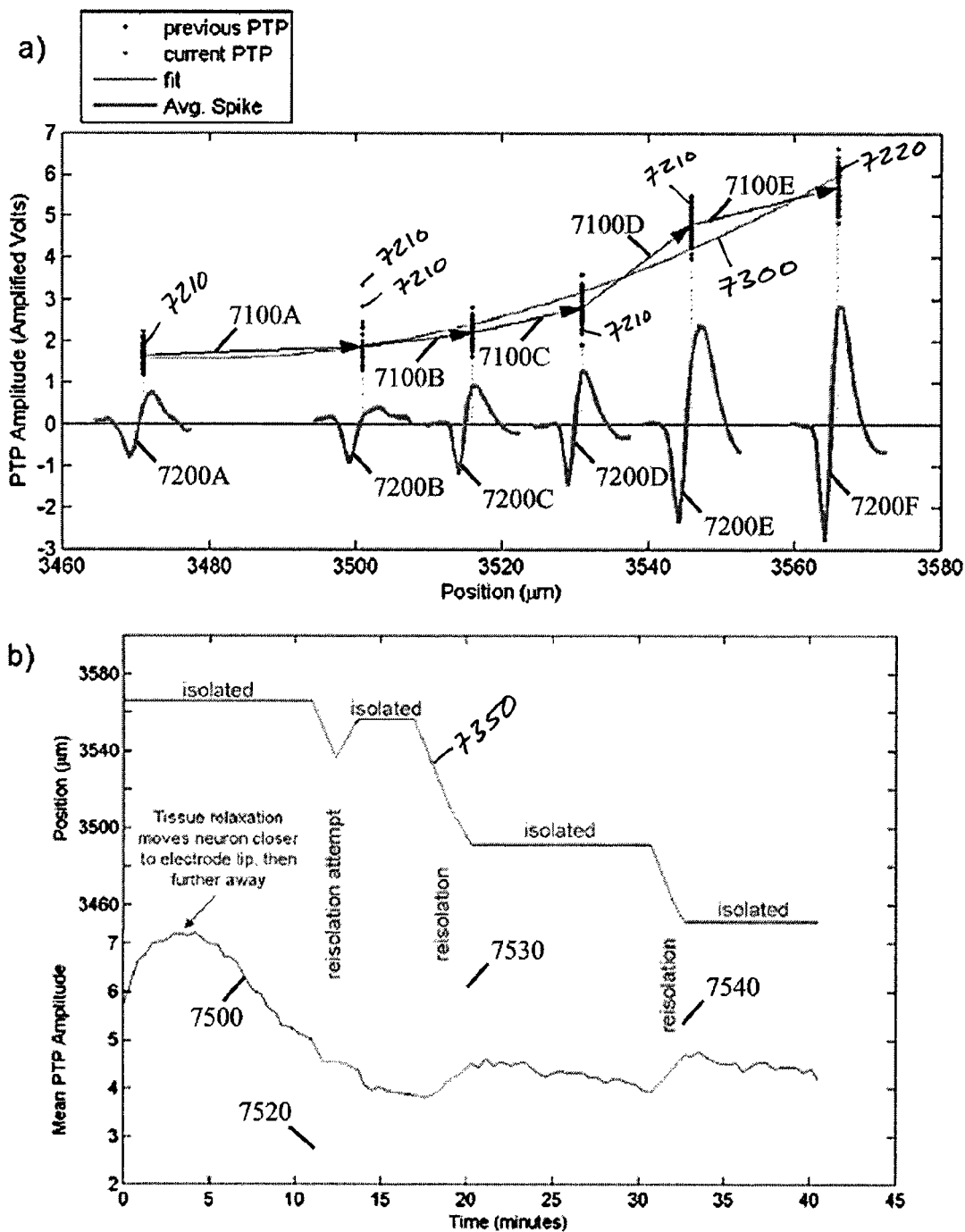
FIG. 15 shows the successful isolation of a neuron in a macaque parietal cortex in accordance with an embodiment of the present invention.

The autonomous algorithm 1000 has been used extensively to isolate and record dozens of neurons in the Posterior Parietal Cortex in rhesus macaque monkeys. FIG. 15A depicts the iterative results of the Model Isolation Curve Module 1500 as it moves the electrode 62 to the maximum of the estimated isolation curve 7000. The observations of peak-to-peak amplitude at each position are shown as black dots 7210 with the final observation as magenta dots 7220, the average action potential 7200A-F at each position in green, the modeled isolation curve 7300 in red, and the path of the electrode (always advancing in this example) by the black arrows 7100A-E. The action potential 7200A is probably from another neuron, observed before detecting the isolation curve of the isolated neuron. The autonomous algorithm 1000 stopped at the rightmost position because the signal quality was high enough that further movement was unnecessary and may damage the neuron.

FIG. 15*b* shows the maintenance phase of the isolation. Both the electrode position (blue) 7350 and the average peak-to-peak amplitude (red) 7500 are plotted against time. At time zero, the neuron is first isolated (which corresponds to the last observation shown in FIG. 15*a*). The signal improves and then degrades as the neuron drifts by the electrode 62. The non-horizontal portions of the electrode position plot 7350 depict periods during which the state machine attempted to re-isolate the neuron.

In FIG. 15B, changes in PTPA detected by the electrode 62 are plotted for a period of about 40 minutes. When the PTPA drops below the threshold "MIN_SNR," the autonomous algorithm 1000 transitions from the Neuron Isolated state 2500 and attempts to reisolate the neuron, i.e., the Resample Gradient state 2700 and possibly the Reisolate Neuron 2800 states is/are visited. The leftmost portion of the average peak-to-peak amplitude plot 7500 shows the neuron drifting—first towards the electrode 62 and then away. The first reisolation attempt fails and a new neuron is isolated in band 7520. It is believed that the first re-isolation attempt may have been unsuccessful because of excessive drift and/or electrode-tissue coupling. The new neuron is then successfully re-isolated twice in bands 7530 and 7540. This is a relatively short isolation example ended when the subject's behavior terminated the experiment. The results clearly demonstrate the effect of tissue drift and the success of the inventive autonomous algorithm 1000 in maintaining good signal quality. Many neurons have been held isolated for several hours using the inventive technique.

Example 2

An embodiment of the Microdrive 6000 with the Autonomous Algorithm 1000

Figure 16:
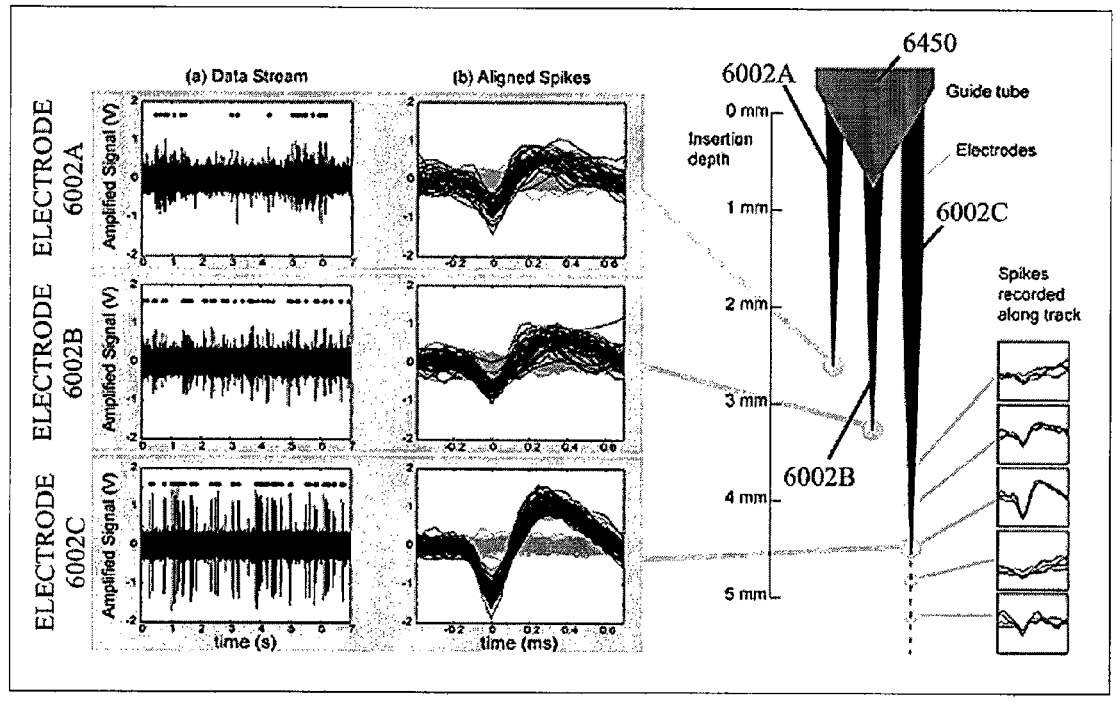
FIG. 16 shows simultaneous recordings of three neural signals using a microdrive including three electrodes 6002A-C in accordance with an embodiment of the present invention. Column (a) shows the raw filtered data stream, i.e., a visualization of each of the three recorded neural signals. Column (b) shows spikes detected in each of the neural signals after alignment using the method of FIG. 8(B). The diagram on the right shows the positions of the electrodes (drawn in relative scale) when the recordings of column (b) were made, as well as sample spike waveforms recorded along the trajectory of an electrode 6002C.

FIG. 16 illustrates neural data recorded using the Sample Neural Signal Module 1100 to simultaneously record neural signal from the three electrodes 6002A-C of the microdrive 6000. Graphs in column (a) plot several seconds of the filtered data stream over time, sampled at 20 kHz, with dots above the voltage trace at times when spikes (neuron action potentials) were detected. Column (b) shows close-up views of these detected spikes with their minimum voltage aligned at 0 ms. The spikes are underlaid by noise samples (in gray).

The diagram on the right side of FIG. 16 indicates the relative depths of the three electrodes 6002A-C at the time of the recordings. In the rightmost portion of FIG. 16 provides example action potentials recorded in consecutive depth positions of electrode 6002C are also shown near the depths at which they were recorded.

Figure 17:
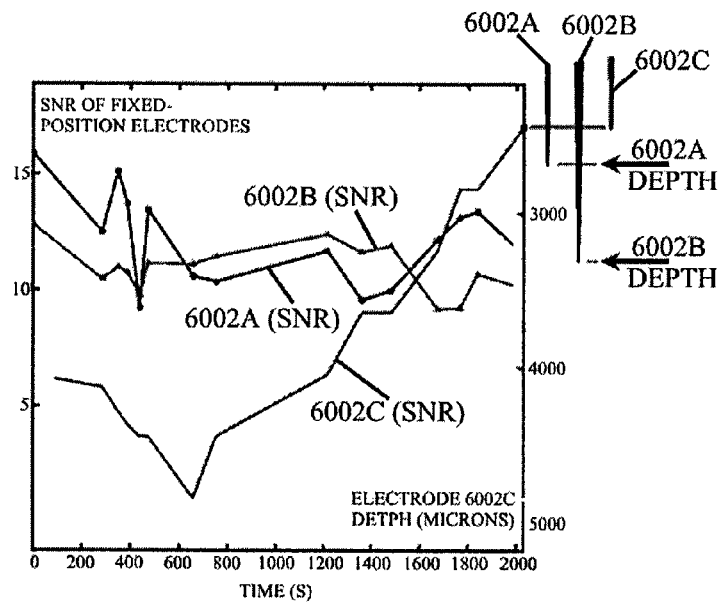
FIG. 17 shows the SNR recorded by the electrodes 6002A and 6002B plotted with the position of the electrode 6002C, in accordance with an embodiment of the present invention. The left vertical axis corresponds to the SNR ratio and the right vertical axis to the depth of the electrode 6002C. The horizontal axis corresponds to time measured in seconds.

Repositioning one electrode may shift the tissue around another electrode and inadvertently alter its signal. It is believed that this problem is dependent on the dimensions of electrodes and their spacing. The data shown in FIG. 17 represent an experiment aimed at investigating whether repositioning one electrode of the microdrive 6000 will shift the tissue around another electrode. In the experiment, the position (i.e., depth) of the electrodes 6002A and 6002B was held constant (each close to an active neuron). The electrode 6000C was then moved back and forth (at a speed of about 6 μm/s) and data streams were recorded on all three channels at each position.

First, the movement of the electrode 6000C caused no change in the position of electrodes 6000A and 6000B, as verified by the Hall effect sensors of the microdrive 6000. Next, the effects on the signals of electrodes 6000A and 6000B were inferred by looking for correlation between the signal-to-noise ratios (SNRs) of the signals and the position of electrode 6000C. From visual inspection of the data, no clear relationship between the SNR detected by the electrodes 6000A and 6000B and the position of electrode 6000C seems apparent. Only a general downward trend is observed in the SNR detected by the electrodes 6000A and 6000B, which does not correspond to the up and down motion of the electrode 6000C.

The downward trend in the SNR detected by the electrodes 6000A and 6000B over the recording period may be explained by gross tissue movement (e.g., relaxation following initial electrode advance). The trend is consistent with the frequently observed loss of signal quality due to tissue migration in acute experiments. See, e.g., J. G. Cham et al., "A Semi-Chronic Motorized Microdrive and Control Algorithm for Autonomously Isolating and Maintaining Optimal Extra-cellular Action Potentials," *J. Neurophysiol.*, 93:570-79 (2005). These initial results suggest that it is not a significant issue for the electrode separation in the microdrive 6000 (the centerlines of the electrodes 6000A-C are about 400 microns apart).

Example 3

Simulations Results Using the Autonomous Algorithm 1000

The autonomous algorithm 1000 was developed and tested in a simulated environment, whose details are described below. The application of the algorithm to acute neurophysiological recording experiments is discussed as well as its potential implication to chronic recording electrode arrays. The autonomous algorithm 1000 may be useful for both acute, chronic, and semi-chronic extracellular recordings.

Modeling Extracellular Potential

The inventors developed a detailed computational model of the extracellular field around a neuron for several reasons. Due to the complex nature of the problem, it was helpful to initially test and develop the autonomous algorithm 1000 on a simulator. Second, this model provides a biophysical basis for the inventive control methodology. Additionally, with this model the inventors were able to simulate the recording electrode positioning processes in a repeatable and reliable way.

The simulator includes two components. In the first component, the inventors solve for the time-varying membrane currents using a detailed compartmental model of a neuron. In the second component, these currents were used as boundary conditions for a partial differential equation (PDE) that models the propagation of the extra-cellular potential.

Computational Model of a Single Neuron

A model of a neocortical pyramidal cell from layer 5 of the cat visual cortex was used for simulations. See Z. Mainen et al., "Influence of dendritic structure on firing pattern in model neocortical neurons," *Nature*, 382:363-66 (1996). This model was selected mainly because of its ability to emulate firing properties of real cortical cells. Nothing about the autonomous algorithm 1000 depends upon the specific properties of this model. A brief account of the model is given here for the convenience (see Id. for details).

The model is developed in the NEURON simulation environment. See M. Hines et al., "The neuron simulation environment," *Neural Comp.*, 9:1179-1209 (1997). It consists of 3720 compartments and captures the complex geometry of the dendritic tree. The model has a low density sodium ($Na^+$) channels in the soma and dendrites and a high density in the axon hillock and initial segment. Fast potassium ($K^+$) channels are present in the axon and soma, but are excluded from the dendrites. This type of channel distribution is responsible for spike initiation at the axon initial segment. See Z. Mainen et al., "A model of spike initiation in neocortical pyramidal neurons," *Neuron* (1995). To ensure repetitive firing, slow K$^+$ channels were added to the soma and dendrites, along with one type of high-threshold calcium (Ca$^{2+}$) channel. In the original model, the neuron was activated by injection of current in the soma. The inventors' model is based on a modification made by Holt, where the injected current in the soma was replaced with synapses uniformly distributed throughout the dendrites. See G. Holt et al., "Electrical interactions via the extracellular potential near cell bodies," *J. Comp. Neurosci.*, 6:169-84 (1999).

The cable equation, a PDE describing the voltage changes as a function of time and space, is typically used as the basis of compartmental neuron models. Depending on the number of assumptions made in the modeling process, the cable equation can be developed at different levels of complexity. Only final results are presented herein. A detailed derivation of the results from the first principles and underlying assumptions can be reviewed at G. Holt, "A critical reexamination of some assumptions and implications of cable theory in neurobiology," Ph.D. dissertation, California Institute of Technology (1998).

In summary, the electric potential in the space in and around the neuron is governed by a system of Laplace equations, as described below in system (13), with the boundary conditions $\sigma_i \nabla \phi_i n_i = J_m$ and $\sigma_e \nabla \phi_e n_e = J_m$ where $\phi_i$ and $\phi_e$ are the intracellular and extracellular potential (respectively), $\sigma_i$ and $\sigma_e$ are the corresponding conductivities per unit length, $n_i$ and $n_e$ are normal vectors to the cell membrane ($n_i = -n_e$), and $J_m$ is the transmembrane current per unit area. The time constants for the extracellular and intracellular space are much smaller than those of an active membrane; hence, both the extracellular and intracellular space are almost purely resistive and no time derivatives appear in system (13).

$$\nabla^2 \phi_i = 0 \nabla^2 \phi_e = 0, \tag{13}$$

For a neuron with complex dendritic structure, system (13) is virtually unsolvable. Most neural simulators assume one-dimensional intracellular space and a weak coupling from extracellular to intracellular potential (effectively $\phi_e = 0$). Under these conditions, the $\phi_i$-part of the system (13) can be viewed as a 1-D PDE driven by the dynamics of the active membrane. This PDE is then solved numerically by converting it to a system of ordinary differential equations through a compartmental modeling process, wherein, for each compartment, there is a membrane equation: $c_m d\phi_i(t)/dt + g_m(\phi_i(t) - E_m) = i_m(t)$, where $c_m$, $g_m$ and $i_m$ are the membrane capacitance, conductance, and current per unit length, respectively, and $E_m$ is so-called reversal potential. Once $\phi_i$ and $J_m$ are known for each compartment, it is possible to solve for $\phi_e$.

Line Source Approximation

Figure 18:
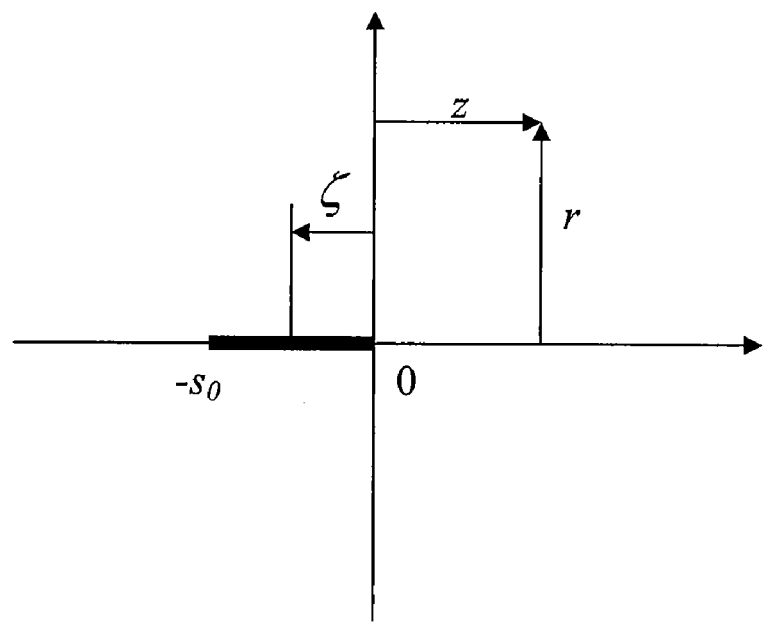
FIG. 18 shows a line source approximation for a single segment with length $s_0$, in accordance with an embodiment of the present invention.

Despite existing numerical routines for solving PDEs, the complexity of the boundary condition renders the solution of the $\phi_e$-part of system (13) prohibitively expensive. An approximation has been developed that gives a fast and relatively accurate solution. See G. Holt et al., "Electrical interactions via the extracellular potential near cell bodies," *J. Comp. Neurosci.*, 6:169-84 (1999). Assuming current is generated at a point source in an unbounded isotropic volume, $\phi_e(r,t) = I(t)/(4\pi\sigma_e r)$, where I is the source current and r is the distance to the source. Furthermore, if the thickness of the compartmental model segments is neglected, each segment can be treated as a continuous line of point sources. For a single line segment, the potential at a point (r, z) due to this line source approximation is $$\phi_e(r, z, t) = \int_{-s_0}^{0} \frac{i_m(\zeta, t) d\zeta}{4\pi\sigma_e \sqrt{r^2 + (z - \zeta)^2}} \tag{14}$$

where $i_m$ is the transmembrane current per unit length, r is the distance to the line, z measures distance in the direction of the line underlying the segment, and $-s_0$ and 0 are the endpoints of the line segment in a local coordinate system attached to the segment (see FIG. 18). Note that this approximation implies a radial symmetry of the extracellular potential $\phi_e$. Moreover, for a fixed time t, the transmembrane current is constant along the segment ($i_m(., t) = i_m(t)$) and the solution to Eq. (14) can be found in a closed form. The exact form of this solution and the accuracy of the line source approximation for this particular model are discussed in G. Holt, "A critical reexamination of some assumptions and implications of cable theory in neurobiology," Ph.D. dissertation, California Institute of Technology (1998). At a fixed time, the potential at any point in the extracellular space is found by summing the contributions of all line segments (line source approximation) and soma (which is modeled with a point source approximation).

Modeling Noise Field

Noise was added to the model in order to mimic experimental conditions. Voltage fluctuations (thermal noise) in the recording electrode are a major source of uncertainty. Additional noise sources arise from the recording hardware. The activity of neurons relatively distant from the recording site imposes biological noise. See, e.g., R. Lemon, Methods for Neuronal Recording in Conscious Animal, Wiley (New York), ch. 2, pp. 17-38 (1984). Because these signals fall below the noise level, they cannot be utilized for further study and are treated as noise rather than useful signals. The process of analog-to-digital conversion imposes an amplitude quantization noise.

In the simplest scenario, the observed signal z can be viewed as a useful signal s corrupted by an additive noise w (i.e., $z(t) = s(t) + w(t)$), where w subsumes various noise sources such as the electrical noise, the biological noise, the quantization noise, etc. To model noise w properly, the inventors made the following observations. First, neural noise is non-stationary (i.e., its statistical properties change over time). The non-stationarity of neural noise has been reported on time scales as small as 20 ms. See M. Fee et al., "Variability of extracellular spike waveforms of cortical neurons," *J. Neurophysiol.*, 69:175-88 (1996). Second, the distribution of neural noise is non-Gaussian. Several studies have found that the density of neural noise has heavier tails (super-Gaussian) than the normal density. See, e.g., Id., M. Sahani, "Latent variable models for neural data analysis," Ph.D. dissertation, California Institute of Technology, 1999, and M. Lewicki, "Bayesian modeling and classification of neural signals," *Neural Comp.*, 6:1005-30 (1994). Furthermore, neural noise exhibits significant time correlations with so-called 1/f spectra (ignoring, for the moment, an apparent paradox of the spectra of non-stationary processes). These processes, termed 1/f processes, arise in many physical applications and their spectra obey $S(f) \propto |f|^{-p}$ over a wide range of frequencies, where p>0 and p is not necessarily an integer. Since 1/f processes are not adequately handled with linear models, such as autoregressive moving average, various modeling attempts have been made in the past, although no general solution exists to date.

Figure 19:
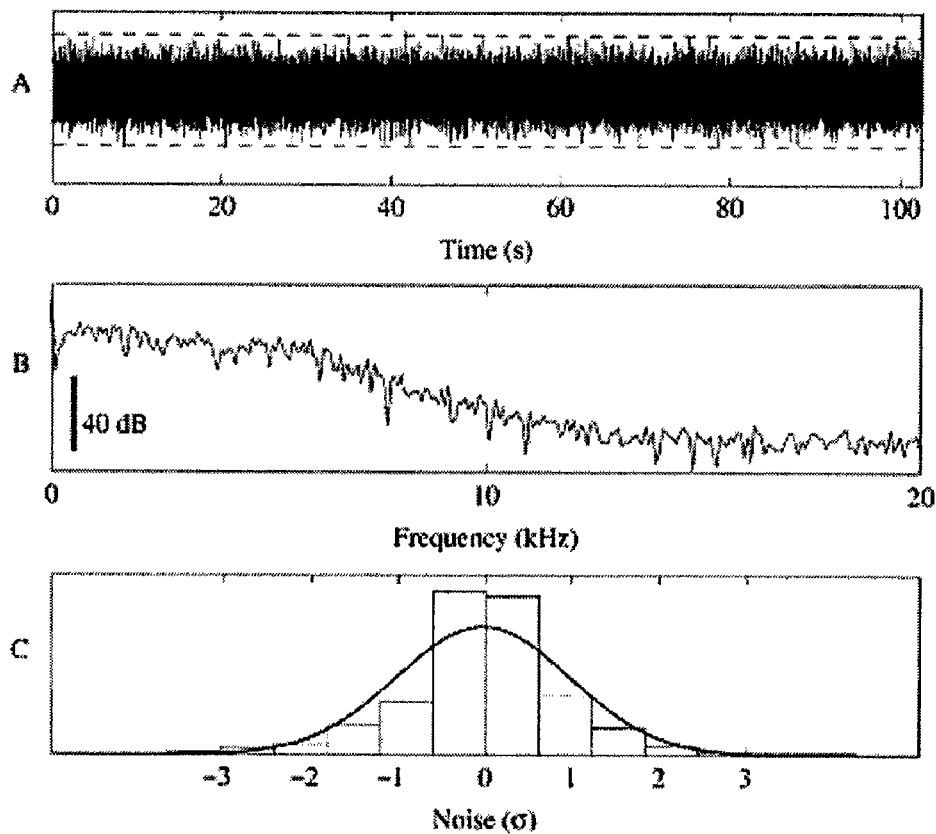
FIG. 19(A) shows a visualization of typical background noise recorded in a primate cortex, i.e., a recorded neural signal containing no visible spikes. The dashed lines mark the $4\sigma$ bounds, i.e., the upper and lower dashed lines represent two standard deviations from the mean.
FIG. 19(B) shows the power spectral density of the recorded noise of FIG. 19(A) with a characteristic 1/f behavior.
FIG. 19(C) shows a histogram of the recorded noise of FIG. 19(A) together with a plot of a Gaussian probability density function whose mean and variance are equal to the sample mean and sample variance of the recorded noise.

To avoid these problems and to take advantage of recorded data at the inventors' disposal (a single platinum-iridium microelectrode (Frederic Haer Company, Bowdoinham, Me.) with the nominal impedance of 2 MΩ at 1 kHz was used for the recording; the electrode was advanced manually using a commercial micromanipulator (Narishige International USA, Inc., Long Island, N.Y.); the data was acquired through a recording system (Plexon Inc, Dallas, Tex.) with a preamplifier and a band-pass filter (band 154 Hz-13 kHz); and the signals were amplified and digitized (12 bit A/D converter, digitization rate 40 kHz) by a data acquisition card PCI-MIO 16E-4 with LabView (National Instruments, Austin, Tex.)), the inventors sampled neural noise from the Rhesus parietal cortex recordings that did not yield any visible spikes. This noise, referred to as "recorded noise," is non-stationary, non-Gaussian and contains all the noise sources listed above. These properties together with the abundant number of sample paths that can be drawn from recorded data, make the recorded noise a suitable noise candidate for the present computational model. A sample path of the recorded noise, its power spectral density and histogram are shown in FIG. 19.

The "modeling" of the noise w is completed by scaling the recorded noise so that a specific standard deviation $\sigma_w$ is met. Consistent with typical noise levels in extracellular recordings, the inventors selected $\sigma_w$=20 µV for the study. Furthermore, as the noise amplitude (peak-to-peak) easily reaches five $\sigma_w$ (see FIG. 19), most of the traces outside the 120 µm sphere cannot be reliably detected. This confirms the findings of many studies, and additionally justifies the inventors' choice of $\sigma_w$.

Although the inventors "model" neural noise as a non-stationary non-Gaussian process, exactly the opposite was assumed for purposes of analysis and algorithm development. The rationale is that: (a.) the analytical tools for mathematical treatment of non-stationary processes are not well developed, which makes their analysis cumbersome, and (b.) Gaussian assumption usually provides tractable calculations often resulting in a closed form analytical solution. The downside is that the violation of these assumptions generally produces suboptimal solutions. However, the algorithm is sufficiently robust with respect to the violation of these assumptions. The success of the algorithm in an experimental environment points to a similar conclusion. The inventors define a signal-to-noise ratio ("SNR") as the energy contained in a spike signal divided by the expected noise energy. For a zero-mean wide sense stationary noise with variance $\sigma_w^2$, this definition reduces to:

$$SNR \triangleq \frac{\text{RMS}(s)}{\sigma_w} \quad (15)$$

where RMS(s) is the root-mean-square value of s calculated over the supporting time interval of a single spike.

Simulations

The autonomous algorithm 1000 was tested in the simulated environment. To test the autonomous algorithm 1000 in a multi-unit context, the inventors simulated the extracellular potential of two neurons that were assumed to be decoupled. In this manner, the extracellular potential field is simply a superposition of the fields induced by the two simulated neurons.

The two identical neuron models are placed in parallel without any rotation (see FIG. 20A) to mimic the parallel organization of the neurons in cortical columns. In a local coordinate system with µm units, the somata of neuron 1 and neuron 2 are centered at (0,0,0) and (50,0,0), respectively. Rotation of the neurons 1 and 2 around y-axis did not significantly affect the results. The 50 µm distance between the somata is consistent with the wide range of cell densities in the cerebral cortex. To account for complex non-linearities in the kinetics of voltage-gated channels, the simulations were carried out with variable step size in NEURON. The step size varied between 0.02 ms during the steep rising phase of action potentials and 1.0 ms during the steady state phase. See G. Holt, "A critical reexamination of some assumptions and implications of cable theory in neurobiology," Ph.D. dissertation, California Institute of Technology, 1998. The firing rate of the neurons was estimated at 58 Hz.

While the extracellular simulator can work at an arbitrary sampling rate, the inventors found a rate of 20 kHz a good compromise between computational speed and accuracy of spike representation. Thus, the transmembrane currents were re-sampled at 20 kHz in MATLAB®. The choice of re-sampling method did not cause any significant differences in the results, hence a linear interpolation was used. The inventors imposed an 8 ms phase shift between the responses of the two neurons to prevent them from firing simultaneously.

The location of the neurons was determined using the following tissue movement model. The extracellular potential of the two neurons was calculated as a superposition of the potentials of individual neurons which were obtained as described above.

Modeling Tissue Movement

The nature of neural tissue movement caused by the movement of a recording electrode is not well understood. The understanding of the overall process likely involves a complex mechanical analysis. Based on some basic observations, the inventors developed a simple model of tissue movement. The purpose of this model is not to capture the complexity of the tissue dynamics, but rather to perturb the neuron's position so that the autonomous algorithm 1000 can be tested against these types of disturbances, which are commonly found in acute extracellular recordings.

It is believed that the movement of neural tissue in response to electrode movement has two significant time scales: fast and slow. Due to friction forces, even the sharpest electrode will cause tissue compression as the electrode is advanced through the neural tissue. The time scale of these movements is short (seconds and minutes). Presumably, the energy stored through the tissue compression is released through subsequent relaxation, which is a much slower process (time constant ½-1 hour). While the fast (transient) tissue movements are more relevant for the convergence of the autonomous algorithm 1000 (such as may occur during the Optimize state 4200 depicted in FIG. 7), the slow (relaxation) movements are more relevant for the stability of the optimal solution (such as may occur during the Maintain state 4300 depicted in FIG. 7).

Figure 21:
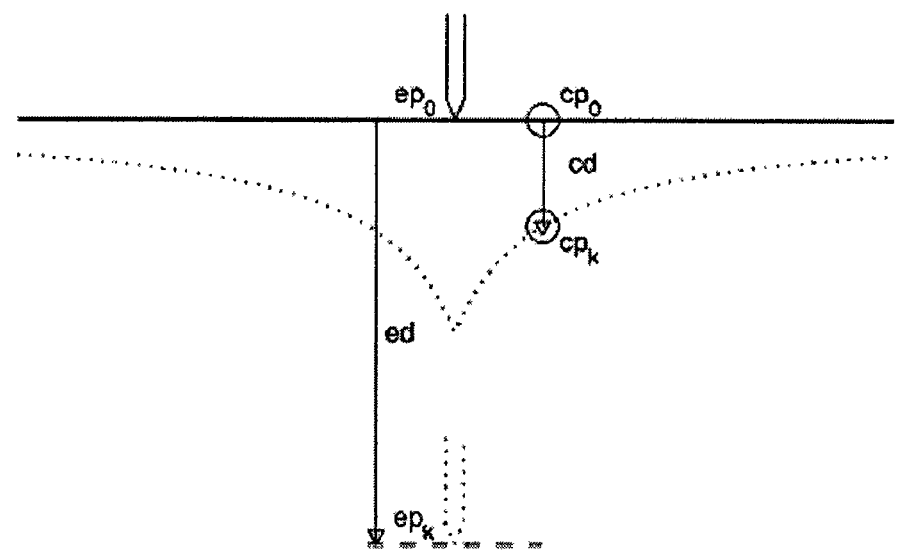
FIG. 21 shows a diagram illustrating tissue movement or migration of a neuron relative to the movement of an electrode. The diagram depicts an initial position (solid line) and the position at iteration k (dotted line) of the electrode and neuron. Neurons farther from the electrode's path of travel may undergo smaller displacement.

Let $ep_k$, $cp_k \in R^3$ denote the position of the electrode tip and the position of the neuron (its soma center) at iteration k={0, 1, ··· }, respectively. The inventors assume that all the segments of the neuron undergo the same displacement which is proportional to the electrode displacement, i.e.

$$cp_k = cp_0 + \alpha g(ep_k - ep_0)\exp(-k/T) \forall k = \{1,2,\Lambda\} \quad (16)$$

where $\alpha$ is a proportionality constant, g is a gain factor and T is a time constant of the tissue relaxation. Let k* be the iteration at which the convergence is attained. Since k*<<T, for transient tissue movements (k≤k*), the last term in Eq. (16) can be ignored. In this case, cd=a g ed, (see FIG. 21), where $$cd \triangleq cp_k - cp_0 \text{ and } ed \triangleq ep_k - ep_0$$

are the neuron displacement and the electrode displacement, respectively. Under the assumption that the neurons closer to the electrode path are affected by the electrode displacement more than the neurons that are further away from the electrode path, the following expression may be written:

$$\alpha = \frac{d}{d+r}$$

where r is the distance between the center of the soma and the electrode track, and d is suitably chosen constant. For example, $\alpha=1$ if the center of the soma lies directly in the electrode path, and $\alpha$ approaches 0 for the neurons that are far away from the electrode track (see FIG. 21). The rate of the decay of a is regulated by the constant d (d=10 μm for this study). The gain factor $g \in (0,1)$ determines what fraction of the electrode displacement translates into the neuron displacement (g=0.9 for the present study). For example, the displacement of electrode by 100 μm, causes the displacement of 30 μm of the neuron with a soma center that is located 20 μm from the electrode path.

For relaxation movement (k>k*), $cp_k=cp_0+cd^* \exp(-k/T)$, where cd* is a constant vector defined as $cd^*=\alpha g(ep_k^*-ep_0)$. For very large k, the tissue relaxes back to its original position, i.e. $cp_k \rightarrow cp_0$. For the present study, the inventors chose T=300, which given the fact that a single iteration takes ~5 s, translates into a time constant of 25 min.

Due to relatively high firing rates, one second of the simulated neural signals provided enough spikes for successful post-processing (e.g. clustering and objective function evaluation). A one-second subset of the recorded noise seen in FIG. 19A was selected at random, re-sampled at 20 kHz, scaled to $\sigma_w=20$ μV, and added to the simulated neural signals.

Definition of Sampling Tracks

The performance of the autonomous algorithm 1000 was tested in simulation along many transects, including the two principal directions seen in FIGS. 20B and 20C. In the local coordinate system of the neurons, these two directions are parallel to z-axis and y-axis, and will be termed the vertical direction and the horizontal direction, respectively. These two sampling directions mimic the process of recording from a sulcus and regular cortical layers, as shown in FIGS. 20D and 20E. As shown in FIGS. 20B and 20C, the inventors simulated several individual sampling tracks along each of these two principal directions. These tracks are numbered, with the tracks in FIG. 20B representing vertical sampling tracks, while those in FIG. 20C depict the location of horizontal sampling tracks. The tracks of the vertical and horizontal directions start in a plane located at z=100 and y=80, respectively.

To obtain statistically significant results, 100 trials were performed for each sampling track. The allowed range of motion of the "electrode" was $z \in [100,-100]$ for vertical tracks and $y \in [80,-20]$ for horizontal tracks. These values are consistent with a relatively small field of the detectable potentials of the model neuron. They may also reduce the time the autonomous algorithm 1000 spends in the Search state 4100 (see FIG. 7), thereby lowering the computational overhead of individual trials. If the autonomous algorithm 1000 did not converge to a solution within these ranges, the trials were aborted and declared unsuccessful. Depending on their position relative to the neurons, individual tracks exhibited a wide range of SNRs, where the SNR was defined as:

$$SNR \triangleq \frac{\text{RMS}(s_1) + \text{RMS}(s_2)}{2\sigma_w} \quad (17)$$

This modification of the definition in Eq. (15) accounts for the presence of two neurons. Because both neurons have the same firing rates, the two RMS values are weighted equally.

Choice of Parameters

The autonomous algorithm 1000 may involve several parameters and spike processing methods, and its performance may depend on a particular choice of these parameters and methods. The choice of parameters and methods used in the analysis that follows, is provided by Table I. The inventors have found that as long as the parameters are chosen reasonably, the autonomous algorithm 1000 may offer consistent performance. This is particularly true for parameters related to model selection, e.g. $k_0$, N, and $N_G$.

TABLE I

THE CHOICE OF PARAMETERS AND METHODS USED FOR PRESENT ANALYSIS.

| Variable/Operation | Value/Type |
|---|---|
| [$W_{min}$, $W_{max}$] (spike width) | [0.5, 1.0] ms |
| L (detection sensitivity) | 0 |
| $N_f$ | 2 |
| Feature Extraction | Haar Wavelet |
| $N_G$ | $\begin{cases} \lfloor \log_2 N_s - 1 \rfloor, & N_s \geq 4 \\ \{0\} \text{ no clustering}, & N_s < 4 \end{cases}$ |
| N | 5 |
| $k_0$ | 6 |
| C | 1 |
| Tol | 0.5 μm |
| $\Delta_s$ | 25 μm |
| $\Delta$ | 5 μm |
| $\Delta_{max}$ | 10 μm |

Performance of the Algorithm

Because the electrode 62 and the neurons are movable, an efficient way to test the performance of the autonomous algorithm 1000 is to measure how close the electrode 62 comes to the dominant (closest) neuron upon convergence (at iteration k*) and compare this distance, denoted by $d_{k^*}$, to an optimal distance, d*, across trials. The optimal distance d* was calculated off-line through a brute force numerical search over the sampling track using very fine (1 μm) sampling steps. To eliminate the dependence of the solution on the electrode movement, the neuron coordinates remained fixed during the simulation of the Search State 4100. At each sampling location, one second of data is simulated and the spikes corresponding to the dominant neuron used to obtain the second signal quality metric. The second signal quality metric was defined as the PTPA. Because the precise occurrence times of the spikes from the two neurons were known exactly, no detection, alignment or clustering was necessary. This eliminates error due to false detection, misclassification, etc., and ensures that the second signal quality metric evaluation is error-free. The regression function M(u) was estimated as the sample average of the second signal quality metric and its maximizer u* was found. At the point u*, the optimal distance d* was found as the distance between the electrode tip and the soma center of the dominant neuron.

Figure 22:
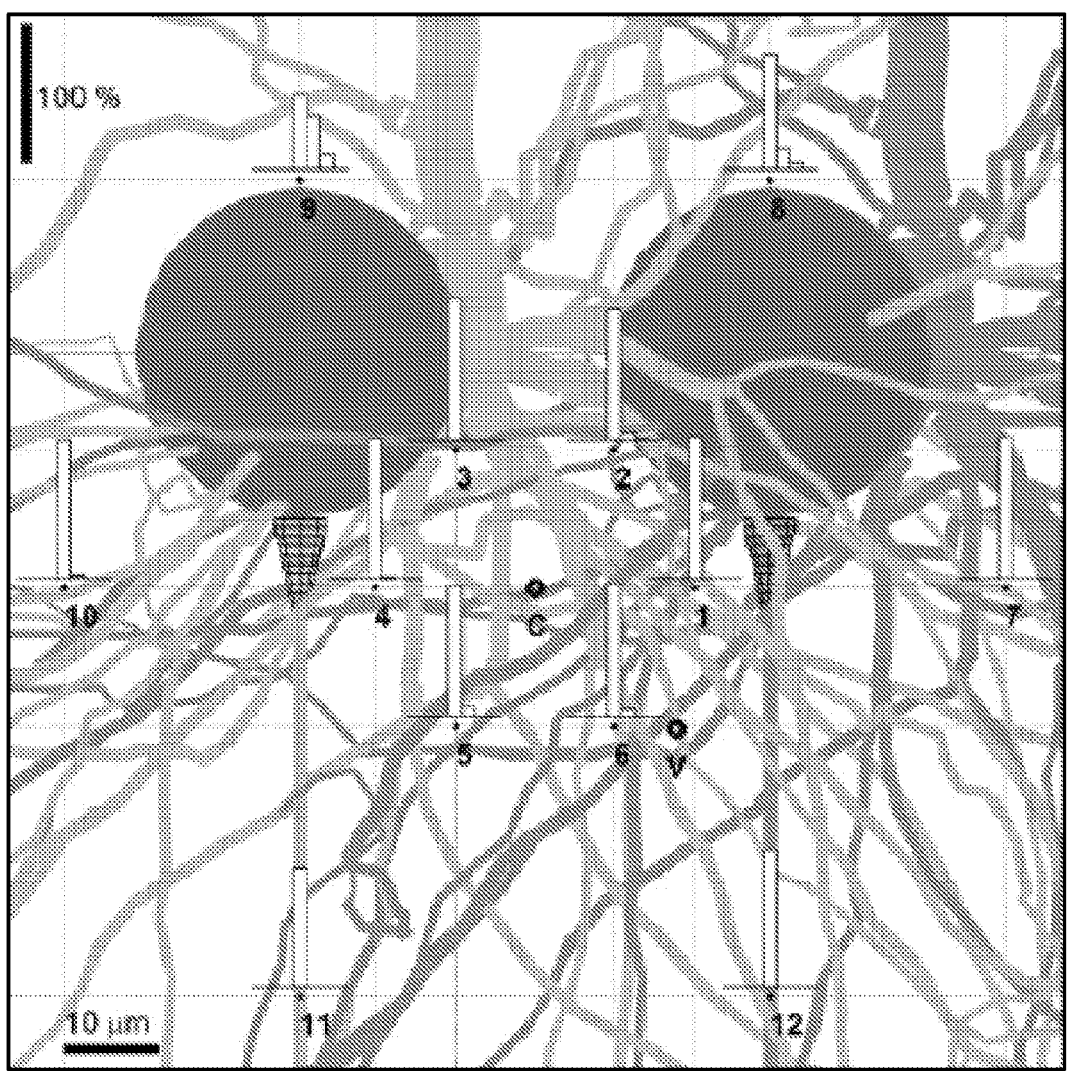
FIG. 22 shows a histogram having a bin size of about 8 μm of error $$\varepsilon \triangleq d_{k^*} - d^*$$

Referring to FIGS. 22 (for vertical tracks) and 23 (for horizontal tracks), the majority of the solutions place the electrode tip within 4 μm of the optimum d*. Not surprisingly, the performance degrades for sampling tracks that are farther from the axon hillock, such as V8 and V9, which exhibit relatively modest levels of SNR. Also, it appears that the termination condition (Tol=0.5 μm) was too large for these particular tracks, and that more consistent performance could be obtained at the expense of lowering Tol. On the other hand, the tracks V11 and V12 had even lower levels of SNR, yet they offered more consistent performances than the tracks V8 and V9. However, these two tracks did not achieve a 100% success rate (defined as a percentage of convergent trials), in particular a success rate of 84% and 97% was observed at V11 and V12, respectively. Additional analysis of unsuccessful trials showed that these tracks had critically flat regression functions. Coupled with low SNR this resulted in incorrectly estimated regression function model $\hat{M}^{(k)}(u)=b^*_{1,k}$, $\forall k > k_0$, which has no maximum and thus prevented convergence.

Similar behavior was observed for the tracks H5 and H6, which had 54% and 92% success rate, respectively. Additionally, the convergence rates of these sampling tracks were lower than those of the fully successful sampling tracks. For example, the average number of iterations k* necessary to reach the optimum for the tracks V11 and V12 was about 16.25 and about 15.56, respectively, versus about 13.15 iterations for the tracks V1-V10. Similarly, the average number of iterations k* was about 21.25 and about 19.00 for the tracks H5 and H6, respectively, versus about 15.56 iterations for the tracks H1-H4.

Once the optimal position u* is found, the autonomous algorithm 1000 tracks the neuron by monitoring the deviations of the second signal quality metric from the found optimum. FIG. 24 shows a typical course of a simulation where the optimal signal quality is maintained over a period of more than 900 iterations. The sampling track, denoted by "V" in FIG. 22, ran vertically approximately 40 μm away from the soma of neuron 2. The initial position was set 200 μm above the horizontal plane passing through the two somata. After several iterations in the Search state 4100 (see FIG. 7), spikes were found and the autonomous algorithm 1000 transitioned to the Optimize state 4200 (see FIG. 7).

At iteration k=21 the optimum position u*~235 μm was found and the autonomous algorithm 1000 transitioned to the Maintain state 4300 (see FIG. 7). Note that if the neurons were stationary, u*~200/μm is expected to be the optimal position. This discrepancy may be mostly a consequence of the transient neuron movement, which was modeled as described above.

In the Maintain state 4300 (see FIG. 7), the current signal quality metric was monitored and compared to the mean of the current signal quality metric of the signal acquired at iteration k*. Due to slow (relaxation) tissue movements, the observed current signal quality metric degraded over time. Once the deviation in signal quality exceeded pre-specified tolerance (in this study, chosen as three standard deviations of the optimal signal quality at iteration k*), the optimality was considered lost, and all the previous signal quality observations were cleared. The autonomous algorithm 1000 transitioned back to the Optimize state 4200 (see FIG. 7) and a new optimum was found. The optimality was then maintained by toggling between the Maintain and Optimize states 4300 and 4200 (see FIG. 7). The frequency of switching between the Maintain and Optimize states 4300 and 4200 may depend on how tight the tolerances are set. As the number of iterations increased, the neurons drifted closer to their initial position and the autonomous algorithm 1000 remained in the Maintain state 4300 for longer periods of time. At the same time the newly found optima approached the point u*=200 μm. The average signal quality, however, remained essentially unchanged over different optima, as can be seen in FIG. 24.

Based on the realistic model of extracellular potentials described above, the inventors determined the autonomous algorithm 1000 may autonomously find the optimal recording position along a linear sampling track and maintain the optimality of the solution by compensating the disturbances due to modeled tissue movements.

The remarkable success rates depicted in FIGS. 22 and 23 are somewhat expected given the regularity of the responses of the two simulated neurons. Such highly repeatable firing patterns are rarely found in actual recording experiments. Instead, the activity of individual neurons could be highly non-stationary, ranging from sporadic firing (less than a few Hz) to fairly high firing rates, often related to the task performed by the animal subject. Observing signals for a few seconds may not be sufficient to adequately estimate the signal quality metric. However, as the examples above show, this algorithm has behaved well in actual use with awake behaving animals.

For example, in a successful implementation of the autonomous algorithm 1000 in acute single-electrode recording experiments involving both rats and monkeys, the firing rate was typically very low (a few Hz) and up to 20 seconds of data at a single electrode position was necessary to correctly perform unsupervised clustering and in turn correctly estimate the signal quality metric. See J. G. Cham et al., "A Semi-Chronic Motorized Microdrive and Control Algorithm for Autonomously Isolating and Maintaining Optimal Extracellular Action Potentials," *J. Neurophysiol.*, 93:570-79 (January 2005). Clearly, a neuron with an arbitrarily low firing rate can be tracked, but this may result in a large amount of the data to be processed, which invariably slows down all the computational steps and the time necessary for the autonomous algorithm 1000 to converge. This trade-off can be practically handled by setting a lower bound for the firing rate of the neuron to be tracked, for example, a bound of 2 Hz was used in the previously cited article.

Another practical issue arises when an electrode comes too close to the membrane of a neuron, which may damage the neuron and cause its subsequent death. This phenomenon is often concurrent with the observations of extremely large action potentials. One way to handle this situation is to constrain the optimization algorithm to stop when the signal quality metric exceeds some suitably chosen upper bound. For example, an upper bound of SNR=12 was used for the experiments in the previously cited article. Likewise, solutions with poor signal quality should be abandoned despite optimality. For example, the solutions at tracks VI 1, V12, H2, H3, H5, and H6 would probably be of very little practical use because of extremely low SNR that they provide.

The successful use of the autonomous algorithm 1000 in acute recording experiments may significantly improve the productivity of recording neuroscientists by freeing them from the tasks such as manual positioning and frequent readjustments of the electrodes 62. The role of operator may be reduce to the off-line selection of parameters similar to those of Table I by a software implementation of the autonomous algorithm 1000.

While the methods and systems have been described in terms of what are presently considered to be particular embodiments. It is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the claims.

What is claimed is:

1. A method of automatically positioning an electrode disposed inside a brain, the method comprising:
    moving an electrode along a predetermined path of travel until a neural signal having a current signal quality metric that is greater than or equal to a minimum threshold value and comprising action potentials is detected;
    after the neural signal is detected, moving the electrode to a plurality of locations along the predetermined path and after each move, recording a sample of the neural signal;
    detecting, carried out by a processing means, action potentials in the neural signal of each of the recorded samples;
    classifying, carried out by a processing means, the action potentials of each of the recorded samples into classes;
    calculating, carried out by a processing means, a first signal quality metric for each of the classes;
    for each of the recorded samples, identifying, carried out by a processing means, a dominant class;
    for each of the action potentials of the dominant class of each of the recorded samples, determining, carried out by a processing means, a second signal quality metric;
    modeling, carried out by a processing means, an isolation curve as a function of the second signal quality metric for each of the action potentials of the dominant class of a first portion of the recorded samples and the locations of the plurality of locations where each of the recorded samples of the first portion of the recorded samples were recorded;
    determining, carried out by a processing means, a move distance from a current electrode position to a location along the modeled isolation curve that the modeled isolation curve indicates will improve signal quality; and
    as long as the move distance is greater than a predetermined minimum move distance threshold,
    moving the electrode the move distance to a new electrode position along the predetermined path and including the new electrode position in the plurality of locations,
    recording a new sample of the neural signal and including the new sample in the recorded samples,
    detecting, carried out by a processing means, action potentials in the new sample of the neural signal,
    classifying, carried out by a processing means, the action potentials of the new sample into classes,
    calculating, carried out by a processing means, the first signal quality metric for each of the classes,
    identifying, carried out by a processing means, the dominant class,
    for each of the action potentials of the dominant class, determining, carried out by a processing means, the second signal quality metric,
    modeling, carried out by a processing means, the isolation curve as a function of the second signal quality metric of each of the action potentials in the dominant class of a second portion of the recorded samples and the locations of the plurality of locations where each of the recorded samples of the second portion of the recorded samples were recorded, and
    determining, carried out by a processing means, the move distance from the new electrode position to a location along the modeled isolation curve that the modeled isolation curve indicates will improve signal quality.

2. The method of claim 1, wherein classifying the action potentials of each of the recorded samples into classes comprises
    representing each of the action potentials by a predetermined number of features;
    classifying each of the action potentials using the predetermined number of features into one of a predetermined number of classes or an outlier class; and
    determining the predetermined number of classes by calculating the Bayesian Information Criterion value for a plurality of candidate numbers of classes and setting the predetermined number of classes equal to the candidate number of classes that produced the largest Bayesian Information Criterion value.

3. The method of claim 1, wherein classifying the action potentials of each of the recorded samples into classes comprises
    representing each of the action potentials by a predetermined number of principal components; and
    classifying each of the action potentials using the predetermined number of principal components into one of a predetermined number of classes or an outlier class.

4. The method of claim 1, wherein classifying the action potentials of each of the recorded samples into classes comprises
    representing each of the action potentials by a predetermined number of Haar wavelet coefficients; and
    classifying each of the action potentials using the predetermined number of Haar wavelet coefficients into one of a predetermined number of classes or an outlier class.

5. The method of claim 1, wherein classifying the action potentials of each of the recorded samples into classes comprises for each action potential, extracting a segment of the sample corresponding to the action potential from the sample, and for each sample, aligning the extracted segments.

6. The method of the previous claim, wherein aligning, the extracted segments comprises selecting a first segment, selecting a second segment having a first position, determining a first correlation between the first segment and the second segment in the first position, shifting the second segment from the first position to a second position, determining a second correlation between the first segment and the second segment in the second position, determining which of the first and second correlations is greatest, and placing the second segment in the position corresponding to the greatest correlation.

7. The method of claim 1, wherein classifying the action potentials of each of the recorded samples into classes comprises
    representing each of the action potentials by a predetermined number of features;
    classifying each of the action potentials using the predetermined number of features into one of a predetermined number of classes or an outlier class by constructing a finite mixture model to model the probability density function of action potentials in a feature space defined by the predetermined number of features used to represent each of the action potentials, wherein the finite mixture model comprises a plurality of component probability density functions, and one of the component probability density functions of the plurality corresponds to the outlier class and the other component probability density functions correspond to the predetermined number of classes; and
    assigning each of the action potentials to one of the component probability density functions based upon the probability the action potential as represented by the predetermined number of features belongs to each of the component probability density functions.

8. The method of claim 7, wherein the component probability density function corresponding to the outlier class is a uniform distribution and the component probability density functions corresponding to the predetermined number of classes are Gaussian distributions.

9. The method of claim 7, wherein the component probability density functions corresponding to the predetermined number of classes each have a set of parameter values and the sets of parameter values are determined by maximizing the likelihood the action potentials as represented by the predetermined number of features belong to the finite mixture model constructed using the sets of parameter values.

10. The method of claim 1, wherein classifying the action potentials of each of the recorded samples into classes comprises
representing each of the action potentials by a predetermined number of features;
classifying each of the action potentials using the predetermined number of features into one of a predetermined number of classes or an outlier class; and
determining the predetermined number of classes comprising:
determining a plurality of candidate predetermined number of classes;
for each of the candidate predetermined number of classes, constructing a finite mixture model to model the probability density function of action potentials in a feature space defined by the predetermined number of features used to represent each of the action potentials, wherein the finite mixture model comprises a plurality of component probability density functions, and one of the component probability density functions of the plurality corresponds to the outlier class and the other component probability density functions correspond to the candidate predetermined number of classes;
for each of the finite mixture models constructed, determining a likelihood the action potentials as represented by the predetermined number of features belong to the finite mixture model constructed; and
setting the predetermined number of classes equal to the candidate predetermined number of classes used to construct the finite mixture model corresponding to the greatest likelihood.

11. The method of claim 1, wherein the modeled isolation curve comprises a sum of a predetermined number of basis functions having the form $u^{(i-1)}$ wherein u is the position of the electrode when the sample was recorded and i takes the value of a natural number in a set from one to the predetermined number of basis functions.

12. The method of claim 1, wherein the modeled isolation curve comprises a sum of a predetermined number of basis functions, each of the basis functions having a form selected by an operator.

13. The method of claim 1, wherein the modeled isolation curve comprises a sum of a predetermined number of basis functions and the predetermined number of basis functions is determined using a Bayesian Model Section.

14. The method of claim 1, wherein the modeled isolation curve comprises a sum of a predetermined number of basis functions, each of the basis functions comprises an expansion coefficient, and modeling the isolation curve of the neuron comprises determining the expansion coefficient of each of the basis functions, and determining the expansion coefficient of each of the basis functions comprises using a least squares optimization to determine a value for each of the expansion coefficients.

15. The method of claim 1, further comprising, comparing the move distance to a maximum move threshold, and if the move distance is greater than the maximum move threshold, setting the move distance equal to predetermined maximum move distance.

16. The method of claim 1, wherein the action potentials of each of the recorded samples are classified into classes using unsupervised clustering.

17. The method of claim 1, wherein the modeled isolation curve is modeled using unsupervised regression analysis.

18. A method of monitoring a neural signal using an electrode disposed inside a brain comprising:
moving the electrode inside the brain to a plurality of locations and at each location, collecting a sample of the neural signal to obtain a plurality of samples of the neural signal;
collecting a sample of the neural signal to obtain a new sample of the neural signal;
detecting, carried out by a processing means, action potentials in the new neural signal, each action potential having an amplitude;
using unsupervised clustering to classify the action potentials into clusters;
identifying, carried out by a processing means, a dominant cluster;
calculating, carried out by a processing means, a current signal quality metric as a function of the amplitude of the action potentials of the dominant cluster; and
as long as the current signal quality metric is less than a minimum signal quality threshold,
modifying the plurality of samples to include the new sample,
using a portion of the plurality of samples to create a model of an isolation curve of the neural signal,
determining, carried out by a processing means, a move distance to a new location that the model indicates will improve signal quality,
moving the electrode the move distance,
after moving the electrode, re-sampling the neural signal to replace the new sample,
detecting, carried out by a processing means, action potentials in the new neural signal, each action potential having an amplitude,
using unsupervised clustering to classifying the action potentials into clusters,
re-identifying, carried out by a processing means, the dominant cluster, and
recalculating, carried out by a processing means, the current signal quality metric as a function of the amplitude of the action potentials of the dominant cluster.

19. The method of claim 18, wherein using unsupervised clustering to classify the action potentials into clusters comprises
representing each of the action potentials by a predetermined number of features;
clustering each of the action potentials using the predetermined number of features into one of a predetermined number of clusters or an outlier cluster; and
determining the predetermined number of clusters by calculating the Bayesian Information Criterion value for a plurality of candidate numbers of clusters and setting the predetermined number of clusters equal to the candidate number of clusters that produced the largest Bayesian Information Criterion value.

20. The method of claim 18, wherein using unsupervised clustering to classify the action potentials into clusters comprises,
representing each of the action potentials by a predetermined number of principal components; and
clustering each of the action potentials using the predetermined number of principal components into one of a predetermined number of clusters or an outlier cluster.

21. The method of claim 18, wherein using unsupervised clustering to classify the action potentials into clusters comprises
representing each of the action potentials by a predetermined number of Haar wavelet coefficients; and
clustering each of the action potentials using the predetermined number of Haar wavelet coefficients into one of a predetermined number of clusters or an outlier cluster.

22. The method of claim 18, wherein using unsupervised clustering to classify the action potentials into clusters comprises
representing each of the action potentials by a predetermined number of features; and
clustering each of the action potentials using the predetermined number of features into one of a predetermined number of clusters or an outlier cluster by
constructing a finite mixture model to model the probability density function of action potentials in a feature space defined by the predetermined number of features used to represent each of the action potentials, wherein the finite mixture model comprises a plurality of component probability density functions, and one of the component probability density functions of the plurality corresponds to the outlier class and the other component probability density functions correspond to the predetermined number of classes; and
assigning each of the action potentials to one of the component probability density functions based upon the probability the action potential as represented by the predetermined number of features belongs to each of the component probability density functions.

23. The method of claim 22, wherein the component probability density function corresponding to the outlier cluster is a uniform distribution and the component probability density functions corresponding to the predetermined number of clusters are Gaussian distributions.

24. The method of claim 18, wherein using unsupervised clustering to classify the action potentials into clusters comprises
representing each of the action potentials by a predetermined number of features;
clustering each of the action potentials using the predetermined number of features into one of a predetermined number of clusters or an outlier cluster; and
determining the predetermined number of clusters comprising:
determining a plurality of candidate predetermined number of clusters;
for each of the candidate predetermined number of clusters, constructing a finite mixture model to model the probability density function of action potentials in a feature space defined by the predetermined number of features used to represent each of the action potentials, wherein the finite mixture model comprises a plurality of component probability density functions, and one of the component probability density functions of the plurality corresponds to the outlier cluster and the other component probability density functions Correspond to the candidate predetermined number of clusters;
for each of the finite mixture models constructed, determining a likelihood the action potentials as represented by the predetermined number of features belong to the finite mixture model constructed; and
setting the predetermined number of classes equal to the candidate predetermined number of classes used to construct the finite mixture model corresponding to the greatest likelihood.

25. The method of claim 18, wherein the model of the isolation curve comprises a sum of a predetermined number of basis functions having the form $u^{(i-l)}$ wherein u is the position of the electrode when the sample was recorded and i takes the value of a natural number in a set from one to the predetermined number of basis functions.

26. The method of claim 25, wherein the predetermined number of basis functions is determined using a Bayesian Model Section.

27. The method of claim 18, wherein the model of the isolation curve is created using unsupervised regression analysis.

28. A system comprising:
a microdrive comprising an electrode disposed within a brain, the electrode being configured to detect a neural signal of the brain, and a piezoelectric actuator configured to move the electrode along a predetermined path of travel in response to a command signal;
a memory comprising instructions; and
a processor coupled to the memory, coupled to the electrode, and configured to execute the instructions and provide the command signal to the electrode,
wherein the instructions comprise instructions directing the processor to generate the command signal, the instructions comprising:
instructions for generating the command signal to move the electrode a predetermined search distance, after the electrode is moved detect action potentials in the neural signal detected by the electrode, and until action potentials are not detected repeatedly generate the command signal to move the electrode the predetermined search distance,
instructions for generating a command signal to move the electrode a second predetermined distance a predetermined number of times, and after each move, record the neural signal, and
instructions for using the predetermined number of recorded neural signals detected by the electrode to model an isolation curve, use the isolation curve to determine a move distance, and if the move distance is greater than a minimum move threshold, generate a command signal to move the electrode the move distance.

29. A non-transitory computer readable-medium having instructions executable by a processor coupled to a microdrive comprising a movable electrode, the instructions comprising:
instructions for detecting action potentials comprising:
instructions for determining a search distance,
instructions for moving the electrode of the microdrive the search distance,
after the move, instructions for recording the neural signal,
instructions for determining whether action potentials are present in the recorded neural signal, and if action potentials are not present in the recorded neural signal, instructions directing the processor to execute the instructions for detecting action potentials;

instructions for moving the electrode to a plurality of electrode positions and after each move, recording the neural signal to create a plurality of neural signal recordings each having a corresponding recorded electrode position;

instructions for modeling an isolation curve of a neuron having an order using the neural signal recordings and corresponding recorded electrode positions and if the order is greater than a predetermined order threshold, instructions for using the model of the isolation curve to determine a move distance to a new location that the model of the isolation curve indicates will improve signal quality; and instructions for iteratively moving the electrode comprising:

comparing the move distance to a move threshold value, if the move distance is greater than the move threshold value, moving the electrode of the microdrive the move distance to a new electrode position, after the move, recording a new neural signal and the new electrode position, determining a signal quality metric using the new neural signal, and comparing the signal quality metric to a minimum signal quality threshold, if the signal quality metric is below the minimum signal quality threshold, modifying the plurality of neural signal recordings to include the new neural signal, modifying the electrode positions corresponding to the plurality of neural signal recordings to include the new electrode position, and executing the instructions for modeling the isolation curve of a neuron and the instructions for iteratively moving the electrode.

30. The computer readable-medium of claim 29, comprising instructions for comparing the signal quality metric to a maximum signal quality threshold and if the signal quality metric exceeds the maximum signal quality threshold, determining a back away distance and moving the electrode the back away distance.

31. The computer readable-medium of claim 29, comprising instructions for comparing the signal quality metric to a minimum track signal quality threshold and if the signal quality metric is less than the minimum track signal quality threshold, executing the instructions for detecting action potentials.

32. The computer readable-medium of claim 29, comprising instructions for maintaining neural signal quality comprising instructions for periodically recording a sample neural signal at a sample electrode position, determining a signal quality metric using the sample neural signal, comparing the signal quality metric to the minimum signal quality threshold, if the signal quality metric is below the minimum signal quality threshold, modifying the plurality of neural signal recordings to include the sample neural signal, modifying the electrode positions corresponding with the plurality of neural signal recordings to include the sample electrode position, and executing the instructions for modeling the isolation curve of a neuron and the instructions for iteratively moving the electrode.

33. The computer readable-medium of claim 29, comprising instructions for maintaining neural signal quality comprising instructions for periodically recording a sample neural signal, determining a signal quality metric using the sample neural signal, comparing the signal quality metric to a minimum track signal quality threshold and if the signal quality metric is less than the minimum track signal quality threshold, executing the instructions for detecting action potentials.

* * * * *